(12) United States Patent
McDaniel

(10) Patent No.: US 9,814,906 B2
(45) Date of Patent: *Nov. 14, 2017

(54) METHOD AND APPARATUS FOR SKIN TREATMENT

(71) Applicant: L'OREAL, Paris (FR)

(72) Inventor: David H. McDaniel, Virginia Beach, VA (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/693,369

(22) Filed: Apr. 22, 2015

(65) Prior Publication Data

US 2015/0328478 A1    Nov. 19, 2015

Related U.S. Application Data

(60) Continuation of application No. 12/583,578, filed on Aug. 21, 2009, now Pat. No. 9,017,391, which is a
(Continued)

(51) Int. Cl.
*A61N 5/06* (2006.01)
*A61B 18/20* (2006.01)
(Continued)

(52) U.S. Cl.
CPC .......... *A61N 5/0616* (2013.01); *A61B 18/203* (2013.01); *A61K 41/0057* (2013.01); *A61K 41/0071* (2013.01); *A61N 5/0617* (2013.01); *A61B 2017/00765* (2013.01); *A61B 2017/22085* (2013.01); *A61B 2018/00452* (2013.01);
(Continued)

(58) Field of Classification Search
CPC .. A61N 5/06; A61N 5/067; A61N 2005/0616; A61N 2005/0652; A61B 18/18; A61B 18/20; A61B 18/203
USPC ...... 607/88–91, 93, 96, 100; 606/3, 8, 9–12; 128/898
See application file for complete search history.

(56) References Cited

U.S. PATENT DOCUMENTS 3,499,437 A    3/1970   Balamuth
3,876,907 A    4/1975   Widmayer
(Continued)

FOREIGN PATENT DOCUMENTS

CA    2410962      12/2001
EP    3 037 131 A2    6/1916
(Continued)

OTHER PUBLICATIONS

U.S. Appl. No. 14/807,653, filed Jul. 23, 2015, McDaniel.
(Continued)

*Primary Examiner* — Ahmed Farah
(74) *Attorney, Agent, or Firm* — Oblon, McClelland, Maier & Neustadt, L.L.P.

(57) ABSTRACT

Disclosed is a system and method for treatment of skin disorders. More particularly, the disclosed invention is directed toward the use of multiple light sources for treating skin with or without the use of a topical compositions or photomodulation enhancing agents. Dual light emitting diodes may, for example, be used at relatively low power (less than about 10 J/cm2) to photomodulate skin or living tissue to reduce wrinkles, fine lines, acne, acne bacteria, and other skin disorders.

7 Claims, 11 Drawing Sheets

Front View Light Panel

Related U.S. Application Data continuation of application No. 11/332,517, filed on Jan. 17, 2006, now abandoned, which is a continuation of application No. 11/119,378, filed on May 2, 2005, now Pat. No. 7,201,765, which is a division of application No. 09/933,870, filed on Aug. 22, 2001, now Pat. No. 6,887,260, which is a continuation-in-part of application No. 09/819,082, filed on Feb. 15, 2001, now abandoned, which is a division of application No. 09/203,178, filed on Nov. 30, 1998, now Pat. No. 6,283,956.

(51) Int. Cl.
  *A61K 41/00* (2006.01)
  *A61N 5/067* (2006.01)
  *A61B 17/00* (2006.01)
  *A61B 17/22* (2006.01)
  *A61B 18/00* (2006.01)
  *A61B 18/18* (2006.01)

(52) U.S. Cl.
  CPC ............ *A61B 2018/00476* (2013.01); *A61B 2018/1807* (2013.01); *A61N 5/062* (2013.01); *A61N 2005/067* (2013.01); *A61N 2005/0651* (2013.01); *A61N 2005/0652* (2013.01); *A61N 2005/0659* (2013.01)

(56) References Cited

U.S. PATENT DOCUMENTS

| | | |
|---|---|---|
| 3,930,335 A | 1/1976 | Widmayer |
| 4,069,823 A | 1/1978 | Isakov et al. |
| 4,309,989 A | 1/1982 | Fahim |
| 4,458,678 A | 7/1984 | Yannas et al. |
| 4,558,700 A | 12/1985 | Mutzhas |
| 4,603,496 A | 8/1986 | Latz et al. |
| 4,621,287 A | 11/1986 | Reitmeier et al. |
| 4,628,422 A | 12/1986 | Ewald |
| 4,629,363 A | 12/1986 | Rose et al. |
| 4,646,743 A | 3/1987 | Parris |
| 4,753,958 A | 6/1988 | Weinstein et al. |
| 4,764,379 A | 8/1988 | Sanders et al. |
| 4,767,402 A | 8/1988 | Kost et al. |
| 4,781,924 A | 11/1988 | Lee et al. |
| 4,822,335 A | 4/1989 | Kawai et al. |
| 4,836,203 A | 6/1989 | Muller et al. |
| 4,837,027 A | 6/1989 | Lee et al. |
| 4,880,001 A | 11/1989 | Weinberg |
| 4,888,354 A | 12/1989 | Chang et al. |
| 4,907,132 A | 3/1990 | Parker |
| 4,930,504 A | 6/1990 | Diamantopoulos et al. |
| 4,932,934 A | 6/1990 | Dougherty et al. |
| 4,935,665 A | 6/1990 | Murata |
| 4,969,912 A | 11/1990 | Kelman et al. |
| 5,001,556 A | 3/1991 | Nakamura et al. |
| 5,012,609 A | 5/1991 | Ignatius et al. |
| 5,016,615 A | 5/1991 | Driller et al. |
| 5,021,452 A | 6/1991 | Labbe et al. |
| 5,034,613 A | 7/1991 | Denk et al. |
| 5,037,432 A | 8/1991 | Molinari |
| 5,071,416 A * | 12/1991 | Heller ............... A61N 5/0601 600/476 |
| 5,147,349 A | 9/1992 | Johnson et al. |
| 5,150,704 A | 9/1992 | Tatebayashi et al. |
| 5,171,215 A | 12/1992 | Flanagan |
| 5,198,465 A | 3/1993 | Dioguardi |
| 5,226,907 A | 7/1993 | Tankovich |
| 5,231,975 A | 8/1993 | Bommannan et al. |
| 5,257,173 A | 10/1993 | Ohmamyuda et al. |
| 5,259,380 A | 11/1993 | Mendes et al. |
| 5,262,401 A | 11/1993 | Vogel et al. |
| 5,266,480 A | 11/1993 | Naughton et al. |
| 5,278,432 A | 1/1994 | Ignatius et al. |
| 5,332,802 A | 7/1994 | Kelman et al. |
| 5,344,434 A | 9/1994 | Talmore |
| 5,358,503 A | 10/1994 | Bertwell et al. |
| 5,360,824 A | 11/1994 | Barker |
| 5,366,498 A | 11/1994 | Brannan et al. |
| 5,397,352 A | 3/1995 | Burres |
| 5,399,583 A | 3/1995 | Levy et al. |
| 5,421,816 A | 6/1995 | Lipkovker |
| 5,423,803 A | 6/1995 | Tankovich et al. |
| 5,425,728 A | 6/1995 | Tankovich |
| 5,445,146 A | 8/1995 | Bellinger |
| 5,445,608 A | 8/1995 | Chen et al. |
| 5,445,611 A | 8/1995 | Eppstein et al. |
| 5,445,634 A | 8/1995 | Keller |
| 5,460,939 A | 10/1995 | Hansbrough et al. |
| 5,474,528 A | 12/1995 | Meserol |
| 5,492,135 A | 2/1996 | Devore |
| 5,500,009 A | 3/1996 | Mendes et al. |
| 5,549,660 A | 8/1996 | Mendes et al. |
| 5,591,444 A | 1/1997 | Boss, Jr. |
| 5,616,140 A | 4/1997 | Prescott |
| 5,618,275 A | 4/1997 | Bock |
| 5,620,478 A | 4/1997 | Eckhouse |
| 5,634,711 A | 6/1997 | Kennedy et al. |
| 5,636,632 A | 6/1997 | Bommannan et al. |
| 5,643,334 A | 7/1997 | Eckhouse et al. |
| 5,647,866 A | 7/1997 | Zaias et al. |
| 5,658,323 A | 8/1997 | Miller |
| 5,660,461 A | 8/1997 | Ignatius et al. |
| 5,660,836 A | 8/1997 | Knowlton |
| 5,660,850 A | 8/1997 | Boss, Jr. |
| 5,662,644 A | 9/1997 | Swor |
| 5,665,053 A | 9/1997 | Jacobs |
| 5,665,372 A | 9/1997 | Boss, Jr. |
| 5,669,916 A | 9/1997 | Anderson |
| 5,683,380 A | 11/1997 | Eckhouse et al. |
| 5,686,112 A | 11/1997 | Liedtke |
| 5,698,866 A | 12/1997 | Doiron et al. |
| 5,707,401 A | 1/1998 | Talmore |
| 5,728,090 A | 3/1998 | Martin et al. |
| 5,752,948 A | 5/1998 | Tankovich et al. |
| 5,752,949 A | 5/1998 | Tankovich et al. |
| 5,755,752 A | 5/1998 | Segal |
| 5,766,214 A | 6/1998 | Mehl, Sr. et al. |
| 5,766,233 A | 6/1998 | Thiberg |
| 5,766,234 A | 6/1998 | Chen et al. |
| 5,773,609 A | 6/1998 | Robinson et al. |
| 5,800,478 A | 9/1998 | Chen et al. |
| 5,800,479 A | 9/1998 | Thiberg |
| 5,810,801 A | 9/1998 | Anderson et al. |
| 5,814,599 A | 9/1998 | Mitragotri et al. |
| 5,817,089 A | 10/1998 | Tankovich et al. |
| 5,829,448 A | 11/1998 | Fisher et al. |
| 5,836,999 A | 11/1998 | Eckhouse et al. |
| 5,837,224 A | 11/1998 | Voorhees et al. |
| 5,843,072 A | 12/1998 | Furumoto et al. |
| 5,849,029 A | 12/1998 | Eckhouse et al. |
| 5,871,480 A | 2/1999 | Tankovich |
| 5,904,659 A | 5/1999 | Duarte et al. |
| 5,913,883 A | 6/1999 | Alexander et al. |
| 5,932,240 A | 8/1999 | D'Angelo et al. |
| 5,947,921 A | 9/1999 | Johnson et al. |
| 5,951,596 A | 9/1999 | Bellinger |
| 5,954,675 A | 9/1999 | Dellagatta |
| 5,968,034 A | 10/1999 | Fullmer et al. |
| 5,997,569 A | 12/1999 | Chen et al. |
| 6,024,717 A | 2/2000 | Ball et al. |
| 6,030,374 A | 2/2000 | McDaniel |
| 6,048,301 A | 4/2000 | Sabuda |
| 6,050,990 A | 4/2000 | Tankovich et al. |
| 6,063,108 A | 5/2000 | Salansky |
| 6,074,382 A | 6/2000 | Asah et al. |
| 6,096,066 A | 8/2000 | Chen |
| 6,099,522 A | 8/2000 | Knopp |
| 6,110,106 A | 8/2000 | MacKinnon et al. |
| 6,113,559 A | 9/2000 | Klopotek |
| 6,120,497 A | 9/2000 | Anderson et al. |
| 6,130,254 A | 10/2000 | Fisher et al. |
| 6,143,287 A | 11/2000 | Ben-Hur et al. |

(56) References Cited

U.S. PATENT DOCUMENTS

| | | | |
|---|---|---|---|
| 6,162,211 A | 12/2000 | Tankovich et al. |
| 6,171,331 B1 | 1/2001 | Bagraev et al. |
| 6,171,332 B1 | 1/2001 | Whitehurst |
| 6,174,325 B1 | 1/2001 | Eckhouse |
| 6,183,773 B1 | 2/2001 | Anderson |
| 6,187,029 B1 | 2/2001 | Shapiro et al. |
| 6,190,315 B1 | 2/2001 | Kost et al. |
| 6,190,376 B1 | 2/2001 | Asah |
| 6,214,034 B1 | 4/2001 | Azar |
| 6,221,095 B1 | 4/2001 | Van Zuylen et al. |
| 6,223,071 B1 | 4/2001 | Lundahl et al. |
| 6,231,528 B1 | 5/2001 | Kaufman et al. |
| 6,238,424 B1 | 5/2001 | Thiberg |
| 6,251,127 B1 | 6/2001 | Biel |
| 6,267,779 B1 | 7/2001 | Gerdes |
| 6,273,884 B1 | 8/2001 | Altshuler |
| 6,283,956 B1 | 9/2001 | McDaniel |
| 6,290,713 B1 | 9/2001 | Russell |
| 6,302,874 B1 | 10/2001 | Zhang et al. |
| 6,312,450 B1 | 11/2001 | Yavitz et al. |
| 6,387,089 B1 | 5/2002 | Kreindel et al. |
| 6,398,753 B2 | 6/2002 | McDaniel |
| 6,413,268 B1 | 7/2002 | Hartman |
| 6,436,127 B1 | 8/2002 | Anderson et al. |
| 6,443,946 B2 | 9/2002 | Clement et al. |
| 6,443,978 B1 | 9/2002 | Zharov |
| 6,459,087 B1 | 10/2002 | Kaas |
| 6,471,716 B1 | 10/2002 | Pecukonis |
| 6,497,719 B2 | 12/2002 | Pearl et al. |
| 6,524,330 B1 | 2/2003 | Khoobehi et al. |
| 6,602,275 B1 | 8/2003 | Sullivan |
| 6,629,971 B2 | 10/2003 | McDaniel |
| 6,630,516 B2 | 10/2003 | Varani et al. |
| 6,645,230 B2 | 11/2003 | Whitehurst |
| 6,663,659 B2 | 12/2003 | McDaniel |
| 6,664,217 B1 | 12/2003 | Puvvada et al. |
| 6,676,655 B2 | 1/2004 | McDaniel |
| 6,709,866 B2 | 3/2004 | Robertson et al. |
| 6,723,698 B2 | 4/2004 | Rueger et al. |
| 6,723,798 B1 | 4/2004 | Yoo |
| 6,746,444 B2 | 6/2004 | Key |
| 6,835,306 B2 | 12/2004 | Caldwell |
| 6,866,678 B2 | 3/2005 | Shenderova |
| 6,881,212 B1 | 4/2005 | Schweikert et al. |
| 6,887,260 B1 * | 5/2005 | McDaniel ............ A61B 18/203 606/10 |
| 6,936,044 B2 | 8/2005 | McDaniel |
| 7,004,933 B2 | 2/2006 | McDaniel |
| 7,033,381 B1 | 4/2006 | Larsen |
| 7,081,128 B2 | 7/2006 | Hart et al. |
| 7,115,120 B2 | 10/2006 | Lin |
| 7,147,863 B2 | 12/2006 | Fisher et al. |
| 7,195,755 B2 | 3/2007 | Nguyen et al. |
| 7,201,765 B2 | 4/2007 | McDaniel |
| 7,204,832 B2 * | 4/2007 | Altshuler ............ A45D 26/0061 606/22 |
| 7,258,695 B2 | 8/2007 | Carullo et al. |
| 7,264,629 B2 | 9/2007 | Simkin et al. |
| 7,267,673 B2 | 9/2007 | Pilcher et al. |
| 7,309,335 B2 | 12/2007 | Altshuler et al. |
| 7,331,952 B2 | 2/2008 | Walneck et al. |
| 7,354,432 B2 | 4/2008 | Eells et al. |
| 7,402,832 B2 * | 7/2008 | Lee ..................... B82Y 10/00 257/17 |
| 7,438,719 B2 | 10/2008 | Chung et al. |
| 7,470,270 B2 | 12/2008 | Azar et al. |
| 7,494,503 B2 | 2/2009 | McDaniel |
| 7,511,031 B2 | 3/2009 | Chen |
| 7,559,944 B2 | 7/2009 | Whang |
| 7,597,708 B2 | 10/2009 | Carullo et al. |
| 7,618,414 B2 | 11/2009 | Connors et al. |
| 8,188,074 B2 | 5/2012 | Brown et al. |
| 8,328,794 B2 | 12/2012 | Altshuler et al. |
| 8,372,433 B2 | 2/2013 | Shinoka et al. |
| 8,651,111 B2 | 2/2014 | McDaniel |
| 8,651,112 B2 | 2/2014 | McDaniel |
| 2001/0013349 A1 | 8/2001 | Clement |
| 2001/0023363 A1 | 9/2001 | Harth et al. |
| 2001/0053347 A1 | 12/2001 | Varani et al. |
| 2002/0028185 A1 | 3/2002 | Fisher et al. |
| 2002/0029071 A1 | 3/2002 | Whitehurst |
| 2002/0123746 A1 | 9/2002 | McDaniel |
| 2002/0161357 A1 | 10/2002 | Anderson et al. |
| 2002/0173833 A1 | 11/2002 | Korman et al. |
| 2002/0183724 A1 | 12/2002 | Neev |
| 2002/0198575 A1 | 12/2002 | Sullivan |
| 2003/0004499 A1 | 1/2003 | McDaniel |
| 2003/0004556 A1 | 1/2003 | McDaniel |
| 2003/0060811 A1 | 3/2003 | McDaniel |
| 2003/0129154 A1 | 7/2003 | McDaniel |
| 2004/0039378 A1 | 2/2004 | Lin |
| 2004/0215293 A1 | 10/2004 | Eells et al. |
| 2005/0090877 A1 | 4/2005 | Harth et al. |
| 2005/0197681 A1 | 9/2005 | Barolet et al. |
| 2006/0129209 A1 | 6/2006 | McDaniel |
| 2006/0184214 A1 | 8/2006 | McDaniel |
| 2006/0200213 A1 | 9/2006 | McDaniel |
| 2006/0212025 A1 | 9/2006 | McDaniel |
| 2006/0265030 A1 | 11/2006 | McDaniel |
| 2007/0073276 A1 | 3/2007 | Wilkens et al. |
| 2007/0128576 A1 | 6/2007 | Boutoussov |
| 2007/0129613 A1 | 6/2007 | Rochester et al. |
| 2007/0129711 A1 | 6/2007 | Altshuler et al. |
| 2007/0129776 A1 | 6/2007 | Robins et al. |
| 2007/0129778 A1 | 6/2007 | Dougal |
| 2007/0149900 A1 | 6/2007 | Lin |
| 2007/0149901 A1 | 6/2007 | Gordon et al. |
| 2007/0150030 A1 | 6/2007 | Pearl et al. |
| 2007/0156208 A1 | 7/2007 | Havell et al. |
| 2007/0167999 A1 | 7/2007 | Breden et al. |
| 2007/0168000 A1 | 7/2007 | Happawana et al. |
| 2007/0173912 A1 | 7/2007 | Amornsiripanitch |
| 2007/0173913 A1 | 7/2007 | Anderson et al. |
| 2007/0179482 A1 | 8/2007 | Anderson |
| 2007/0179574 A1 | 8/2007 | Elliott |
| 2007/0198004 A1 | 8/2007 | Altshuler et al. |
| 2007/0208326 A1 | 9/2007 | Connors et al. |
| 2007/0208328 A1 | 9/2007 | Boutoussov et al. |
| 2007/0208395 A1 | 9/2007 | Leclerc et al. |
| 2007/0208396 A1 | 9/2007 | Whatcott et al. |
| 2007/0208400 A1 | 9/2007 | Nadkarni et al. |
| 2007/0213696 A1 | 9/2007 | Altshuler et al. |
| 2007/0219604 A1 | 9/2007 | Yaroslavsky et al. |
| 2007/0219605 A1 | 9/2007 | Yaroslavsky et al. |
| 2007/0231255 A1 | 10/2007 | Barolet et al. |
| 2007/0239142 A1 | 10/2007 | Altshuler et al. |
| 2007/0239147 A1 | 10/2007 | Manstein et al. |
| 2007/0299486 A1 | 12/2007 | Hoenig et al. |
| 2008/0009923 A1 | 1/2008 | Paithankar et al. |
| 2008/0015555 A1 | 1/2008 | Manstein et al. |
| 2008/0021528 A1 | 1/2008 | Carullo, Jr. et al. |
| 2008/0031833 A1 | 2/2008 | Oblong et al. |
| 2008/0031924 A1 | 2/2008 | Gilson et al. |
| 2008/0033516 A1 | 2/2008 | Altshuler et al. |
| 2008/0035864 A1 | 2/2008 | Fiset |
| 2008/0039906 A1 | 2/2008 | Huang et al. |
| 2008/0045933 A1 | 2/2008 | Perl |
| 2008/0051856 A1 | 2/2008 | Vizethum et al. |
| 2008/0058783 A1 | 3/2008 | Altshuler et al. |
| 2008/0058784 A1 | 3/2008 | Manstein |
| 2008/0058905 A1 | 3/2008 | Wagner |
| 2008/0065056 A1 | 3/2008 | Powell et al. |
| 2008/0065175 A1 | 3/2008 | Redmond |
| 2008/0077199 A1 | 3/2008 | Shefi et al. |
| 2008/0082148 A1 | 4/2008 | Bernstein |
| 2008/0082149 A1 | 4/2008 | Bernstein |
| 2008/0091179 A1 | 4/2008 | Durkin et al. |
| 2008/0097278 A1 | 4/2008 | Cole et al. |
| 2008/0097419 A1 | 4/2008 | MacFarland et al. |
| 2008/0103560 A1 | 5/2008 | Powell et al. |
| 2008/0106896 A1 | 5/2008 | Liu et al. |
| 2008/0139901 A1 | 6/2008 | Altshuler et al. |
| 2008/0147054 A1 | 6/2008 | Altshuler et al. |
| 2008/0147148 A1 | 6/2008 | Baldacchini |

(56) References Cited

U.S. PATENT DOCUMENTS

| | | |
|---|---|---|
| 2008/0172112 A1 | 7/2008 | Gourgouliatos et al. |
| 2008/0172114 A1 | 7/2008 | Gourgouliatos et al. |
| 2008/0177255 A1 | 7/2008 | Bernardini |
| 2008/0183161 A1 | 7/2008 | Walneck et al. |
| 2008/0200908 A1 | 8/2008 | Domankevitz |
| 2008/0203280 A1 | 8/2008 | Rizoiu et al. |
| 2008/0208294 A1 | 8/2008 | Pierce |
| 2008/0208295 A1 | 8/2008 | Cumbie et al. |
| 2008/0234669 A1 | 9/2008 | Kauvar |
| 2008/0234786 A1 | 9/2008 | Cumbie |
| 2008/0255640 A1 | 10/2008 | Kipp et al. |
| 2008/0262394 A1 | 10/2008 | Pryor et al. |
| 2008/0262482 A1 | 10/2008 | Hantash et al. |
| 2008/0262576 A1 | 10/2008 | Creamer et al. |
| 2008/0267814 A1 | 10/2008 | Bornstein |
| 2008/0269732 A1 | 10/2008 | Pyun |
| 2008/0269733 A1 | 10/2008 | Anderson et al. |
| 2008/0269844 A1 | 10/2008 | Logslett |
| 2008/0269848 A1 | 10/2008 | Birmingham et al. |
| 2008/0269849 A1 | 10/2008 | Lewis |
| 2008/0275532 A1 | 11/2008 | Yamazaki |
| 2008/0281307 A1 | 11/2008 | Donahue |
| 2008/0294151 A1 | 11/2008 | Whitaker et al. |
| 2008/0294152 A1 | 11/2008 | Altshuler et al. |
| 2009/0012508 A1 | 1/2009 | Dougal |
| 2009/0018621 A1 | 1/2009 | Vogler et al. |
| 2009/0018622 A1 | 1/2009 | Asvadi et al. |
| 2009/0024116 A1 | 1/2009 | Mulhauser et al. |
| 2009/0043293 A1 | 2/2009 | Pankratov et al. |
| 2009/0062889 A1 | 3/2009 | Kiessl et al. |
| 2009/0082836 A1 | 3/2009 | Schell |
| 2009/0088824 A1 | 4/2009 | Baird et al. |
| 2009/0105791 A1 | 4/2009 | McGinnis et al. |
| 2009/0112192 A1 | 4/2009 | Barolet et al. |
| 2009/0112294 A1 | 4/2009 | Huang et al. |
| 2009/0149843 A1 | 6/2009 | Smits et al. |
| 2009/0177190 A1 | 7/2009 | Lee |
| 2009/0177253 A1 | 7/2009 | Darm et al. |
| 2009/0177256 A1 | 7/2009 | Ripper et al. |
| 2009/0187169 A1 | 7/2009 | Durkin et al. |
| 2009/0198173 A1 | 8/2009 | Samuel et al. |
| 2009/0227996 A1 | 9/2009 | Powell et al. |
| 2009/0234253 A1 | 9/2009 | Vandenbelt et al. |
| 2009/0234337 A1 | 9/2009 | Ely et al. |
| 2009/0234341 A1 | 9/2009 | Roth |
| 2009/0234342 A1 | 9/2009 | Ely et al. |
| 2009/0247932 A1 | 10/2009 | Barolet |
| 2009/0251057 A1 | 10/2009 | Son et al. |
| 2009/0254154 A1 | 10/2009 | De Taboada et al. |
| 2009/0254156 A1 | 10/2009 | Powell et al. |
| 2009/0270845 A1 | 10/2009 | Birmingham et al. |
| 2009/0270946 A1 | 10/2009 | Spivak |
| 2009/0270953 A1 | 10/2009 | Ecker et al. |
| 2010/0121254 A1 | 5/2010 | McDaniel |
| 2010/0137950 A1 | 6/2010 | McDaniel |
| 2010/0174222 A1 | 7/2010 | McDaniel |
| 2010/0256550 A1 | 10/2010 | McDaniel |

FOREIGN PATENT DOCUMENTS

| | | |
|---|---|---|
| EP | 0159446 | 10/1985 |
| EP | 0298661 | 1/1989 |
| EP | 0320080 | 6/1989 |
| EP | 1839705 | 3/2007 |
| EP | 1818077 | 8/2007 |
| EP | 1837050 | 9/2007 |
| EP | 1839704 | 10/2007 |
| EP | 1842571 | 10/2007 |
| EP | 1857145 | 11/2007 |
| EP | 1878466 | 1/2008 |
| EP | 1916016 | 4/2008 |
| EP | 1920798 | 5/2008 |
| EP | 1935452 | 6/2008 |
| EP | 1958662 | 8/2008 |
| EP | 1964590 | 9/2008 |
| EP | 2044901 | 4/2009 |
| EP | 2044973 | 4/2009 |
| EP | 2044974 | 4/2009 |
| EP | 2055349 | 5/2009 |
| EP | 2106198 | 9/2009 |
| EP | 2106780 | 10/2009 |
| EP | 2106824 | 10/2009 |
| EP | 2110159 | 10/2009 |
| GB | 2262043 | 6/1993 |
| GB | 2360461 | 9/2001 |
| GB | 2360641 | 9/2001 |
| JP | H01-136668 | 5/1989 |
| JP | 07-016304 | 1/1995 |
| JP | H07-100219 | 4/1995 |
| JP | H07505614 | 6/1995 |
| JP | H08308943 | 11/1996 |
| JP | H09-508031 | 8/1997 |
| JP | H10-503109 | 3/1998 |
| JP | 2000-202044 | 7/2000 |
| JP | 2002-522110 | 7/2002 |
| JP | 2002-535101 | 10/2002 |
| JP | 2005-503388 | 2/2005 |
| JP | 2010-047590 | 3/2010 |
| SU | 1724269 | 4/1992 |
| WO | WO 93/009847 | 5/1993 |
| WO | WO 93/009874 | 5/1993 |
| WO | WO 93/021842 | 11/1993 |
| WO | WO 95/019809 | 7/1995 |
| WO | WO 96/011723 | 4/1996 |
| WO | WO 96/024406 | 8/1996 |
| WO | WO 97/046279 | 12/1997 |
| WO | WO 98/011723 | 3/1998 |
| WO | WO 98/014453 | 4/1998 |
| WO | WO 98/050034 | 11/1998 |
| WO | WO 99/004628 | 2/1999 |
| WO | WO 99/019024 | 4/1999 |
| WO | WO 99/020336 | 4/1999 |
| WO | WO 99/039763 | 8/1999 |
| WO | WO 00/002491 | 1/2000 |
| WO | WO 00/002497 | 1/2000 |
| WO | WO 00/007514 | 2/2000 |
| WO | WO 00/032121 | 6/2000 |
| WO | WO 00/040266 | 7/2000 |
| WO | WO 00/044441 | 8/2000 |
| WO | WO 00/057804 | 10/2000 |
| WO | WO 00/074782 | 12/2000 |
| WO | WO 01/014012 | 3/2001 |
| WO | WO 01/040232 | 6/2001 |
| WO | WO 02/057811 | 7/2002 |
| WO | WO 03/001984 | 1/2003 |
| WO | WO 03/002187 | 1/2003 |
| WO | WO 03/005883 | 1/2003 |
| WO | WO 03/017824 | 3/2003 |
| WO | WO 03/086215 | 10/2003 |
| WO | WO 04/075985 | 9/2004 |
| WO | WO 04/092335 | 10/2004 |
| WO | WO 05/011606 | 2/2005 |
| WO | WO 05/077452 | 8/2005 |
| WO | WO 05/089039 | 9/2005 |
| WO | WO 05/096766 | 10/2005 |
| WO | WO 05/115263 | 12/2005 |
| WO | WO 06/013390 | 2/2006 |
| WO | WO 06/099413 | 9/2006 |
| WO | WO 06/107387 | 10/2006 |
| WO | WO 06/116141 | 11/2006 |
| WO | WO 06/125231 | 11/2006 |
| WO | WO 07/013110 | 2/2007 |
| WO | WO 07/036002 | 4/2007 |
| WO | WO 07/044840 | 4/2007 |
| WO | WO 07/066657 | 6/2007 |
| WO | WO 07/087374 | 8/2007 |
| WO | WO 07/092349 | 8/2007 |
| WO | WO 07/096344 | 8/2007 |
| WO | 07/106339 | 9/2007 |
| WO | 07/106856 | 9/2007 |
| WO | WO 07/103132 | 9/2007 |
| WO | WO 07/118303 | 10/2007 |
| WO | WO 07/125336 | 11/2007 |
| WO | WO 07/126339 | 11/2007 |

(56) References Cited

FOREIGN PATENT DOCUMENTS

| | | |
|---|---|---|
| WO | 07/146101 | 12/2007 |
| WO | WO 08/008971 | 1/2008 |
| WO | WO 08/012519 | 1/2008 |
| WO | WO 08/017975 | 2/2008 |
| WO | WO 08/078750 | 7/2008 |
| WO | WO 08/084764 | 7/2008 |
| WO | WO 08/097062 | 8/2008 |
| WO | WO 08/128175 | 10/2008 |
| WO | WO 08/129740 | 10/2008 |
| WO | WO 08/129741 | 10/2008 |
| WO | WO 08/131079 | 10/2008 |
| WO | WO 08/131343 | 10/2008 |
| WO | WO 08/135548 | 11/2008 |
| WO | WO 08/135658 | 11/2008 |
| WO | WO 08/137489 | 11/2008 |
| WO | WO 08/146219 | 12/2008 |
| WO | WO 08/146220 | 12/2008 |
| WO | WO 08/146255 | 12/2008 |
| WO | WO 09/003295 | 1/2009 |
| WO | WO 09/008967 | 1/2009 |
| WO | WO 09/014034 | 1/2009 |
| WO | WO 09/016598 | 2/2009 |
| WO | WO 09/016963 | 2/2009 |
| WO | WO 09/023568 | 2/2009 |
| WO | WO 09/023968 | 2/2009 |
| WO | WO 09/038720 | 3/2009 |
| WO | WO 09/056838 | 5/2009 |
| WO | WO 09/059270 | 5/2009 |
| WO | WO 09/064034 | 5/2009 |
| WO | WO 09/089177 | 7/2009 |
| WO | WO 09/107095 | 9/2009 |
| WO | WO 09/117323 | 9/2009 |
| WO | WO 09/118617 | 10/2009 |
| WO | WO 09/121158 | 10/2009 |
| WO | WO 09/123196 | 10/2009 |
| WO | WO 09/125338 | 10/2009 |
| WO | WO 09/132585 | 11/2009 |
| WO | WO 09/137612 | 11/2009 |
| ZA | 9707751 | 3/1998 |

OTHER PUBLICATIONS

Jennato S., et al. (May 2001), "What Color is my LED?" Photonics Spectra.

Laakso, et al.(1997), "Pain Scores and Side Effects in Response to Low Level Laser Therapy (LLLT) for Myofascial Trigger Points", Laser Therapy 9:67-72.

Labbe et al., (1990), "Laser Phobioactivation Mechanisms: In Vitro Studies Using Ascorbic Acid Uptake and Hydroxyproline Formation as Biochemical Markers of Irradiation Response", Lasers in Surgery and Medicine 10, pp. 201-207.

Liberman et al. (1996), "Light Years Ahead", pp. 277-283.

Lieb, Linda, et al. (1992), "Topical Delivery Enhancement with Multilamellar Liposomes into Pilosebaceous Units: In Vitro Evaluation Using Fluorescent Techniques with the Hamster Ear Model", The Journal of Investigative Dermatology 99(1).

Li, Lingna ,et al. (1992), "Product-Delivering Liposomes Specifically Target Hair Follicles in Histocultured Intact Skin", In Vitro Cell Dev. Biol. 281, pp. 679-681.

Liu et al. (2002), "Inhibition of AP-1 Transcription Factor Causes Blockade of Multiple Signal Transduction Pathways and Inhibits Breast Cancer Growth", Oncogene 21:7680-7689.

Loevschall, (1994), "Effect of Low Level Diode Laser Irradiation of Human Oral Mucosa Fibroblasts in Vitro", Lasers in Surgery and Medicine 14, pp. 347-354.

Logdberg-Anderson et al. (1997), "Low Level Laser Therapy (LLLT) of Tendonitis and Myofascial Pains: a Randomized, Double-blind, Controlled Study", Laser Therapy 9:79-86.

Kloth, Luther, et al. (1996), "Promotion of Wound Healing with Electrical Stimulation", The Journal for Prevention and Healing Advances 9(5).

Coldman, M.F., et al. (1969), "Enhanced of Percutaneous Adsorption by the Use of Volatile: Nonvolatile Systems as Vehicles", Journal of Pharmaceutical Sciences vol. 58, #9.

Hrnjak, M., et al. (Nov. 1995), "Stimulatory Effect of Low-Power Density He—Ne Laser Radiation on Human Fibroblast in Vitro", Vojnosanit Pregl. 52(6), pp. 539-546.

Callam, M. J., et al. (Jul. 1987),"A Controlled Trial of Weekly Ultrasound Therapy in Chronic Leg Ulceration", The Lancet, 204-206.

Pogrel, M., et al. (1997),"Effects of Low-Energy Gallium-Aluminum-Arsenide Laser Irradiation on Cultured Fibroblasts Keratincytes", Lasers in Surgery and Medicine 20, pp. 426-432.

Weiner, M., et al. (1994), Liposomes: A Novel Topical Delivery System for Pharmaceutical and Cosmetic Journal of Drug Targeting 2, pp. 405-410.

Dyson, Mary (Sep. 1982), "Stimulation of Tissue Repair by Therapeutic Ultrasound", Infections in Surgery 1(2), pp. 37-94.

Dyson, Mary, et al. (Apr. 1978), "Stimulation of Tissue Repair by Ultrasound: A Survey of the Mechanisms Involved", 64(4), pp. 105-108.

McDaniel (May 2001), "Nonablative Skin Rejuvenation—The Wave of the Future", Cosmetic Surgery Times.

McDaniel, D. H., et al. (1996), "Treatment Of Stretch Marks With The 585 Nm Flashlamp-Pumped Pulsed Dye Laser", 22(4), pp. 332-337.

Menezes et al. (Oct. 1998), "Non-Coherent Near Infrared Radiation Protects Normal Human Dermal Fibroblasts Solar Ultraviolet Toxicity", The Journal of Investigative Dermatology 111(4):629-633.

Monfrecola, G., et al (1987), "Topical Hematoporphyrin Plus UVA for Treatment of Alopecia Areata", Photodermatology.

Lehman, P. et al. (1991), "Effects of Ultraviolet A and B on the Skin Barrier: A Functional Electron Microscopic and Lipid Biochemical Study", Photodermatol Photoimmunol Photomed. 8, pp. 129-134.

Morganti, P., et al. (1997), "Enhancing the Glycolic Acid Efficacy by Piezoelectric Vibrations," J. Appl. Cosmotol. vol. 15, pp. 147-159.

Singh, Parminder, et al. (1993), "Iotophoretic Transdermal Delivery of Salicylic Acid and Lidocaine to Local Subcutaneous Structures", Journal of Pharmaceutical Sciences 82(2), pp. 127-131.

Parrish et al. (1981), "Action Spectrum for Phototherapy of Psoriasis," Journal of Investigative Dermatology 76 (5):359-361.

De Deyne, Patrick G., et al. (Jul. 1995), "In Vitro Effects of Therapeutic Ultrasound on the Nucleus of Human Fibroblasts", Physical Therapy 75(7), pp. 629-634.

Scheuplein, Robert ,et al. (1971), "Permeability of the Skin", Physiological Review, vol. 51, No. 4.

Polo, et al. (1999), "Role of Ground and Excited Singlet State Ozygen in the Red Light-Induced Stimulation of *Escherichia coli* Cell Growth", Biochemical and Biophysical Research Communications 257, pp. 753-758.

Potinen et al. (1996), "The Effect of Hair Lasers on Skin Blood Flow, Acupuncture & Electrotherapeutic", Res. Int. J., vol. 21, pp. 105-118.

Brucks, Richard, et al. (1989), "The Effect of Ultrasound on the in Vitro Penetration of Ibuprofen Through Human Epidermis", Pharmaceutical Research 6(8), pp. 697-701.

Borelli, S. (1955), "Chlorophyll in the Treatment 1-27 of Acne Vulgaris", Dematologie, Venerologie, and Verwandte Gebiete 6(7), pp. 320-324.

Mordon, S., et al (1997), "Thermal Damage Assessment of Blood Vessels in a Hamster Skin Flap Model by Fluorescence Measurement of a Liposome-Dye System", Lasers in Surg. & Med. 20, pp. 131-141.

Mordon, S., et al. (1997), "Selective Laser Photocoagulation of Blood Vessets in a Hamater Skin Flip Model using a Specific ICG Formulation", Lasers Surg. Med. 21(4), pp. 365-373.

Sakurai et al. (2000), "Inhibitory effect of low-level laser irradiation on LPS-stimulated prostaglandin E2 production and cyclooxygnase-2 in human gingival fibroblasts", in Er. J. Oral. Sci., Issue 108:pp. 29-34.

Schindl et al. (Sep. 2000), "Low-Intensity Laser Therapy: A Review", Journal of Investigative Medicine, 48(5).

(56) References Cited

OTHER PUBLICATIONS

Schul et al. (2002), "Enhanced repair of cyclobutane pyrimidine dimmers and improved UV resistance in photolyase transgenic mice", The European Molecular Biology Organization (EMBO) Journal 21(17):4719-4729.
ScienceDaily "2002 Nobel Prize in Physiology Or Medicine: Programmed Cell Death," dated Oct. 8, 2002, located at http://mm.sciencedaily.com/releases/2002/10/021008064740.htm Retrieved on Oct. 24, 2007. (5 pages).
Shalita et al., (2001), "Acne PhotoClearing (APC) Using a Novel, High-Intensity, Enhanced, Narrow-Band, Blue Light Source", Clinical Application Notes 9(1).
Pinnell, Sheldon (1985), "Regulation of Collagen Biosynthesis of Ascorbic Acid: A Review" The Yale Journal of Biology and Medicine 58, pp. 553-559.
Tajima, Shingo, et al. (1996), "Ascorbic Acid Preferentially Enhances Type I and III Collagen Gene Transcription in Human Skin Fibroblasts", J. Dermatol. Sci. 11(3), pp. 250-253.
Schaefer, Hans, et al. (1996), "Skin Barrier Principles of Percutaneous Absorption", pp. 153 and 175.
Skinner et al., (1996), "A Preliminary Study of the Effects of Laser Radiation on Collagen Metabolism in Cell Culture", Australian Dental Journal 41(3), pp. 188-192.
Sommer et al. (2001), "Biostimulatory Windows in Low-Intensity Laser Activation: Lasers, Scanners and NASA's Light Emitting Diode Array System", Journal of Clinical Laser Medicine & Surgery 19(1), pp. 29-33.
Sroka et al. (1999), "Effects on the Mitosis of Normal and Tumor Cells Induced by Light Treatment of Different Wavelengths", Lasers in Surgery and Medicine 25, pp. 263-271.
Sumiana et al., (1999)"A New Method to Improve Penetration Depth of Dyes into the Follicular Duct: Potential Application for Laser Hair Removal", J. Am. Acad. Dermatol. 41(2), pp. 172-175.
Melo, T. B.(1987), "Uptake of Protoporphyrin and Violet Light Photodestruction of Propionibacterium acnes", Journal of Biosciences 42(1-2), pp. 123-128.
Phillips, Charlotte, et al. (1994), "Effects of Ascorbic Acid on Profileration and Collagen Synthesis in Relation to the Donor Age of Human Dermal Fibroblasts", The Journal of Investigative Dermatology, vol. 103, No. 2.
Srinivasan, V., et al. (1989), "Transdermal Iontophoretic Drug Delivery: Mechanistic Analysis and Application to Polypeptide Delivery", Journal of Pharmaceutical Sciences 78(5).
Final Office Action dated Dec. 9, 2011 for U.S. Appl. No. 12/753,207.
Response to Final Office Action dated Dec. 9, 2011 for U.S. Appl. No. 12/753,207.
Notice of Restriction dated Mar. 29, 2006 for U.S. Appl. No. 10/665,390.
Response to Restriction dated Mar. 29, 2006 for U.S. Appl. No. 10/665,390.
Non Final Rejection dated Aug. 21, 2006 for U.S. Appl. No. 10/665,390.
Non Final Rejection dated Jan. 5, 2006 for U.S. Appl. No. 10/903,483.
Amendment to Non-Final Rejection dated Jan. 5, 2006 for U.S. Appl. No. 10/903,483.
Non Final Rejection dated Sep. 25, 2006 for U.S. Appl. No. 10/903,483.
Amendment to Non-Final Rejection dated Sep. 25, 2006 for U.S. Appl. No. 10/903,483.
Non Final Rejection dated May 22, 2008 for U.S. Appl. No. 10/903,483.
Non Final Rejection dated Jul. 18, 2007 for U.S. Appl. No. 11/205,316.
Amendment to Non-Final Rejection dated Jul. 18, 2007 for U.S. Appl. No. 11/205,316.
Final Rejection dated Jun. 9, 2008 for U.S. Appl. No. 11/205,316.
Non Final Rejection dated Oct. 19, 2007 for U.S. Appl. No. 11/272,042.
Amendment to Non-Final Rejection dated Oct. 19, 2007 for U.S. Appl. No. 11/272,042.
Final Rejection dated Jun. 6, 2008 for U.S. Appl. No. 11/272,042.
Non-Final Rejection dated Jun. 8, 2010 for U.S. Appl. No. 12/583,562.
Amendment to Non-Final Rejection dated Jun. 8, 2010 for U.S. Appl. No. 12/583,562.
Official Notification dated Dec. 3, 2008 for Israeli Patent Application No. 171311.
Official Notification dated Nov. 19, 2009 for Israeli Patent Application No. 171311.
Response to Official Notification dated Nov. 19, 2009 for Israeli Patent Application No. 171311.
First Office Action dated Mar. 10, 2006 for Chinese Patent Application No. 200480012575.X.
Response to First Office Action dated Mar. 10, 2006 for Chinese Patent Application No. 200480012575.X.
Second Office Action dated Nov. 2, 2007 for Chinese Patent Application No. 200480012575.X.
Notice of Reexamination dated Jul. 27, 2010 for Chinese Patent Application 200480012575.X.
Response to Notice of Reexamination dated Jul. 27, 2010 for Chinese Patent Application No. 200480012575.X.
Official Notification regarding clarification of claims dated Sep. 19, 2002 for PCT Patent Application No. PCT/US02/26627.
Request for Rectification of Obvious Errors in the International Patent Application and Submission of Request to Record Change of Agent's Address dated Sep. 27, 2002 for PCT Patent Application No. PCT/US02/26627.
International Search Report dated May 16, 2003 for PCT Patent Application No. PCT/US02/26627.
Written Opinion dated Feb. 5, 2004 for PCT Patent Application No. PCT/US02/26627.
International Search Report dated May 8, 2003 for PCT Patent Application No. PCT/US02/35839.
International Preliminary Examination Report dated Oct. 7, 2003 for PCT Patent Application No. PCT/US02/35839.
First Statement of Proposed Amendments dated Oct. 27, 2005 for Australian Patent Application No. 2002326716.
Examiners Report dated Mar. 22, 2007 for Australian Patent Application No. 2002326716.
Office Action dated Aug. 2, 2006 for Canadian Patent Application No. 2457590.
Response to Office Action dated Aug. 2, 2006 for Canadian Patent Application No. 2457590.
Office Action dated Apr. 30, 2007 for Canadian Patent Application No. 2457590.
Response and Amendment to Office Action dated Apr. 30, 2007 for Canadian Patent Application No. 2457590.
Office Action dated Jan. 31, 2008 for Canadian Patent Application No. 2457590.
Request for Reinstatement for Failure to Respond to Office Action dated Jan. 31, 2008 for Canadian Patent No. 2457590.
Office Action dated Oct. 2, 2009 for Canadian Patent Application No. 2457590.
Response to Office Action dated Oct. 2, 2009 for Canadian Patent Application No. 2457590.
Office Action dated Dec. 30, 2010 in Canadian Patent Application No. 2,457,590.
Office Action dated May 6, 2010 in Canadian Patent Application No. 2,457,590.
Response to Office Action dated May 6, 2010 in Canadian Patent Application 2,457,590.
Office Action dated Aug. 25, 2006 for European Patent Application No. 02761449.4-1216.
Response to Office Action dated Aug. 25, 2006 for European Patent Application No. 02761449.4-1216.
Office Action dated Jul. 31, 2007 for European Patent Application No. 02761449.4-1216.
Response to Office Action dated Jul. 31, 2007 for European Patent Application No. 02761449.4-1216.
Preliminary Amendment dated Feb. 15, 2001 for U.S. Appl. No. 09/819,083.

(56) References Cited

OTHER PUBLICATIONS

Non-Final Rejection dated Feb. 19, 2003 for U.S. Appl. No. 09/819,083.
Amendment to Non-Final Rejection dated Feb. 19, 2003 for U.S. Appl. No. 09/819,083.
Preliminary Amendment dated May 2, 2005 for U.S. Appl. No. 11/119,378.
Non-Final Rejection dated Jun. 5, 2006 for U.S. Appl. No. 11/119,378.
Amendment to Non-Final Rejection dated Jun. 5, 2006 for U.S. Appl. No. 11/119,378.
Preliminary Amendment dated Aug. 29, 2005 for U.S. Appl. No. 11/212,916.
Non-Final Rejection dated Sep. 25, 2007 for U.S. Appl. No. 11/212,916.
Amendment to Non-Final Rejection dated Sep. 25, 2007 for U.S. Appl. No. 11/212,916.
Final Rejection dated Mar. 25, 2008 for U.S. Appl. No. 11/212,916.
Non-Final Rejection dated Jun. 19, 2008 for U.S. Appl. No. 11/332,517.
Non-Final Rejection dated Dec. 19, 2002 for U.S. Appl. No. 09/986,367.
Amendment to Non-Final Rejection dated Dec. 19, 2002 for U.S. Appl. No. 09/986,367.
Final Rejection dated Aug. 12, 2003 for U.S. Appl. No. 09/986,367.
Amendment to Final Office Action dated Aug. 12, 2003 for U.S. Appl. No. 09/986,367.
Advisory Action dated Mar. 8, 2004 for U.S. Appl. No. 09/986,367.
Non-Final Rejection dated Sep. 22, 2004 for U.S. Appl. No. 09/986,367.
Amendment to Non-Final Rejection dated Sep. 22, 2004 for U.S. Appl. No. 09/986,367.
Non-Final Rejection dated Jun. 26, 2008 for U.S. Appl. No. 11/366,811.
Non-Final Rejection dated Jun. 25, 2008 for U.S. Appl. No. 11/346,622.
Amendment to Non-Final Rejection dated Jun. 25, 2008 for U.S. Appl. No. 11/346,622.
Final Office Action dated Jan. 6, 2010 for U.S. Appl. No. 11/346,622.
Response to Final Office Action dated Jan. 6, 2010 for U.S. Appl. No. 11/346,622.
Advisory Action dated Mar. 12, 2010 for U.S. Appl. No. 11/346,622.
U.S. Office Action dated Sep. 30, 2010 for U.S. Appl. No. 11/346,622.
Response to U.S. Office Action dated Sep. 30, 2010 for U.S. Appl. No. 11/346,622.
U.S. Final Office Action dated Jun. 13, 2011 for U.S. Appl. No. 11/346,622.
Response to U.S. Final Office Action dated Jun. 13, 2011 for U.S. Appl. No. 11/346,622.
Amendment to Non-Final OA dated Sep. 22, 2009 for U.S. Appl. No. 11/116,434.
Final Rejection dated Sep. 15, 2010 for U.S. Appl. No. 11/116,434.
Response to Final Office Action dated Sep. 15, 2010 for U.S. Appl. No. 11/116,434.
Advisory Action dated Dec. 22, 2010 for U.S. Appl. No. 11/116,434.
Appeal Brief dated Aug. 15, 2011 for U.S. Appl. No. 11/116,434.
U.S. Office Action dated May 10, 2011 for U.S. Appl. No. 12/550,749.
Response to Office Action dated May 10, 2011 for U.S. Appl. No. 12/550,749.
Final Office Action dated Jan. 18, 2012 for U.S. Appl. No. 12/550,749.
Response to Final Office Action dated Jan. 18, 2012 for U.S. Appl. No. 12/550,749.
U.S. Office Action dated May 11, 2011 for U.S. Appl. No. 12/550,799.
Response to Office Action dated May 11, 2011 for U.S. Appl. No. 12/550,799.
Final Office Action dated Dec. 3, 2012 for U.S. Appl. No. 12/550,799.
U.S. Office Action dated Mar. 30, 2011 for U.S. Appl. No. 12/550,464.
Response to Office Action dated Mar. 30, 2011 for U.S. Appl. No. 12/550,464.
U.S. Office Action dated Oct. 28, 2011 for U.S. Appl. No. 12/550,464.
Response to Office Action dated Oct. 28, 2011 for U.S. Appl. No. 12/550,464.
Final Office Action dated May 29, 2012 for U.S. Appl. No. 12/550,464.
Response to Final Office Action dated May 29, 2012 for U.S. Appl. No. 12/550,464.
U.S. Office Action dated May 25, 2011 for U.S. Appl. No. 12/753,207.
Non-Final Rejection dated Sep. 22, 2009 for U.S. Appl. No. 11/116,434.
Response to Final Office Action dated Jan. 5, 2009 for U.S. Appl. No. 11/116,434.
Final Rejection dated Jan. 5, 2009 for U.S. Appl. No. 11/116,434.
Amendment to Non-Final Rejection dated Feb. 20, 2008 for U.S. Appl. No. 11/116,434.
Non-Final Rejection dated Feb. 20, 2008 for U.S. Appl. No. 11/116,434.
Amendment to Final Office Action dated Jun. 29, 2007 for U.S. Appl. No. 11/116,434.
Final Rejection dated Jun. 29, 2007 for U.S. Appl. No. 11/116,434.
Amendment to Non-Final Rejection dated Jan. 9, 2007 for U.S. Appl. No. 11/116,434.
Non-Final Rejection dated Jan. 9, 2007 for U.S. Appl. No. 11/116,434.
Response to Miscellaneous Action Regarding Drawing Inconsistency dated Aug. 24, 2005 for U.S. Appl. No. 09/876,157.
Miscellaneous Action Regarding Drawing Inconsistency dated Aug. 24, 2005 for U.S. Appl. No. 09/876,157.
Amendment to Non-Final Rejection dated Apr. 8, 2004 for U.S. Appl. No. 09/876,157.
Non-Final Rejection dated Apr. 8, 2004 for U.S. Appl. No. 09/876,157.
Response to Restriction Requirement dated Jul. 22, 2003 for U.S. Appl. No. 09/876,157.
Requirement for Restriction/Election dated Jul. 22, 2003 for U.S. Appl. No. 09/876,157.
Preliminary Amendment dated Jan. 7, 2002 for U.S. Appl. No. 09/876,157.
Amendment to Final Office Action dated Jan. 25, 2008 for U.S. Appl. No. 11/783,538.
Final Rejection dated Jan. 25, 2008 for U.S. Appl. No. 11/783,538.
Amendment to Non-Final Rejection dated Aug. 22, 2007 for U.S. Appl. No. 11/783,538.
Non-Final Rejection dated Aug. 22, 2007 for U.S. Appl. No. 11/783,538.
Non-Final Rejection dated Dec. 30, 2005 for U.S. Appl. No. 09/819,082.
Preliminary Amendment dated Feb. 15, 2001 for U.S. Appl. No. 09/819,082.
Amendment After Notice of Allowance dated Aug. 1, 2008 for U.S. Appl. No. 09/819,083.
Amendment to Final Office Action dated Jan. 24, 2008 for U.S. Appl. No. 09/819,083.
Final Rejection dated Jan. 24, 2008 for U.S. Appl. No. 09/819,083.
Amendment to Non-Final Rejection dated May 15, 2007 for U.S. Appl. No. 09/819,083.
Non-Final Rejection dated May 15, 2007 for U.S. Appl. No. 09/819,083.
Amendment to Final Office Action dated Dec. 22, 2006 for U.S. Appl. No. 09/819,083.
Final Rejection dated Dec. 22, 2006 for U.S. Appl. No. 09/819,083.
Amendment to Non-Final Rejection dated Mar. 24, 2006 for U.S. Appl. No. 09/819,083.

(56) References Cited

OTHER PUBLICATIONS

Non-Final Rejection dated Mar. 24, 2006 for U.S. Appl. No. 09/819,083.
Advisory Action dated Dec. 1, 2005 for U.S. Appl. No. 09/819,083.
Amendment to Final Office Action dated Sep. 1, 2005 for U.S. Appl. No. 09/819,083.
Final Rejection dated Sep. 1, 2005 for U.S. Appl. No. 09/819,083.
Amendment to Non-Final Rejection dated Dec. 15, 2004 for U.S. Appl. No. 09/819,083.
Non-Final Rejection dated Dec. 15, 2004 for U.S. Appl. No. 09/819,083.
Amendment to Non-Final Rejection dated Jan. 14, 2004 for U.S. Appl. No. 09/819,083.
Non-Final Rejection dated Jan. 14, 2004 for U.S. Appl. No. 09/819,083.
Heikkila, H.. Stubb, S., & Kiistala, U (1996). "Nail growth measurement employing nail indentation—an experimental follow-up study of nail growth in situ," Clinical and Experimental Dermatology, 21(2). pp. 96-99.
Zimny, S., & Pfohl, M. (2005). "Healing times and prediction of wound healing in neuropathic diabetic foot ulcers: a prospective study," Experimental and Clinical Endocrinology & Diabetes, 113(2). pp. 90-93.
Martinez, D., et al. (2001). "Wound healing response of the medial collateral ligament during hindlimb unweighting in young rats.".
Rosenburg, L. (2003). Wound healing, growth factors, Emedicine.
Mitragotri, S. (2000). "Synergistic effect of enhancers for transdermal drug delivery," Pharmaceutical Research, 17(11). pp. 1354-1359.
Mitragotri, S., et al. (2000). "Analysis of ultrasonically extracted interstitial fluid as a predictor of blood g levels," Journal of Applied Physiology, 89(3). pp. 961-966.
Anvar, M.D., et al.(2000). "Vascular and stromal features in the skin of the lower limb in patients with critical limb ischaemia," European Journal of Vascular and Endovascular Surgery, 20(2). pp. 125-131.
Eichler, W., et al. (2000). "Changes of interstitial fluid volume in superficial tissues detected by a miniature ultrasound device," Journal of Applied Physiology, 89)1). pp. 359-363.
Mitragotri, S., et al. (2000), "Transdermal extraction of analytes using low-frequency ultrasound," Pharmaceutical Research, 17(4). pp. 466-470,.
Moli, M. et al, (2000). "Two children with suspected primary vasculitis of messenteric vessels—a case report," Nihon Rinsho Meneki Gakkai Kaishi, 23(2). pp. 148-155.
Mitragotri, S., et al. (2000). "Synergistic effect of low-frequency ultrasound and sodium lauryl sulfate on transdermal transport," Journal of Pharmaceutical Science, 89(7). pp. 892-900.
Mitragotri, S,, & Kost, J. (2000), "Low-frequency sonophoresis: A noninvasive method of drug delivery and diagnostics," Biotechnology in Progress, 16(3), pp. 488-492.
Taylor, B.K., et al. (2000). "Opioid inhibition of formalin-induced changes in plasma extravasation and blood flow in rats," PAIN, 84(2-3). pp. 263-270.
Fang, J., et al. (1999). "Effect of low-frequency ultrasound on the in vitro percutaneous absorption of clobetasol 17-propionate," International Journal of Pharmaceutics, 191(1). pp. 33-42.
Shoab, S.S,, et al. (1999). "Plasma VEGF as a marker of therapy in patients with chronic venous diseases with oral micronised flavonoid fraction- a pilot study," European Journal of Vascular and Endovascular Surgery, 18(4). pp. 334-338.
Meidan, V.M., et al. (1999). "Ultrasound-enhanced diffusion into coupling gel during phonophoresis of 5-fluorouracil," International Journal of Pharmaceutics, 185(2). pp. 205-213.
Terai, M., et al. (1999). "Vascular endothelial growth factor in acute Kawasaki disease," American Journal of Cardiology, 83(3). pp. 337-339.
Singer, A.J., et al. (1999). "The effects of low-frequency ultrasound on *Staphylococcus epidermidis*," Microbiology, 38(3). pp. 194-196.

Foldvari, M., et al. (1998). "Liposome encapsulated prostaglandin EI in erectile dysfunction: Correlation in vitro delivery through foreskin and efficacy in patients," Urology, 52(5). pp. 838-843.
Wu, J., et al. (1998). "Defects generated in human stratum corneum specimens by ultrasound," Ultrasound in Medicine and Biology, 24(5). pp. 705-710.
Liu, J., Lewis, T.N., & Prausnitz, M.R. (1998) "Non-invasive assessment and control of ultrasound-mediated membrane permeabilization," Pharmaceutical Research, 15(6). pp. 918-924.
Pedder, V.V., et al. (1998). "Rationale of noninvasive method of drug administration at the prelymphatic," MED TEKH, pp. 18-23.
.Sigfridsson et al. (1995),"Electrogenetic light reactions in photsystem I: resolution of electron-transfers rates between the iron-sulfer centers," Proc. National Acadamy of Science U.S.A., pp. 3456-3462. (Abstract).
Voigt et al. (2002), "Spectral Substructure and Excitonic Interactions in the Minor Photosystem II Antenna Complex CP29 Revealed by Nonlinear Polarization Spectroscopy in Frequency Domain," Biochemistry, pp. 3049-3056. (Abstract).
Dacher et al. (2001), "Combinded NPLC-MS and HPLC-NMR on-line coupling for the separation and determination of lutein and zeaxanthin stereoisomers in spinach and in retina," Analytical Chemistry, pp. 667-674. (Abstract).
Varani et al. (2001), "Inhibition of type I procollagen synthesis by damages collagen in photoaged skin and by collagenase-degraded collagen in vitro," American Journal of Pathology, pp. 931-941. (Abstract).
Yu et al. (1997), "Photomodulation of oxidative metabolism and electron chain enzymes in rat liver mitochondria," Photochem. Photobiol pp. 866-871. (Abstract).
Quan et al. (2002), "Connective tissue growth factor: expression in human skin in vivo and inhibition by ultraviolet radiation," Journal of Investigative Dermatology, pp. 402-408. (Abstract).
Boudjelal et al. (2002), "Retinoid Signaling Is Attenuated by Protassome-Mediated Degradation of Retinoid Receptors in Human Keratinocyte HaCaTCells," Exp. Cell. Res., pp. 130-137. (Abstract).
Loschinger et al. (1998), "Stimulation of protein kinase A activity and induced terminal differentiation of human skin fibroblasts in culture by low-frequency electromagnetic fields," Toxicol. Lett., pp. 369-376. (Abstract).
Bourguignon, GJ. and Bourguignon, LY. (1987), "Electric stimulation of protein and DNA synthesis in human fibroblasts," PASBERS J., pp. 398-402. (Abstract).
Quan et al. (2001), "Ultraviolet irradiation blocks cellular responses to transforming growth factor-beta by down-its type-II receptor and inducing Smad7," Journal of Biological Chemistry, pp. 26349-26356, (Abstract).
Neudecker, BA., et al. (2004) "Abberant Serum Hyaluronan and Hyaluronidase Levels In Scleroderma," The British Journal of Dermatology pp. 469-476.
Formby, Bent, et al. (2002) "Lactate Stimulates Hyaluronan and CD44 Expression in Cultured Fibroblasts: the Warburg Effect Revisited," Experimental Cell Research May 15, 2002;276(1).24-31.
Stern, Robert. (2001) "Minireview on the Mammalian Hyaluronidases: Introductory Remarks" pub. By Elsevier Science B.V., Matrix Biology p. 497.
Csoka, Antonei, B. (2001) "Minireview The Six Hyaluronidase-like Genes in Human and Mouse Genomes" pub. by Elsevier Science B.V., Matrix Biology pp. 499-508.
Boh, Erin E. (2001) "Free Radicals and Aging Skin" Cosmetic Dermatology vol. 14 No. 12 Dec. 2001 pr. 37-40.
Lubart, R. et al, (1992) "Effect of Light on Calcium Transport in Bull Sperm Cells" Journal of Photochemistry Photobiology B. Sep. 15, 1992;15(4):337-41.
Webster, Guy (2001). "Acne Pathogenesis & update on Therapy" Jujisawa Healthcare, Inc. Lectureship Series in Dermatology [pamphlet] pp. 1-24.
Loschinger, Monika (1998). "Stimulation of Protein Kinase A Activity and Induced Terminal Differentiation of Human Skin Fibroblasts in Culture by Low-Frequency Electromagnetic Fields" Toxicol Lett. Aug. 1998; pp. 96-97:369-376.

(56) References Cited

OTHER PUBLICATIONS

Bedi, Monika K (2002) "Herbal therapy in dermatology" Archives of Dermatology Feb. 2002 pp. 138(2):232-242.
Yu, Wei. (1997). "Photomodulation of Oxidative Metabolism and electron Chain Enzymes in Rat Liver Mitochondria" Photochemistry and Photobiology. Dec. 1997,66(6):866-71.
Barber, James (2002) "Short communication' P680 What is it and Where is it?" Bioelectrochemistry, vol. 55. No. 1, Jan. 2002, pp. 135-138(4).
Matsuad, Tatsuru et al. (2002) "Biosynthesis and distribution of Chlorophyll Among the Photosystems During recovery the Green Alga Dunaliella Salina From Irradiance Stress" Plant Physiology. Feb. 2002;128(2):603-14.
De Mattei, M, et al. (2001) "Effect of Pusled Electromagnetic Fields on human Articular Chodrocyte Proliferation" Connective Tissue Research 2001;42(4):269-79.
Krishtalik, Li et al. (2000) "Effects of Medium Polarization and Pre-Existing Field on Activation Energy of Enzymatic Charge-Transfer Reactions" Biochimica Biophysica Acta. Jul. 20, 2000;1459(1):88-105.
Edwards, AM, Silva, E. "Effect of Visible Light on Selected Enzymes, Vitamins and Amino Acids" Journal of Photochemistry Photobiology B. Oct. 2001:63(1-3):126-31.
Sommer, Andrei P. "Abstracts From the 1st International workshop on Nearfield Optical Analysis. Reisenberg, Germany, Nov. 2000" Journal of Clinical Laser Medicine & Surgery vol. 19 No. 2 2001.
Ishigaki, Y., et al. (1999). "Development and Characterization of a DNA Solar Dosimeter," Journal of Photochemistry and Photobiolgy, 50. pp. 184-188.
Gross, A. (1999). "Entering the Japanese Medical Device Market: The latest trends mean even better opportunities for medical technology manufacturers," Medical Devicelink, Accessed: Dec. 15, 2001.
Gross, A., & Dyson, P. (1996). "Changing Regulatory Climate Improves Korean Market of U.S. Companies," Medical Device and Diagnostic Industry.
LeDoux, S,P., & Wilson, G.L. (2001). "Base Excision Repair of Mitochondria! DNA Damage in Mammalian Cells," in Nucleic Acid Research and Molecular Biology, 66. pp. 273-284.
Turnbull, D., & Lightowlers, R. (2001). "Might Mammalian Mitochondria Merge?" Nature Medicine, 7(6). pp. 895-896.
Nakada, K., et al. (2001). "Inter-mitochondria) complementation: Mitochondria-specific system preventing mice from of disease phenotypes by mutant mtDNA," Nature Medicine, 7(8), pp. 934-940.
Vogel, W.F. (2001) "Collagen-receptor signaling in health and disease," European Journal of Dermatology, 11(6). pp. 506-514.
Curat, C. et al, (2001) "Mapping of eptiopes in discoidin domain receptor 1 critical for collagen binding," Journal of Biological Chemistry, 6(49).
Hou, G., Vogel, W, & Bendeck, M.P, (2001). The discoidin domain receptor tyrosine kinase DOR1 in arterial wound repair, Journal of Clinical Investigation, 107(61. pp. 727-735.
Chin, G.S., et al. (2000). "Cellular signaling by tyrosine phosphorylation in keloid and normal human dermal fibroblasts," Plastic Reconstructive Surgery, 106(7). pp, 1532-1540.
Weiner, H.L., et al. (2000). "Consistent and selective expression of the discoidin domain receptor-1 tyrosine kinase in human brain tumors," Neurosurgery, 47(6). pp. 1400-1409.
Chin, G.S., et al. (2000). "Differential expression of receptor tyrosine kinases and She in fetal and adult rat fibroblasts: Toward defining scarless versus scarring fibroblast phenotypes," Plastic Reconstructive Surgery, 105(3). pp. 972-979.
Vogel, W., et al. (2000). "Discoidin domain receptor 1 is activated independently of beta 1 integrin," Journal of Biological Chemistry 275(8). pp. 5779-5784.
Vogel, W. (1999). " Discoidin domain receptors: Structural relations and functional implications, " FASEB Journal, 13. pp. 77-82.
Norman, J.T., & Fine, L.G. (1999). "Progressive renal disease: Fibroblasts, extracellular matrix, and integrins," Experimental Nephrology, 7(2), pp. 167-177.
Shrivastava, A., et al. (1997). "An orphan receptor tyrosine kinase family whose members serve as nonintegrin collagen receptors," Molecular Cell, 1(1). pp. 25-34.
Vogel, W., et al. (1997). "The discoidin domain receptor tyrosine kinases are activated by collagen, " Molecular Cell, 1 (1). pp. 13-23.
Sakuma, S., et al. (1996). "Receptor protein tyrosine kinase DOR is up-regulated by p53 protein," FEBS Letters, 2. pp. 398, 165-169.
Hardell, L., et al. (2001). " Ionizing radiation, cellular telephones and the risk for brain tumors, " European Journal of Cancer Prevention, 10(6). pp. 523-529.
Seishima, M., Oyama, Z.. & Yarnamura, M. (2002). "Cellular phone dermatitis," Archives of Dermatology, 138(2). pp. 272-273.
Di Carlo, A., et al. (2002). "Chronic electromagnetic field exposure decreases HSP70 levels and lowers cytoprotection," Journal of Cellular Biochemistry, 84(3). pp. 447-454.
French, P.W., et al. (2001). " Mobile phones, heat shock proteins and cancer," Differentiation, 67(4-5), pp. 93-97.
Frumkin, H., et al. (2001). "Cellular phones arid risk of brain tumors," CA: A Cancer Journal for Clinicians, 51(2). pp. 137-141.
Moustafa, Y.M., et al. (2001). "Effects of acute exposure to the radiofrequency fields of cellular phones on plasma lipid peroxide and antioxidase activities in human erythrocytes, "Journal of Pharmaceutical and Biomedical Analysis, 26(4). pp. 605-608.
Chiladakis, J.A., et al. (2001). "In-vivo testing of digital cellular telephones in patients with implantable cardioverter-defibrillators," European Heart Journal, 22(15). pp. 1337-1342.
Santini, R., et al. (2001). "Symptoms reported by mobile cellular telephone users." Pathological Biology, 49(3). pp. 222-226.
Roti, J.L., et al. (2001). "Neoplastic transformation in C3H 10T(1/2) cells after exposure to 835.62 MHz FDMA and 847.74 CDMA radiations," Radiation Research, 155(1-2). pp. 239-247.
Wainwright, P. (2000). "Thermal effects of radiation from cellular telephones," Physics in Medicine and Biology, 152 (3). pp. 293-302.
Adey, W.R., et al. (1999). "Spontaneous and nitrosourea-induced primary tumors of the central nervous system in Fischer 344 rats chronically exposed to 836 MHz modulated microwaves," Radiation Research, 152(3). pp. 293-302.
Robert, E. (1999). "Intrauterine effects of electromagnetic fields- (low frequency, mid-frequency RF, and microwave): A review of epidemiologic studies," Teratology. 59(4). pp. 292-298.
De Seze, R.. Fabbro-Peray, P., & Miro, L. (1998), "GSM radlocellular telephones do not disturb the secretion of antepituitary hormones in humans," Bioetectrornagnetics, 19(5), pp. 271-278.
Malyapa, R S., et al. (1997). "Measurement of DNA damage after exposure to electromagnetic radiation in the cellular phone communication frequency band (835.62 and 847.74 MHz)," Radiation Research, 148(6). pp. 618-627.
Litovitz, TA., et al.(1997). "Bioeffects induced by exposure to microwaves are mitigated by superposition of ELF noise," Bioelectromagnetics, 18(6). pp. 422-430.
Omura, Y., & Losco, M. (1993). "Electro-magnetic fields in the home environment (color TV, computer monitor, microwave oven, cellular phone, etc) as potential contributing factors for the induction of oncogen C-fos Ab1, oncogen C-fos Ab2, integrin alpha 5 beta 1 and development of cancer, as well as effects of microwave on amino acid composition of food and living human brain," Acupuncture and Electro-Theraputics Research, 18(1). pp. 33-73.
Knave, B. (2001). "Electromagnetic fields and health outcomes," Annals Academy of Medicine Singapore, 30(5). pp. 489-493.
De Seze, R., et al. (1999). "Evaluations in humans of the effects of radiocellular telephones on the circadian patterns of melatonin secretion, a chronobiological rhythm marker," Journal of Pineal Research, 27(4). pp. 237-242.
Fluhr, J.W., et al, (1999). "In-vitro and in-vivo efficacy of zinc acetate against propionibacteria alone and in combination with erythromycin," Zentralbl Bakteriol, 289(4). pp. 445-456.
Koh, Y., et al. (2001). "Photodynamic therapy of acne vulgaris with topical delta-aminolaevulinic acid and incoherent light in Japanese patients," British Journal of Dermatology, 144(3). pp. 575-579.

(56) References Cited

OTHER PUBLICATIONS

Lang, K. et al. (2001). "Aminolevulinic acid: Pharmacological profile and clinical indication," Expert Opinion on Drug . Discovery, 10(6). pp. 1139-1156.
Ashmead, H.D, "The Need for Better Nutrition in our Food." Clearfield, Utah. USA. pp. 1-20.
Van Remmen, H. & Richardson, A. (2001). "Oxidative Damage to Mitochondria and Aging," Experimental Geology 36, pp. 957-968.
Rice, B.W., et al. (2001). "In Vivo Imaging of Light-emitting Probes," Journal of Biomedical Optics 6(4), pp. 432-440.
Moretti, M. (2001). "1CN Develops Integrated Skin Treatment Package," Aesthetic Buyers Guide Nov. 2001.
Neudecker, B.A., Stern, R., & Connolly, M.K. (2004), "Aberrant Serum Hyaluronan and Hyaluronidase Levels in Scteroderma," Department of Pathology and Dermatology, School of Medicine, University of California San Francisco.
Leyden, J. et al. (1999). "Finasteride in the Treatment of Men with Frontal Male Pattern Hair Loss," Journal of the American Academy of Dermatology 40(6). pp. 930-937.
Sommer, A.P, et al. (2001). "Biostimulatory Windows in Low-Intensity Laser Activation! Lasers, Scanners, and NASA's Light-Emitting Diode Array System," Journal of Clinical Laser Medicine and Surgery 19(1). pp. 29-33.
Troy, T. (2002). "Fluorescent Pulsed Light Makes Foray," Dermatology Times Jan. 2002.
Panteleyev, A., Jahoda, C., & Christiano, A. (2001). "Hair Follicle Predetermination," Journal of Cell Science 114. pp. 3419-3431.
Yoon, J.H., et al. (2000). "The DNA Damage Spectrum Produced by Simulated Sunlight," Academic Press, pp. 681-693.
Draper, B., et al. (2002). "MNPs and TIMP-1 are Differentially Expressed Between Acute Murine Excisional and Laser Wounds," Lasers in Surgery and Medicine 30, pp. 106-116.
Takemura et al.(1998), "Enhanced Interleukin 6 Production by Cultured Fibroblasts from Patients with Systemic Sclerosis in Response to Platelet Derived Growth," The Journal of Rheumatology, pp. 1534-1539.
Czuwara et al. (2001), "Differential regulation of transforming growth factor-It receptors type I and II by platelet-derived growth factor in human dermal fibroblasts," British Journal of Dermatology, 569-575.
Loftsson et al. (1995), "Fatty acids from cod-liver oil as skin penetration enhancers," Die Pharmazie, pp. 271-773.
Stahl et al. (2000), "Carotenoids and carotenoids plus vitamin E protect against unitraviolet light-induced erythema in humans," The American Clinical Journal of Nutrition, pp. 795-798.
Gambichler et al. (2001), "Ultraviolet protection by summer textiles. Ultraviolet transmission measurements verified by termination of the minimal erythema dose with solar simulated radiation," British Journal of Dermatology, pp. 484-489.
Stahl et al. (2001), "Dietary Tomato Pasta Protects against Ultraviolet Light-Induced Erythema in Humans," Biochemical and Molecular Action of Nutrients Research Communication, pp. 1449-1451.
Lee et al. (2000), "Carotenoid Supplementation Reduces Erythema in Human Skin After Simulated Solar Radiation Exposure," Society of Experimental Biology and Medicine, pp. 170-174.
Moy et al. (2000), "Incresed Glycosaminolycans Production in Sclersoing Basal Cell Carcinoma-Derived Fibrolasts and Stimulation of Normal Skin Ftbrolast Glycosaminoglycans Production by a Cytokine-Derived from Sclerosing Basal Cell Carcinoma," Dermatolgoic Surgery, pp. 1029-1035.
Takehara, K. (2000), "Grown regulation of skin fibroblasts," Journal of Dermatologial Science, pp. 70-74.
Loftsson, T (1989). "Effect of choline esters and oleic acid on the penetration of acyctovir, estradiol, hydrocortisone, nitroglycerin, retinoic acid and trifluorothymidine across hairless mouse skin in vitro," Acta. Pharm. Nord., pp. 279-286.
Masson et, al. (2000), "Marine lipids for prodrugs. soft compounds and other pharmaceutical applications," Pharmazie, pp. 172-177.

Gross et al. (1978), "Comprehensive compilation of empirical ultrasonic properties of mammalian tissues," Journal of the Acoustical Society of America, pp. 423-457.
Fei et al, (1986), "Ultrasonic backscatter from bovine tissues:Varation with pathology," Journal of the Acoustical Society of America, pp. 166-172.
Fei, D and Shung, K. (1986), "Ultrasonic backscatter from bovine tissues," Journal of the Acoustical Society of America, pp. 871-876.
Chivers, R. and Parry R.(1978), "Ultrasonic velocity and attenuation in mammalian tissues," Journal of the Acoustical Society of America, pp. 940-954.
De Weerd et al. (2002), "Pathways for Energy transfer in the Core Light Harvesting Complexes CP43 and CP 47 of Photosystem II," Biophysical Journal, pp. 1586-1597.
Fluhr et al. (1999), "In-vitro and in-vivo Efficacy of Zinc Acetate against Propionibacteria Alone and in Combination with Erythromycin," Zent. bl. Bakerologie, pp. 445-456.
Lang et al. (2001), "Aminolevulinic acid' pharmacological profile and clinical indication," Expert Opinion Investigative Drugs, pp. 1139-1156.
Yakushevska et al. (2001), "Supermolecular organization of photosystem II and its associated light-harvesting antenna in Arabidopsis thalinana," European Journal of Biochemistry, pp. 6020-6028.
Pollvka et al. (2002), "Carotenoid Si State in a Recombinant Light-Harvesting Complex of Photosystem II," Biochemistry, pp. 439-450.
Vander Meulen Meulen et al. (2002), "Calcium Depletion Modifies the Structure of the Photosystem II O2-Evolving Complex," Biochemistry, pp. 958-966.
Park et al.(2000), "Epidermal Growth (EGF) Antagonizes Transforming Growth Factor (TGF)-β1-induced Collagen Lattice Contraction by Human Skin Fibrolasts," Biological and Pharmaceutical Bulletin, pp. 1517-1520.
Diffey et al. (2000), "In vitro assessment of the broad-spectrum ultraviolet protection of sunscreen products," Journal of the American Academy of Dermatology, pp. 1024-1035.
Zhu et al. (1997), "Photo-Irradiation Improved Functional Preservation of the Isolated Rat Heart," Lasers in Surgery and Medicine, pp. 332-339.
Yu et al. (1997), "Improvement of Host Response to Sepsis by Photobiomodulation," Lasers in Surgery and Medicine, pp. 262-268.
Shapiro, J and Price, V. (1998), "Hair Regrowth: Therapeutic Agents," Dermatologic Therapy, pp. 341-356.
El Sayed, S and Dyson, M. (1990), "Comparision of the Effect of Multiwavelength Light Produced by a Cluster of Semiconductor Diodes and of Each Individual Diode on mast Cell Number and Degranulation in Intact and Injured Skin," Lasers in Surgery and Medicine, pp. 559-568.
Huang et al. (2002), "Two-Photon Fluorescence Spectroscopy and Microscopy of NAD(P)H and Flavoprotein," Biophysical Journal, pp. 2811-2825.
Yamazaki et al. (1992), "Slecetive Chemical Modification of Amino Acid Residues in the Flavin Adrenie Dinucleotide . Binding Site of Nadph-Ferredoxin Reductase," Interntemational Journal of Biochemistry, pp. 223-228.
Andersson et al. (1998), "Autoftuoresence of living cells," Journal of Microscopy, pp. 1-7.
Cheri et al. (2002), "New Technology for Deep Light Distribution in Tissue for Phototherapy," The Cancer Journal, pp, 154-163.
Baena-Gonzalez et al. (2001), "Cloroptast Transcription at Different Light Intensities. Glutathione-Mediated Phosphorylation of the Major RNA Polymerase Involved in Redox-Regulated Organellar Gene Expression," Plant Physiology, pp. 1044-1052.
Cheng, K. and Goldman, R. (1998), Electronic Field and Proliferation in a Dermal Wound Model Cell Cycle Kinetics, Bioelectromagnetics. 68-74.
Stough et al. (2002), "Finasteride improves male pattern hair loss in a randomized study in indentical twins," European Journal of Dermatology, pp. 32-37.

(56) References Cited

OTHER PUBLICATIONS

Todd et al. (2001), "Electrical Stimulation of Transforming Growth Factor-β1 Secretion by Human Dermal Fibroblasts and the U937 Human Monocyctic Cell Line," pp. 693-701.
Unholzer, A and Korting, H. (2002), "High Frequency Ultrasound in the Evaluation of Pharmacological Effects on the Skin," Skin Pharmacology and Applied Skin Physiology, pp. 71-84.
Pete et al. (2002). "Cigareete Smoke-Inducted Lipid Peroxidation in Human Skin and its Inhibition by Topically Applied Antioxidants," Skin Pharmacology and Applied Skin Physiology, pp. 63-68.
Garbaers et al. (2001), "Mossbauer study of iron centers in Dl/D2/Cyt b 559 complexes isolated from photostem II of spinach," European Biophysics Journal, pp. 485-493.
O. Ishiawa et al. (1997), "Morphological and biochemical analyses on fibroblasts and self-produced collagens in a novel three dimensional culture," British Journal of Dermatology, pp. 6-11.
Harmon, C. and Nevins, T. (1994), Biophasic Effect of 1, 25-Dihyoxyvitamin Don Human Hair Follicle Growth and Fiber Production in Whole Organ Cultures, Journal of Investigative Dermatology pp. 318-322.
Reiss, S. (2002), "Photodynamic Therapy: Reaching Beyond Cancer," Biophotonics International Journal, pp. 48-54.
Lahjomri et at. (1997), Pulsed Photoacoustic Study of the Diffusion of Chromophores in Human Skin, Photochemistry and Photobiology. pp. 292-302.
Agramonte, A. (2001), "The Inside History of a Great Medical Discovery," Military Medicine, pp. 66-78.
Tsukahara et al. (2001), "Dirunal variation affects age-related profile in skin thickness," Journal of Cosmetic Science, pp. 391-397.
Ernst, E. and Huntley, A. (2000), "Tea Tree Oil: A system Review of Randomized Clinical Trials," Research in Complementary Medicine, pp. 17-20.
Masuda et al. (2002), "Biosynthesis and distribution of chlorophyll among the photosystems during recovery of the green alga Dunaliella salina from irradiance stress," Plant Physiology, pp. 603-614. (Abstract).
Joet et al. (2002), "Cyclic Electron Flow around Photosystem I in C(C) Plants. In Vivo Control byu the Redox State of Chloroplasts and Involvement of the NADH-Dehydroense Complex," pp. 760-769. (Abstract).
Christen et al. (2000), "Delayed Fluorescence emitted from light harvesting complex II and photosystem II of higher plants in the 100 ns-5 mircos time domain," FEBS Lett., pp. 103-106, (Abstract).
De Wijn et al. (2001), "Secondary stabilization reactions and proton-coupled electron transport in photosytem II investigated by electroluminescence and fluorescence spectroscopy," Biochemistry, pp. 5821-5834.
Hou et al. (2001), "Thermodynamics of electron transfer in oxygenic photosystem reaction centers; a pulsed photoacoustic study of electron transfer in photosystem I reveals a similarity to bacertial reaction centers in both vol. change and entropy," Biochemistry, pp. 7109-7016.
Newman, J.T., Nellermoe, M.D., & Carnett, J.L. (1992). "Hydrocortisone phonophoresis: A literature review," Journal of the American Podiatric Medical Association. 82(8). pp. 432-435.
Menon, G.K., Bommannan, D.B., & Elias, P.M. (1993). "High-frequency sonophoresis: Permeation pathways and structural basis for enhanced permeability," Skin Pharmacol, 7. pp. 130-139.
Mitragotri, S., Blankschtein, D., & Langer, R. (1995). "Ultrasound-mediated transdermal protein delivery," Science, 269. pp. 850-853.
Draper, D.O. Castel, J.C & Castel, D. (1995). "Rate of temperature increase in human muscle during 1 MHz and 3 MHz continuous ultrasound," JOSPT, 22(4). pp. 142-150.
Rougier, A., et al. (1983). "In vivo correlation between stratum corneum reservoir function and percutaneous absorption," The Journal of Investigative Dermatology, 81. pp. 275-278.
Zabel, K. (1999). Wrinkle removal without the wound, Dermatology Times, 20(6).
Zabel, K. (1999). "Future of laser surgery: Unexplored benefits await," Dermatology Times, 20(6).

Gniadecka, M., et at. (1994). " Ultrasound structure and digital image analysis of the subepidermal low echogenic band in aged human skin: Diurnal changes and interindividual variability," The Journal for Investigative Dermatology, 102(3). pp. 362-365.
Mitragotri, S., et al. (1995). "A mechanistic study of ultrasonically-enhanced transdermal drug delivery," Journal of Pharmaceutical Science, 84(6). pp. 697-706.
Meidan, V.M., et al. (1998). "Low intensity ultrasound as a probe to elucidate the relative follicular contribution to total transdermal absorption," Pharmaceutical Research, 15(1). pp. 85-92.
Mitragotri, S., Blankschtein, D & Langer, R. (1996). "Transdermal drug delivery using low-frequency sonophoresis," Pharmaceutical Research, 13(3). pp. 411-420.
Mitragotri, S., Blankschtein, D., & Langer, R. (1986). "An explanation for the variation of the sonophoretic transdermal transport enhancement from drug to drug," Journal of Pharmaceutical Science, 86(10). pp. 1190-1192.
Hippius, M., et al. (1998). "In vitro investigations of drug release and penetration-enhancing effect of ultrasound on transmembrane transport of flufenamic acid," International Journal of Clinical Pharmacological,Therapy, and-Toxicology, 36(2). pp. 107-111.
Miyazaki, S., et al. (1992). "External control of drug release and penetration. VI. enhancing effect of ultrasound on the transdermal absorption of indomethacin from an ointment in rats," Chemical and Pharmaceutical Bulletin, 40(10). pp. 2826-2830.
Asano, J., et al. (1997). "Effect of pulsed output ultrasound on the transdermal absorption of indomethacin from an ointment in rats," Biological and Pharmaceutical Bulletin, 20(3). pp. 288-291.
Miyazaki, S., et al. (1991). "External control of drug release and penetration: Enhancement of the transdermal absorption of indomethacin by ultrasound irradiation," Journal of Pharmaceutical Pharmacology, 43(2). pp. 115-116.
Bommannan, D., et al. (1992). "Sonophoresis.I. The use of high-frequency ultrasound to enhance transdermal drug delivery," Pharmaceutical Research, 9(4). pp. 559-564.
Tachibana, K., Tachibana, S. (1998). "Application of ultrasound energy as a new drug delivery system." Nippon Rinsho, 56(3). pp. 584-588.
Byl, N.N. (1995). "The use of ultrasound as an enhancer for transcutaneous drug delivery: phonophoresis," Physical Therapy, 75(6). pp. 539-553.
Hikima, T., Hirai, Y. & Tojo, K. (1998). Effect of ultrasound application on skin metabolism of prednisolone 21-acetate, Pharmaceutical Research, 15(11). pp. 1680-1683.
Yata, N. (1998). "Enhancement of drug absorption by iontophoresis and phonophores s and clinical application," Nippon Rinsho, 56(3). pp. 808-612.
Kimura, I.F., et al. (1998), "Effects of two ultrasound devices and angles of application on the temperature of tissue phantom," Journal of Orthopedic and Sports Physical Therapy, 27(1). pp. 27-31.
Mikulak, S.A., Vangsness, C.T., & Nimmi, M.E. (1998). "Transdermal delivery and accumulation of indomethacin in subcutaneous tissues in rats," Journal of Pharmaceutical Pharmacology, 50(2). pp. 153-158.
Murakami, T., et al. (1998). "Topical delivery of keloid therapeurtic drug, trailast, by combined use of oleic acid and propylene glycol as a penetration enhancer: Evaluation by skin microdialysis in rats," Journal of Pharmaceutical Pharmacology, 50(1). pp. 49-54.
Stott, P.W., Williams, A.C., & Barry, B.W. (1998). Transdermal delievery from eutictic systems: Enhanced permeation of a model drug, ibuprofen. Journal of Controlled Release, 50(1-3). pp. 297-308.
Morimoto, Y., & Fujimoto, S. (1985). "Albumin microspheres as drug carriers," Critical Review of Therapeutic Drug Carrier Systems, 2(1). pp. 19-63.
Johnson, M,E., et al. (1996). "Synergistic effects of chemical enhancers and therapeutic ultrasound on transdermal drug delivery," Journal of Pharmaceutical Science, 85(7). pp. 670-679.
Illel, B. (1997). "Formulation for transfollicular drug administration: some recent advances," Critical Review of Therapeutic Drug Carrier Systems, 14(3). pp. 207-219.

(56) References Cited

OTHER PUBLICATIONS

Mitragotri, S. (2000). "Synergistic effect of enhancers for transdermal drug delivery," Pharmaceutical Research, 17(11). pp. 1354-1359.
Frenkel, V., Kimmel, E., & Iger, Y. (2000). "Ultrasound-facilitated transport of silver chloride (AgCl) particles in fish skin," Journal of Controlled Release, 68(2). pp. 251-161.
Mitragotri, S. (2001), "Effect of therapeutic ultrasound on partition and diffusion coefficients in human stratum corneum," Journal of Controlled Release, 71(4 pp. 23-29.
Tan, H.S.. & Pfister, W.R. (1999). "Pressure-sensitve adhesives for transdermal drug delivery systems." PSTT, 2(2). pp. 60-69.
Tajima, S., & Pinnel, S.R. (1996). "Ascorbic acid preferentially enhances type I and III collagen gene transcription in human skin fibroblasts," Journal of Dermatological Science. 11(3). pp. 250-253.
Castro, D.J., et al. (1987). "Biostimulative effects of Nd: YAG Q-switch dye on normal human fibroblast cultures: Study of a new chemosensitizing agent for the Nd:YAG laser," Laryngoscope, 97(12). pp. 1454-1459.
Omura, T., et al. (1984), "Hemoprotein H-450 identified as a form of cytochrome P-450 having an endogenous ligand at the 6th coordination position of the heme," Journal of Biochemistry, 96(5). pp. 1491-1500.
Hrnjak, M., et al. (1995). "Stimulatory effect of low-power density He—Ne laser radiation on human fibroblasts in vitro," Vojnosanit Pregl, 52(6). pp. 539-546.
Krammer, B., Hubmer, A., & Hermann, A. (1993). "Photodynamic effects on the nuclear envelope of human skin fibroblasts," Journal of Photochemistry and Photobiology, 17(2). pp. 109-114.
Lyons, R.F., et al. (1987). "Biostimulation of wound healing in vivo by a helium-neon laser," Annals of Plastic Surgery, 18(1). pp. 47-50.
Yu, W., Naim, J.O.., & Lanzafame, R.J. (1997). "Effects of photostimulation on wound healing in diabetic mice," Lasers in Surgery and Medicine, 20(1). pp. 56-63.
Morrone, G., et al. (1998). "In vitro experimental research of rabbit condrocytes biostimulation with diode laser Ga-Al-As; a preliminary study," Artificial Cells, Blood Substitutes, and Biotechnology, 26(4). pp. 437-439.
Van Breugel, H.H., & Bar, P.R. (1992). "Power density and exposure time of He—Ne laser irradiation are more important than total energy dose in photo-biomodulation of human fibroblasts in vitro," Lasers in Surgery and Medicine, 12(5). pp. 528-537.
Yano, K., Lawrence, B.F., & Delmar, M. (2001). "Control of hair growth and follicle size by VEGF-mediated angiogenesis." The Journal of Clinical Investigation, 107(4), pp. 409-417.
Wei, Y.H., et al. (2001). "Mitochondriat theory of aging matures-Roles of mtDNA mutuation and oxidative stress in human . aging." Chinese Medical Journal, 64, pp. 259-270.
Hoffman, J.W., et al (2004). "Myocardial reperfusion injury: Etiology, mechanisms, and therapies." The Journal of the American Society of Extra-Corporeal Technology, 36, pp. 391-411.
Chwirot, W.B. (1986). "New indications of possible role of DNA in ultraweak photon emission from biological systems." Journal of Plant Physiology, 122, pp. 81-86.
Albrecht-Buehler, G. (1994). "Cellular infrared detector appears to be contained in the centrosome." Cell Motility and the Cytoskeleton 27, pp. 262-271.
Kiang, J.G. (2004). "Inducible heat shock protein 70kD and inducible nitric oxide synthase in hemorrhage/resuscitation-induced injury." Cell Research, 14(6), pp. 450-459.
Yu, W., et al (1997). "Improvement of host response to sepsis by photobiomodulatio." Lasers in Surgery and Medicine,7 21(3), pp. 262-268.
Byrnes, K.R., et al. (2004). "Photobiomodulation improves cutaneous wound healing in an animal model of type II diabetes." Photornedicine and Laser Surgery, 22(4), pp. 281-290.
Byrnes, KR., et al. (2005). "Light promotes regeneration and functional recovery and alters the immune response after spinal cord injury." Lasers in Surgery and Medicine, Feb. 2009, (online).

Wong-Riley, M.T., et al. (2005). "Photobiomodulation directly benefits primary neurons functionally inactive by toxins: role of cytochrome c oxidase." Journal of Biological Chemistry. 280(6), pp. 4761-4771.
El Hindi, T et al. (2004). "Determination of the antioxidant capacity of an antioxidant combination using the fluoroscan assay in vitro and visualization of its effects using histological methods." Archives of Dermatological Research, 296(6), pp. 258-264.
Elmets, CA., Vargas, A., & Oresajo, C. (1992). "Photoprotective effects of sunscreens in cosmetics on sunburn and cell photodamage." Photodermatology, Photoimmunology, and Photomedicine, 9(3), pp. 113-120.
Stein, R. (2005). "Fat found to accelerate aging process." Washington Post, Jun. 14, 2005.
Block, G., et al. (2004). "Plasma-C reactive protein concentrations in active and passive smokers: influence of antioxidant supplementation." Journal of the American College of Nutrition, 23(2), pp. 141-147.
Node, Y., et al. (2002). "Antioxidant activities of pomegranate fruit extract and its anthocyaninidins: deiphindin, cyaniding, and pelagronidin." Journal of Agricultural and Food Chemistry, 50(1), pp. 166-171.
Monaco, J.L. & Lawrence, W.T. (2003). "Acute wound healing an overview." Clinics in Plastic Surgery, 30, pp. 1-12.
Hinz, B., et al. (2001). "Apha-smooth muscle actin expression upregutates fibroblast contractile activity." Molecular Biology of the Cell, 12, pp. 2730-2741.
Azevedo, L.H., et al. (2005). "Evaluation of low intensity laser effects on the thyroid gland of mate mice." Photomedicine and Laser Surgery, 23(6), pp. 567-570.
Tuby, H., Maltz, L., & Oron, U. (2006). "Modulation of VEGF and iNOS in the rat heart by low level laser therapy are associated with cardioprotection and enhanced angiogensis." Lasers in Surger and Medicine, 38, pp. 682-688.
Fratelli, M., et al. (2005). "Gene expression n. profiling reveals a signaling role of gluthathione in redox regulation." PNAS, 102(39), pp, 13998-14003.
Hymes, S.R., Strom. E.A., & Fife, C. (2006). "Radiation dermatitis: Clinical presentation. pathophysiology, and treatment 2006." Journal for the American Academy of Dermatology, 54, pp. 28-46.
Omura, Y. (2004). "Special sunrise & sunset solar energy stored papers and their clinical applications for intractable pain, circulatory disturbances & cancer Comparison of Beneficial effects between special solar energy stored paper and quigong energy stored paper." Acupuncture & Electro-therapeutics. 29, pp. 1-42.
Stoica, E. & Enulescu, 0. (1988). Catecholamine response to light in migraine Cephalalgia, 8, pp. 31-36.
Kowluru, R.A. (2005). "Diabetic retinopathy: mitochondrial dysfunction and retinal capillary cell death." Antioxidants & Redox Signaling, 7(11,12), pp. 1581-1587.
McDaniel, D., et al. (1998). "Body contouring: A preliminary report on the use of the silhouette® device for treating cellulite." Aesthetic Surgery Journal, 18(3), pp. 177-182.
Noton, D. (2000). "Migraine and photic stimulation: Report on a survey of migraineurs using flickering light therapy." Complementary Therapies in Nursing & Midwifery, 6, pp. 138-142.
Alstadhaug, KB., Salvesen, R., & Bekkelund, S.I. (2005). "Seasonal variation in migraine." Cephalalgiai, 25, pp. 811-816.
Claustrat, B., et al. (2004). "Melatonin secretion is supersensitive to light in migraine." Cephalalgia, 24, pp. 128-133.
Passache, G., et al. (2000). "Mitochondria of retinal muller (glial) cells: The effects of aging and of application of free radical scavengers." Opthalmic Research, 32, pp. 229-236.
Liang, F.Q. & Godley, B.F. (2003). "Oxidative stress-induced mitochondrial DNA damage in human retinal pigment epithelial cells: A possible mechanism for RPE aging and age-related macular degeneration," Experimental Eye Research, 76, pp. 397-403.
Anderson, D.J., et al. (1997), "Preliminary trial of photic stimulation for premenstrual syndrome." Journal of Obstetrics and Gynaecology, 17(1), pp. 76-79.
Main, A. et al. (2000). "The wavelength of light causing photophobra in migraine and tension-type headache between attacks." Headache. 40, pp. 194-199.

(56) References Cited

OTHER PUBLICATIONS

Eells, J.T., et al. (2004), "Mitochondria] signal transduction in accelerated wound and retinal healing by near-infrared light therapy." Mitochondrion, 4, pp. 559-567.
"Thiol" From Wikipedia page: http://en.wikipedia.org/wiki/Thiol Accessed: May 6, 2007.
"Disulfide Bond" From Wikipedia page: http://en.wikipedia.org/wiki/Disulfide_bond Accessed: May 6, 2007.
"Permanent Wave" From Wikipedia page: http://en.wikipedia.org/wiki/Permanent_wave Accessed: May 6, 2007.
Martin, K. (2007). "Infrared and ramen studies of skin and hair: A review of cosmetic spectroscopy." The Internet of Vibrational Spectroscopy, 3(2), online Accessed: Apr. 24, 2007.
Jarrousse, F., et al. (2001). "Identification of clustered cells in human hair follicle responsible for MMP-9 gelatinolytic activity: Consequences for the regulation of hair growth." International Journal of Dermatology, 40(6), pp. 385-392.
Langbein, et al. (2001). "Figure 8." Journal of Biological Chemistry, 276(37), pp. 35123.
King, A., et al. (2004). "Mitochondria-derived reactive oxygen species mediate blue light-induced death of retinal pigment epithelial cells." Photochemistry and Photobiology, 79(5), pp. 470-475.
"The EpiOcularModelTM." http://www.mattek.com/pp./products/epiocular. Mattek Corporation. Accessed: Apr. 27, 2005.
"Folliquant®: A range of in vivo assays of hair follicle damage and alopecia." EpiStem® LTD. Copyright 2003 Epistem Ltd.
Davis, S.C., et al. (2004). "To examine the effect of GentleWaves LED photomodulation device on deep partial thickness wound healin." Preliminary Protocol: Deep Partial thickness wound study. Department of Dermatology and Cutaneous Surgery, University of Miami School of Medicine.
"Virulite CS® . . . The ORIGINAL Cold Sore Machine." http://www.virulite.com/technical_information.html Date accessed: Jan. 26, 2008.
Christensen, B. (2008). "Forced resonance ultra-short pulse laser kills viruses dead." Technovelogy.com Where Science Meets Fiction, http://www.technovelogy.com/ct/Scienc.e-Fiction-Nevvs.asp?NewsNum=1311. Date Accessed: Jan. 26, 2008.
"Visual Signal Transduction." Biocarta http://wwwbiocarta.comipathfiles/h_rhodospinPathway.asp Date Accessed: Aug. 29, 2005.
Epstein, P. (2007). "Trials that matter: Two faces of progress in the treatment of age-related macular degeneration." Annals of Internal Medicine, 146(7), pp. 532-534.
Ostler, E.L. et al. (2000) "Telomerase and the cellular lifespan Implications of the aging process." Journal of Pediatric Endocrinology and Metabolism, 13(6), pp. 1467-1476.
Lou, H. J. et al.(2002). "Lighting the way: Molecular beacons offer a highly sensitive, flexible method for DNA analysis." Spies OEMagazine. Feb., pp. 23-25.
"The Relief Light: A sensible alternative to 'soft' laser technology." Retrieved: http://www.fredomunlimited.net/relief%20light.htm Date Accessed: Feb. 9, 2002.
Stern, R. et al. (2001)."Hyaluronidase can modulate expression of CD44." Experimental Cell Research, 265, pp. 1-10.
Mio, K. et al. (2000). "Evidence that the serum inhibitor of hyaluronidase may be a member of the inter-a-inhibitor family." Journal of Biological Chemistry, 275(42), pp. 32413-32421.
Mortimer, A.J., & Dyson, M. (1988). "The effect of therapeutic ultrasound on calcium uptake in fibroblasts." Ultrasound in Medicine and Biology, 14(6), pp. 499-506.
Office Action dated Sep. 13, 2013 in U.S. Appl. No. 12/550,746.
Canadian Office Action dated May 30, 2013 issued in Canadian Patent Application No. 2,533,129.
Translation of amended claims filed in response to Second/Final Notice of Reasons for Rejection dated Feb. 20, 2013 issued in Japanese Patent Application No. 2008-553383.
Translation of Written Amendment dated Aug. 6, 2013 in response to Second/Final Notice of Reasons for Rejection dated Feb. 6, 2013 issued in Japanese Patent Application No. 2008-557382.
Response filed May 31, 2013 to office action dated Nov. 16, 2012 in Chinese Patent Application No. 201110210275.4.
Decision on Rejection dated Jun. 28, 2013 in Chinese Patent Application No, 201110210275.4.
European Office Action dated Oct. 3, 2013 issued in European Patent Application No. 02792232.7.
Canadian Office Action dated Aug. 23, 2013 issued in Canadian Patent Application No. 2644219.
Japanese Office Action dated Dec. 2, 2013 issued in Divisional Japanese Patent Application No. 2009-236857.
Canadian Office Action dated Oct. 8, 2013 issued in Canadian Patent Application No. 2640203.
Japanese Office Action dated Jan. 8, 2014, issued in Japanese Application No. 2008-557382, filed Mar. 2, 2007, GentleWaves LLC.
Japanese Office Action dated Feb. 10, 2014, issued in Japanese Application No. 2008-553383, filed Feb. 2, 2007, GentleWaves LLC.
Communication pursuant to Article 94(3) EPC dated Sep. 18, 2014, in Application No. 02 792 232.7-1458.
Office Action dated Oct. 6, 2014,in Canadian Patent Application No. 2640203.
Office Action dated Dec. 4, 2014, in Canadian Patent Application No. 2,644,219.
Office Action dated Nov. 13, 2015, in Canadian Patent Application No. 2,640,203.
European Search Report dated Sep. 26, 2016 in Application No. 16150664.7.
Office Action dated Oct. 25, 2016, in Canadian Patent Application No. 2,644,219.
Canadian Office Action dated Apr. 4, 2016 in Patent Application No. 2,644,219.
Extended European Search Report dated Aug. 24, 2016 in Patent Application No. 16150664.7.
Mitchel P. Goldman, et al, "A Single-Center Study of Aminolevulinic Acid and 417 NM Photodynamic Therapy in the Treatment of Moderate to Severe Acne Vulgaris", Journal of Drugs in Dermatology, vol. 2, No. 4, XP008116268, 2003, pp. 393-396.
Amy Forman Taub, "Photodyanamic Therapy for the Treatment of Acne: A Pilot Study", Journal of Drugs in Dermatology, vol. 3, No. 6, XP009191295, 2004, pp. S10-S14.

* cited by examiner

Chlb ( *C05307* )
Chlorophyll b

*Haem b (C00032)*
Protoporphyrin IX

Pentacoordinate

Chlorophyll a

Pentacoordinate /
Hexacoordinate

Protoporphyrin IX

Peak OD=2.254 at 403 nm

METHOD AND APPARATUS FOR SKIN TREATMENT

The present application is a continuation application of U.S. Ser. No. 12/583,578, filed Aug. 21, 2009, which is a continuation application of U.S. Ser. No. 11/332,517, filed Jan. 17, 2006, now abandoned, which is a continuation application of U.S. Ser. No. 11/119,378, filed May 2, 2005, now U.S. Pat. No. 7,201,765, which is a divisional application of U.S. Ser. No. 09/933,870, filed Aug. 22, 2001, now U.S. Pat. No. 6,887,260, which is a continuation-in-part of U.S. Ser. No. 09/819,082, filed Feb. 15, 2001, now abandoned, which is a divisional application of U.S. Ser. No. 09/203,178, filed Nov. 30, 1998, now U.S. Pat. No. 6,283,956, the entire contents of all of which are incorporated herein by reference.

FIELD OF INVENTION

The present invention generally relates to a system and method for the treatment of skin disorders and, more specifically, to the treatment of skin using a combination of photothermal, photochemical and/or photomodulatory means. In general, the invention relates to the exposure of the skin to multiple wavelengths of light, alone or in combination with the application of a cosmeceutical composition, naturally occurring chromophore, or other light-activated chromophore to or into the oil gland and surrounding tissue and exposing the composition.

BACKGROUND OF THE INVENTION

There are several known techniques for attempting to reduce or eliminate the skin disorders associated with the activity of sebaceous oil glands. The primary disorder is acne with an associated disorder of acne scarring. A few of these known techniques are scientifically proven and widely accepted as effective. However, their degree of efficacy varies greatly.

There are several processes which may be used for inhibiting the activity of sebaceous oil glands. In one process the target may be duct of the gland and the treatment focuses on the treatment of sebaceous follicles to eliminate the associated disorders. In U.S. Pat. No. 6,183,773, to Anderson, which is hereby incorporated by reference, an attempt is made to treat sebaceous gland disorders using lasers which irradiate energy activatable material, primarily laser sensitive dyes, that have been applied to the skin.

Anderson teaches a method for treating skin disorders associated with sebaceous follicles by topically applying an energy activatable material to a section of skin afflicted with a sebaceous gland disorder, wherein the material is activated by energy which penetrates outer layers of epidermis. A sufficient amount of the material infiltrates the afflicted section of skin and is exposed to sufficient energy to cause the material to become photochemically or photothermally activated, thereby treating the sebaceous gland disorder. In one embodiment, the sebaceous gland disorder is acne. Suitable energy sources for use in accordance with Anderson's invention include flash lamp based sources and lasers, such as Nd:YAG, Alexandrite, flash lamp-pumped dyes and diodes. The energy source can be a continuous wave energy source or pulsed. In the preferred embodiment, the energy activatable material is a laser sensitive chromophore, e.g., a chromophore which is capable of being photoactived by a laser, e.g., a dye. Anderson describes a particularly preferred embodiment, wherein the chromophore is methylene blue.

Anderson's method, however, fails to take advantage of the recent developments in light emitting diode technology that permits the use of LEDs for dermatological use in place of much more expensive lasers. Further, due to the high-intensity nature of lasers, severe skin damage or other injury can occur when the light source is improperly operated. Further, the laser dyes and other topical compositions described by Anderson are expensive and require FDA approval for their intended use, making the invention expensive and time consuming to implement. Further, because of Anderson's focus on the oil gland itself, rather than the elimination of the acne bacteria, suitable results may not be achieved in all cases.

In WO 00/02491, to Harth et al., a method and apparatus are disclosed for eliminating acne bacteria through photothermal means by exposing the bacteria to a narrow band light source in the range of 405 nm to 440 nm. Harth et al., as well, failed to appreciate the opportunity for current LED technology to be applied to dermatologic treatment and, like Anderson, do not disclose means for treating sebaceous oil gland disorders without the high cost and time commitment necessary to receive FDA approval require for high-intensity light therapies with topical compositions such as methylene blue.

In each of the known attempts to treat sebaceous gland disorders, extensive investment in expensive light sources and topical drug composition testing is required. Moreover, none of these attempts addresses the secondary disorder associated with acne—acne scarring.

Consequently, it would be desirable to have a treatment for sebaceous gland disorders and, in particular, acne that addresses and treats acne scarring without the need for expensive, potentially dangerous high-intensity light sources. Further, it would be beneficial for such a treatment regiment to include the use of naturally occurring compositions that fall into the category of cosmetics and cosmeceuticals that are generally recognized as safe and that do not require FDA approval, thereby eliminating the time and resource expenditures associated with the commercial implementation of such a treatment regime.

SUMMARY OF THE INVENTION

In one embodiment of the invention, the process for treating skin disorders, and particularly the treatment of sebaceous oil glands comprises applying a photomodulation enhancing agent, such as a naturally occurring native chromophore, to the skin proximate to or directly to a sebaceous oil gland, tissue feeding said sebaceous oil gland, or both, and exposing said photomodulating enhancing agent to a source of electromagnetic radiation comprising at least one dominant emissive wavelength. The photomodulation enhancing agent should have an absorption characteristic at the dominant emissive wavelength carefully selected to cause the inhibition of, reduction in size of, or the destruction of sebaceous oil glands, tissue feeding off the sebaceous oil gland, or both.

Further, source of electromagnetic radiation may be selected from the ultrasound radiation, light emitting diodes, lasers such as laser diodes and dye lasers, metal halide lamps, flashlamps, mechanically filtered fluorescent light sources, mechanically filtered incandescent light sources, natural or filtered sunlight, or combinations thereof. In a preferred embodiment, the source of the electromagnetic radiation is a light emitting diode having a dominant emissive wavelength of from about 300 nm to about 1400 nm. Even more preferred is when the light emitting diode has a dominant emissive wavelength at one of 400 nm, 420 nm, 430 nm, 445 nm, 635 nm, 655 nm, 660 nm, 670 nm, 780 nm, 785 nm, 810 nm, 830 nm, 840 nm, 860 nm, 904 nm, 915 nm, 980 nm, 1015 nm, and 1060 nm.

In another preferred embodiment, the photomodulation enhancing agent has a local electromagnetic absorption maximum at the dominant emissive wavelength of the light source used for treatment. Further, treatment contemplated using the photomodulating enhancing agent requires exposing the agent to a plurality of pulses from said source of electromagnetic radiation for a therapeutically effective pulse length and pulse duration. In one embodiment of the invention, the exposure is to an LED emitter outputting about 2 milliwatts for about 20 minutes or to 100 milliwatts/$cm^2$ for 10 minutes from a metal halide light source, and in alternate embodiments, the electromagnetic radiation is emitted at an energy level of from about 0.1 $W/cm^2$ to about 5.0 $W/cm^2$.

The topical agent of the present invention may include particles of a size enabling penetration of a sebaceous oil gland duct. In particular, particles may have an average diameter of less than about 5 μm. More generally, the photomodulation enhancing agent is a composition made up of of at least one of Vitamin C, Vitamin E, Vitamin A, Vitamin K, Vitamin F, Retin A (Tretinoin), Adapalene, Retinol, Hydroquinone, Kojic acid, a growth factor, *echinacea*, an antibiotic, an antifungal, an antiviral, a bleaching agent, an alpha hydroxy acid, a beta hydroxy acid, salicylic acid, antioxidant triad compound, a seaweed derivative, a salt water derivative, an antioxidant, a phytoanthocyanin, epigallocatechin 3-gallate, a phytonutrient, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, Rogaine, a hair growth stimulating substance, a hair growth inhibiting substance, a dye, a natural or synthetic melanin, a metalloproteinase inhibitor, proline, hydroxyproline, an anesthetic substance, chlorophyll, copper chlorophyllin, carotenoids, bacteriochlorophyll, phycobilins, carotene, xanthophyll, anthocyanin, and derivatives and analogs of the above, both natural and synthetic, and mixtures thereof. The composition may be chlorophyll, carotenoids, derivatives thereof, and mixtures thereof.

The method of the present invention may be further enhanced by subjecting the photomodulation or photothermal enhancing agent to a penetration enhancing procedure prior to exposing the enhancing agent to the source of electromagnetic radiation. Such procedures increase permeability of the skin or decrease skin barrier function and may be helpful for optimizing the present invention. Options for this include, but are not limited to, stripping, removing, thinning or diminishing the structure, function, thickness or permeability of the stratum corneum by various mechanical, abrasive, photo acoustical, ablative, thermal, chemical, abrasive or enzymatic methods. Examples of these could include solvent or tape stripping, scrubbing, laser ablation or vaporization, chemical peeling, micro dermabrasion, enzyme peeling, or laser treatment using high peak power, short pulse duration lasers.

The method of the present invention may be carried out with a light source alone or, preferably, in combination with one of the topical compositions listed above. In either case, a preferred source of electromagnetic radiation is a light emitting diode having a dominant wavelength of 410 nm and a bandwidth of +/−at least 5 nm. Further, use of various light sources to enhance the treatment of the present invention by photothermal means is also desirable for some forms of treatment. The present invention may be used as described or in conjunction with traditional acne skin care treatments and kits.

BRIEF DESCRIPTION OF THE DRAWINGS

FIG. 10 shows the absorption spectrum for human fibroblast overlayed with the wavelengths of various, commercially produced LEDs, and also the absoprtion spectrum of chlorophyll a.

Figure 1:
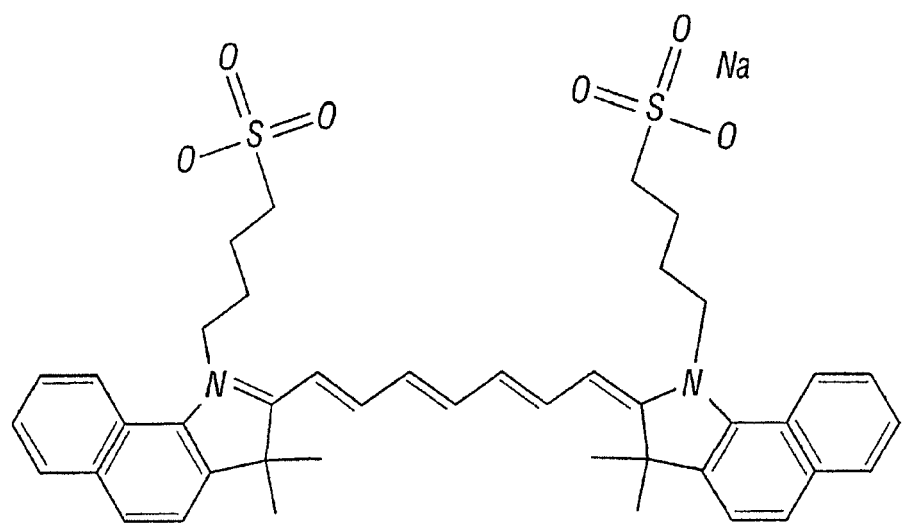
FIG. 1 is an illustration of the chemical structure of methylene blue.

A detailed description of a preferred embodiment of the present invention will be made with reference to the accompanying drawings.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

In a preferred embodiment, the present invention is directed to a process for dermatologic treatment. Such a treatment may include the photomodulation of sebaceous oil glands and the surrounding tissue or producing temporary or permanent reduction of activity or destruction of sebaceous oil glands or supporting tissue or the removal, in human or mammalian skin, of some or all of the hairs growing approximate to oil glands. In a preferred embodiment the process produces little or no permanent injury or damage to nearby skin tissue. Substantially only the oil gland and immediately surrounding tissue are affected.

In a process according to one embodiment of the present invention, an agent may be selected which is capable of penetrating the oil gland and surrounding tissue. The agent may be characterized as an active agent in that it performs a function in addition to simply occupying or contaminating the space in the ducts surrounding the gland. Alternatively, the agent may perform the passive function filling the void space in the ducts surrounding the glands, depending on the nature of the treatment desired. The agent may have sufficient optical absorption of a wavelength (or a combination of wavelengths) of a coherent or non-coherent light source which can penetrate the skin adequately to be absorbed by the target agent or the new agent-tissue complex.

The area of skin overlying where the oil gland is located may be cleansed. After the skin is cleansed, the skin may be treated to improve permeability. This may be accomplished, for example, by treating the skin with steam or a hot moist towel to hydrate the skin and hair or removing a portion of the stratum corneum through various means known in the art, exemplary of which is microdermabrasion.

The agent may be applied in sufficient quantity and in suitable form to be incorporated into the target tissue in adequate or optimal amounts to allow the production of the desired tissue effect.

Excess agent may be removed, neutralized, inactivated, decolorized, diluted or otherwise altered so that residual contamination of the skin by such excess agent is either (a) absent and does not interact with the light or energy source, or (b) present in such small quantity that it provides no clinical effect.

Delivery of the desired agent into the target tissues may be enhanced, facilitated or made possible by the use of enzymes capable of altering the structure, permeability, or other physical characteristics of the stratum corneum or by the use of ultrasound or phonophoresis either for penetration into the gland or surrounding target tissues or, once penetrated, to cause the release of the agent from the encapsulated delivery device such as liposomes, polymers, microspheres, etc. so as to cause penetration or attachment of this active agent. Ultrasound may be used therapeutically to interact directly with the agent or the agent-tissue complex to produce the desired damaged target tissues (to be used alone or in combination with laser or non-laser light sources). Microderm abrasion may also be used to permit greater penetration of the skin, wherein the upper epithelial layers are removed. These layers create a natural barrier to the permeability of the skin and by their removal, penetration of the skin by topical agents is facilitated. This method may be further enhanced by using ultrasound, alone or in combination with alteration of the stratum corneum, to further improve the performance of topical compositions. A more detailed description of several aspects of the use of ultrasound may be found, for example, in the applicant's U.S. Pat. No. 6,030,374 for "Ultrasound Enhancement of Percutaneous Drug Absorption" which is hereby incorporated by reference in its entirety.

Although preferred embodiments of the present invention may use LEDs, ultrasound and/or laser or light energy, the present invention is not limited to the use of these energy sources. Other sources of energy, including (without limitation) microwave energy and radio frequency energy may also be used. Exemplary of known light sources are fluorescent lights, flashlamps, filamentous lights, etc. One skilled in the art will recognize that any light source capable of emitting electromagnetic radiation at a medically useful wavelength, as described herein, directly, or by means of optical filtration, is within the scope of suitable light sources according to the present invention. For purposes of the photomodulatory and photothermal treatment methods described, any source capable of emitting light having a wavelength from about 300 nm to about 1400 nm, or producing electromagnetic radiation which is filtered or otherwise altered to exposure the skin, a topical composition, or other component of the present treatment regime to a wavelength of light in the aforementioned range is medically useful.

Figure 14:
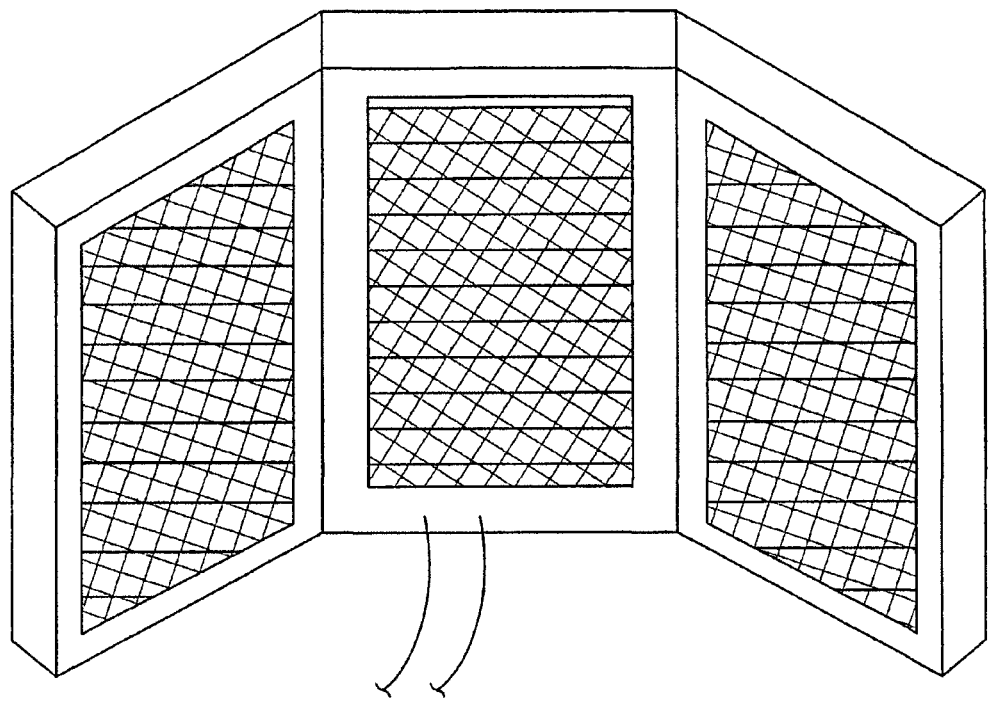
FIG. 14 depicts a front view, in perspective, of a three-panel array of LEDs for treatment in accordance with an embodiment of the present invention.
Figure 15:
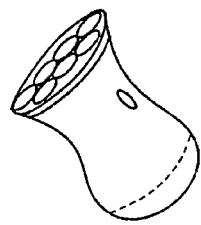
FIG. 15 is a perspective view of hand-held LED devices for treatment in accordance with the present invention.
Figure 15:

The targeted skin may be exposed to one or more wavelengths of LED, laser or non-laser light such as filtered filamentous sources or fluorescent sources or single or multiple frequencies of ultrasound. A variety of parameters may be used (including pulse duration, energy, single or multiple pulses, the interval between pulses, the total number of pulses, etc.) to deliver sufficient cumulative energy to interact with the agent or tissue complex. This results in the inhibition or destruction of the sebaceous oil gland or the supporting skin tissue through photomodulatory means, photothermal means, or combinations thereof. Ultrasound may also be used to preheat the target structures or the entire skin. Further for treatment over a broad area of human skin, the light source may be diffused through a device such as a holographic diffuser; or, alternatively, the light source may be comprised of an array of individual emitters such as the three-panel array of LEDs illustrated in FIG. 14. For localized treatment, smaller arrays or individual LEDs, such as in the hand held devices depicted in FIG. 15 may be used. Since LED sources are considered "insignificant risk devices", no medical supervision is required and these devices may be used by the patient for at-home treatment or as part of an ongoing skin-care system after receiving treatment by a physician.

The topical agent may be incorporated into the target tissue by a variety of mechanisms. These mechanisms include, but are not limited to: 1) physical incorporation into the gland or target tissue cells while leaving the chemical structure essentially unaffected, or 2) undergoing a chemical reaction resulting in a new agent-tissue complex which then becomes a target for energy absorption.

The process may be a single or multi-step process and may involve the use of cofactors, catalysts, enzymes, or multiple agents which interact to ultimately become or create an active agent or agent-tissue complex.

Agents may include, without limitation, the following compositions and derivatives and analogs thereof: hair dyes, vegetable dyes, food coloring, fabric dyes, tissue stains, shoe or leather dyes, other plant products (such as flavonols, chlorophyll, copper chlorophyllin, bacteria chlorophylls, carotenoids, enzymes, monoclonal antibodies, any immunological agent, genetically engineered agent, benign infectious agents, whether naturally occurring or genetically engineered (e.g. the bacteria that normally reside on the skin such as acne bacteria, etc.), antibiotics, agents which attach to sebocytes in the sebaceous gland or duct cells directly, whether by topical or systemic agents that localize in these target tissues, including antibodies or antibody-chromophore compounds of these structures. The preceding list is illustrative and not exhaustive of those agents suitable for use in accordance with the present invention. In general, the topical agent chosen will have certain absorption characteristics that augment the penetration of the radiation to the tissue targeted for treatment, i.e., sebaceous oil gland, acne-scarred tissue, etc.

Figure 2:
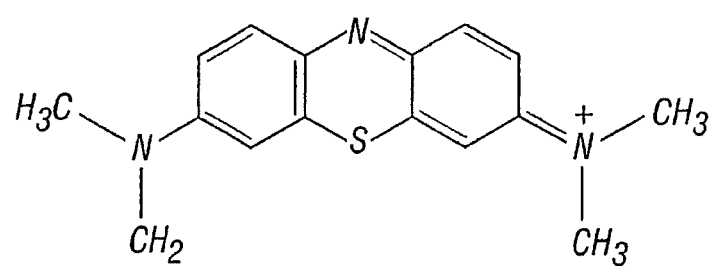
FIG. 2 shows the chemical structure of indocyanin green.
Figure 4A:
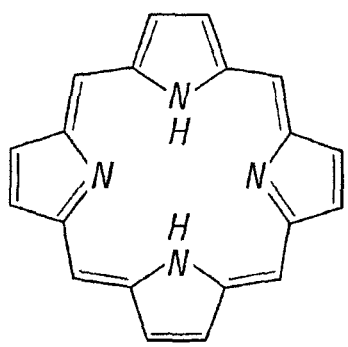
FIG. 4a shows the general chemical structure of a porphyrin molecule.
Figure 4B:
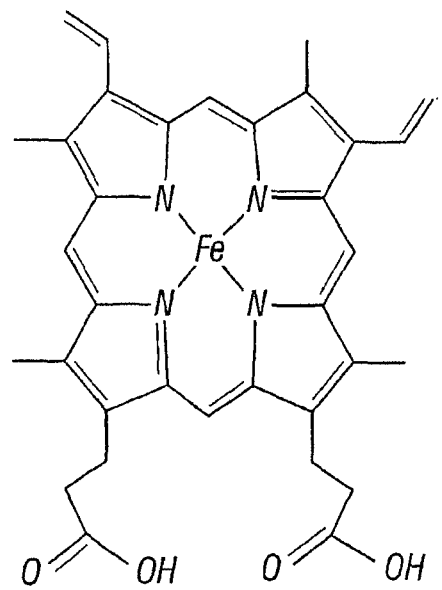
FIG. 4b shows the structure of porphyrin IX.
Figure 5A:
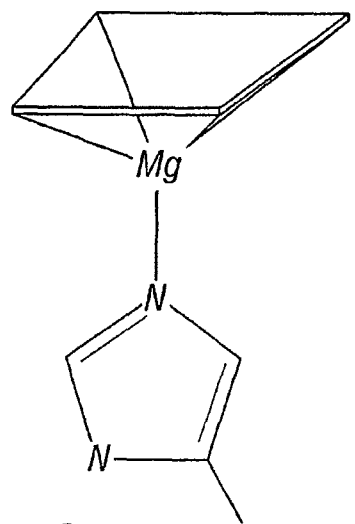
FIG. 5a illustrates the physical structure of the ligand bond portion of a chlorophyll a molecule.
Figure 5B:
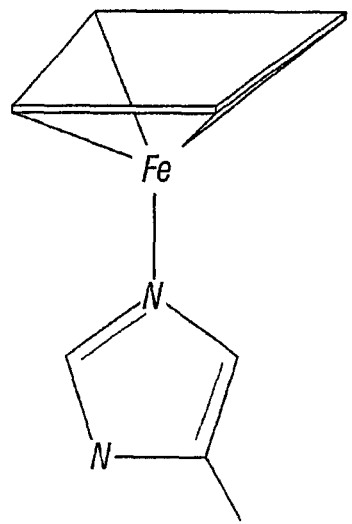
FIG. 5b illustrates the physical structure of the ligand bond portion of a protoporphyrin IX molecule.
Figure 6:
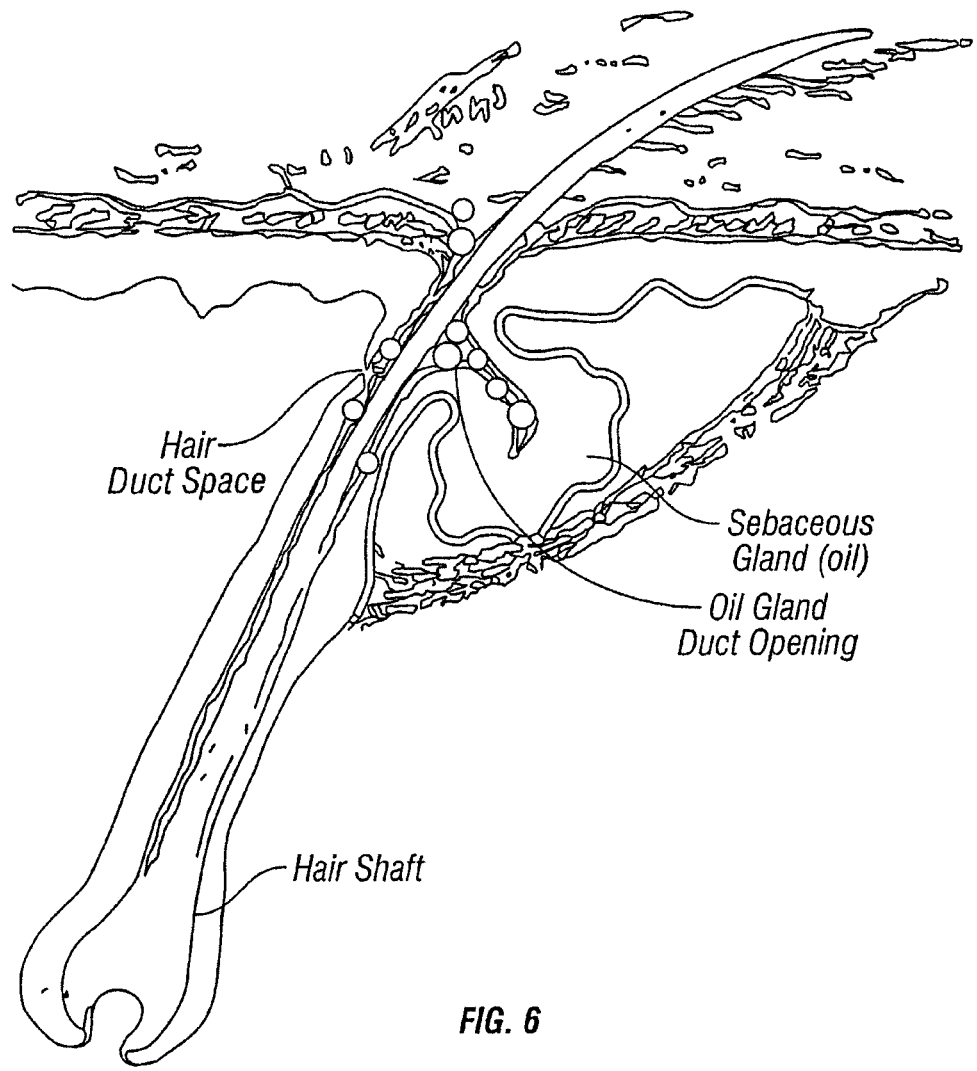
FIG. 6 illustrates a sweat gland and the epithelial layers of human skin.

Most preferable are topical compositions that include a quantity of a naturally occurring chromophore such as chlorophyll, chlorophyllin, polyporphyin, bacteriochlorophyll, protopolyporphyin, etc. These compositions are characterized by a metal-ligand bond as is illustrated in FIGS. 3b and 4b, specifically, and in FIGS. 3 and 4 more generally. Further, FIGS. 5a and 5b show the metal-ligand bond physical structure that is common to the naturally occurring native chromophores of the present invention, as well as the cyclic tetrapyrrole ring that chlorophyll shares with suitable cytochromes. In contrast, synthetic chromphores do not include a metal-ligand bond, nor do they exhibit the same general physical structure as naturally occurring chromophores, as is illustrated by the structure of methylene blue, FIG. 1, and indocyanin green, FIG. 2.

Agents may be delivered in pure form, in solution, in suspension, in emulsions, in liposomes, in synthetic or natural microspheres, microsponges or other known microencapsulation vehicles, alone or in combination. This list of the forms of the agents is illustrative and not exhaustive. Those skilled in the art will recognize that there are a wide variety of forms for the delivery of topical compositions suitable for use in accordance with this invention.

The process may include an application of an active agent and treatment with an energy source as a single treatment. Alternatively, treatment with an energy source may be delayed for hours or days after application of an active agent. Application of an active agent may be performed or applied at another location, such as patient's home, prior to the energy treatment.

After an energy treatment has occurred it may be desirable in some situations to remove, neutralize, decolorize or otherwise inactivate any residual active agent. In other situations, continued application to replenish depleted chromophore may be desirable.

Figure 7:
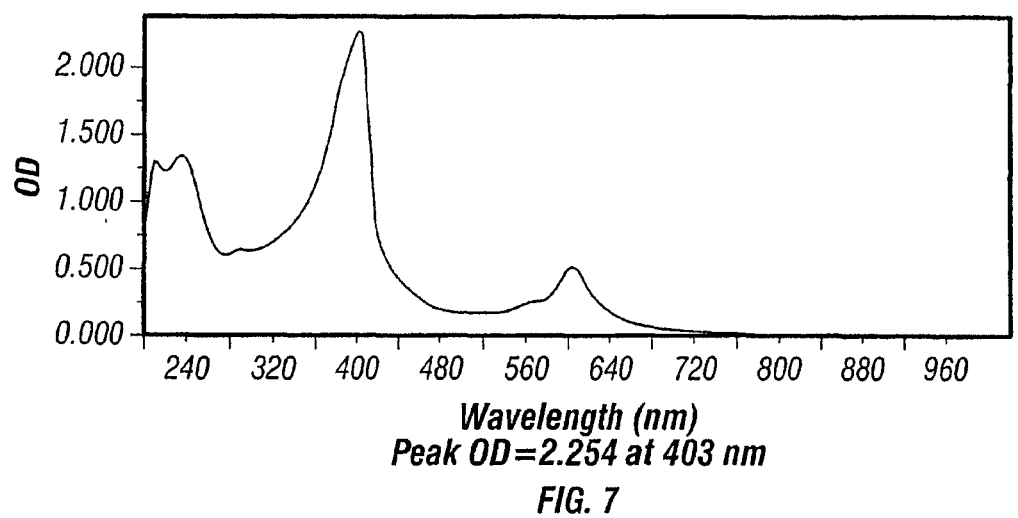
FIG. 7 is a graph showing the absorption spectrum of 0.03% Na Cu chlorophyllin in water.
Figure 8:
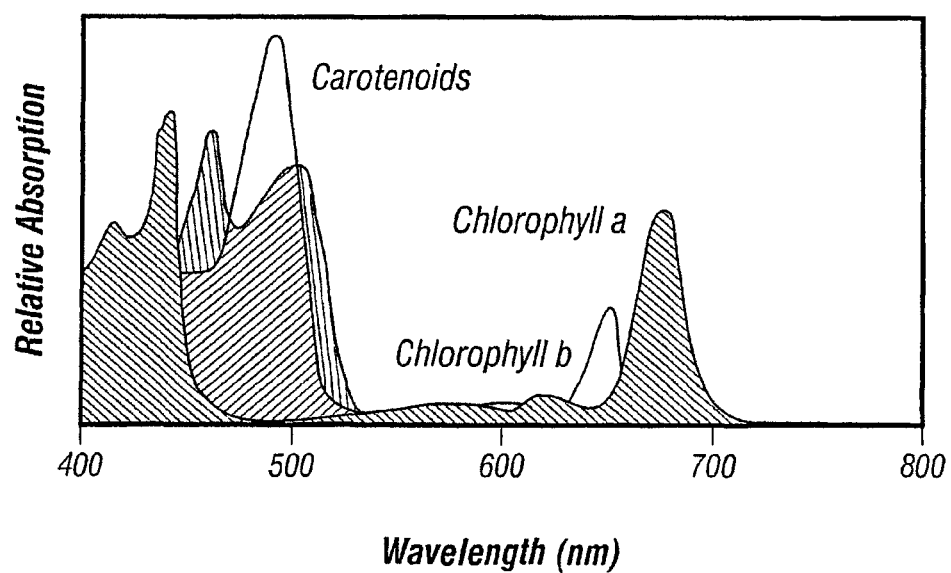
FIG. 8 illustrates the relative absorption spectra of various naturally occurring chromophores.
Figure 9:
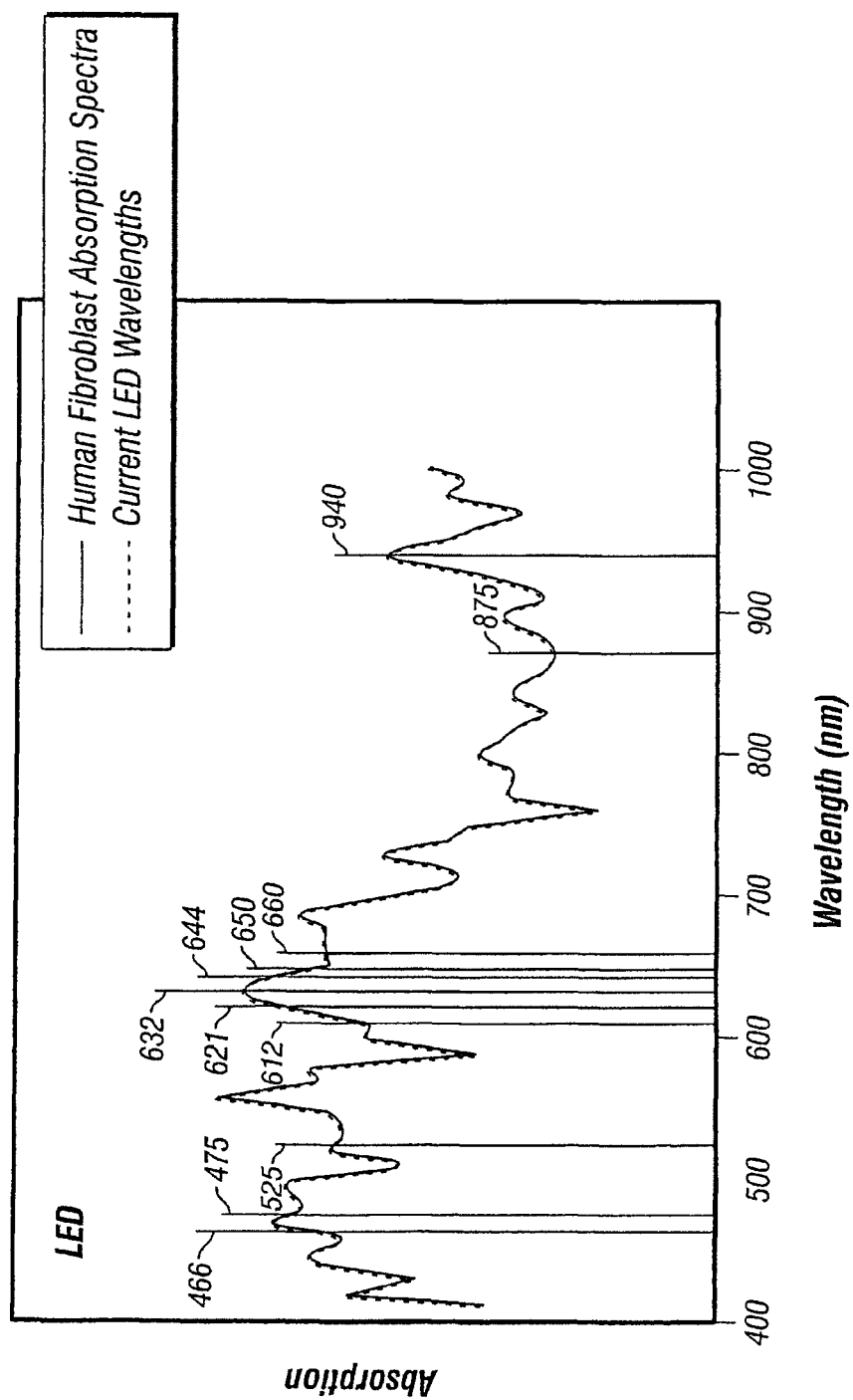
FIG. 9 shows the absorption spectrum for human fibroblast overlayed with the wavelengths of various, commercially produced LEDs.
Figure 10:
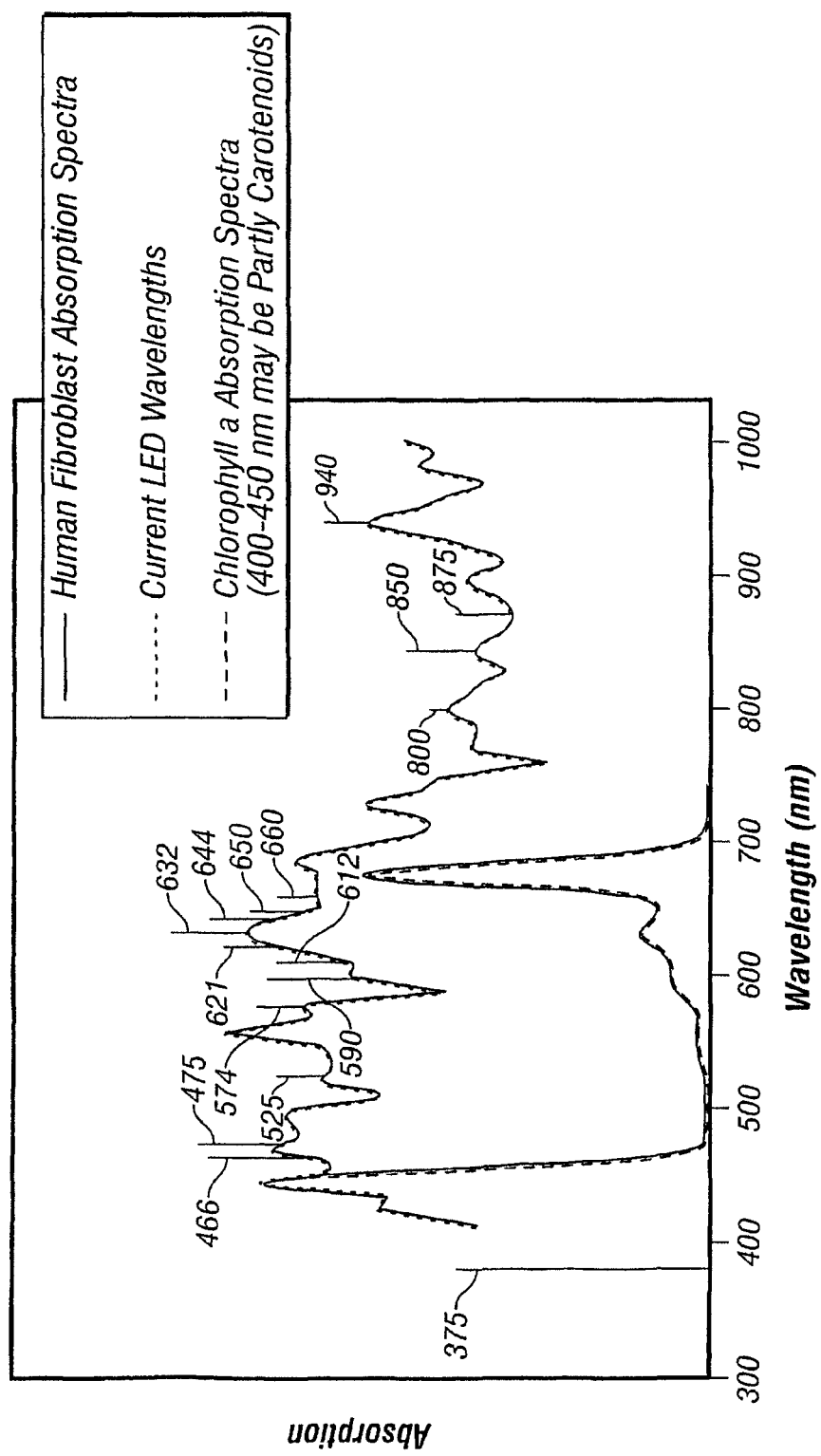
Figure 11:
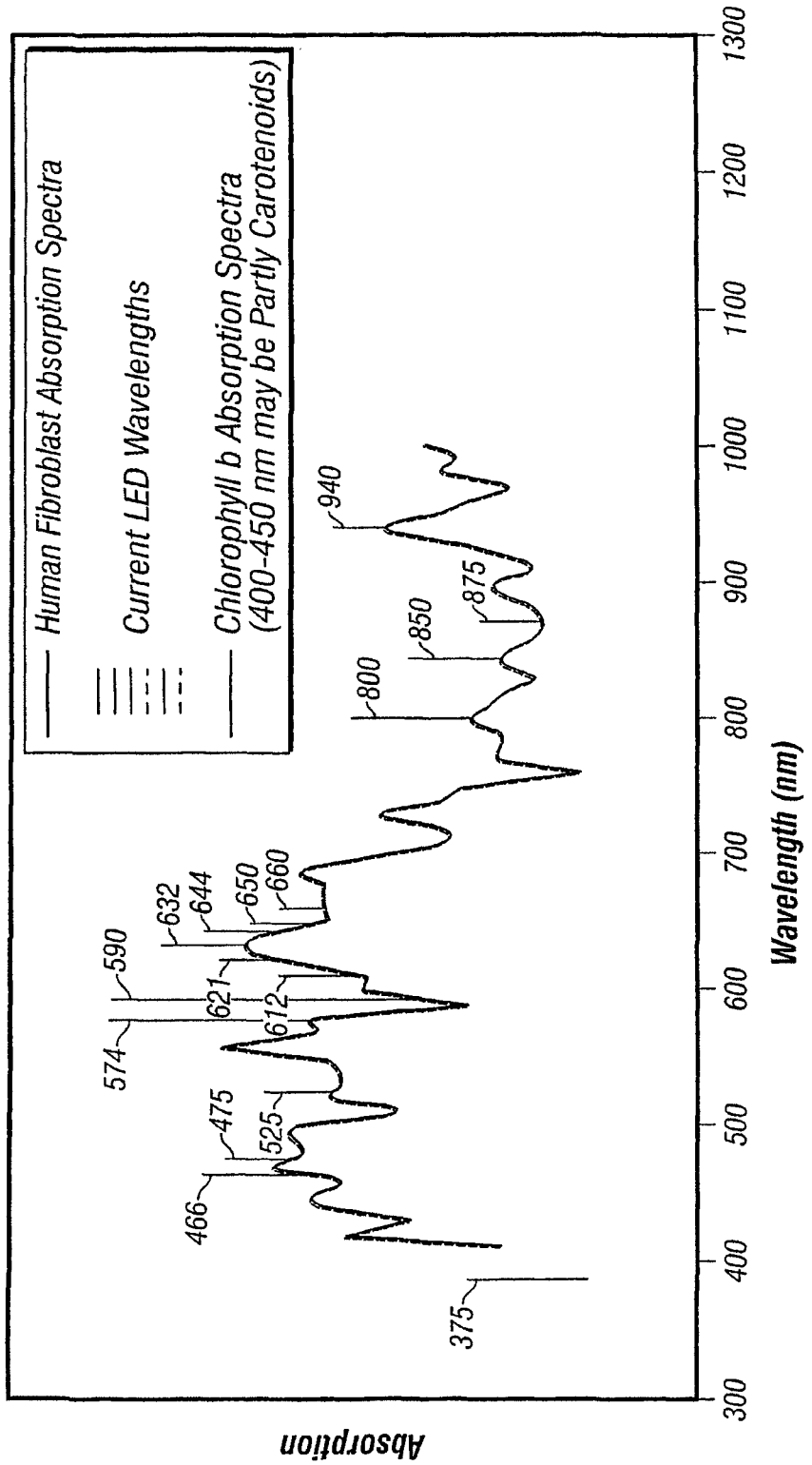
FIG. 11 shows the absorption spectrum for human fibroblast overlayed with the wavelengths of various, commercially produced LEDs, and also the absorption spectrum of chlorophyll b.
Figure 12:
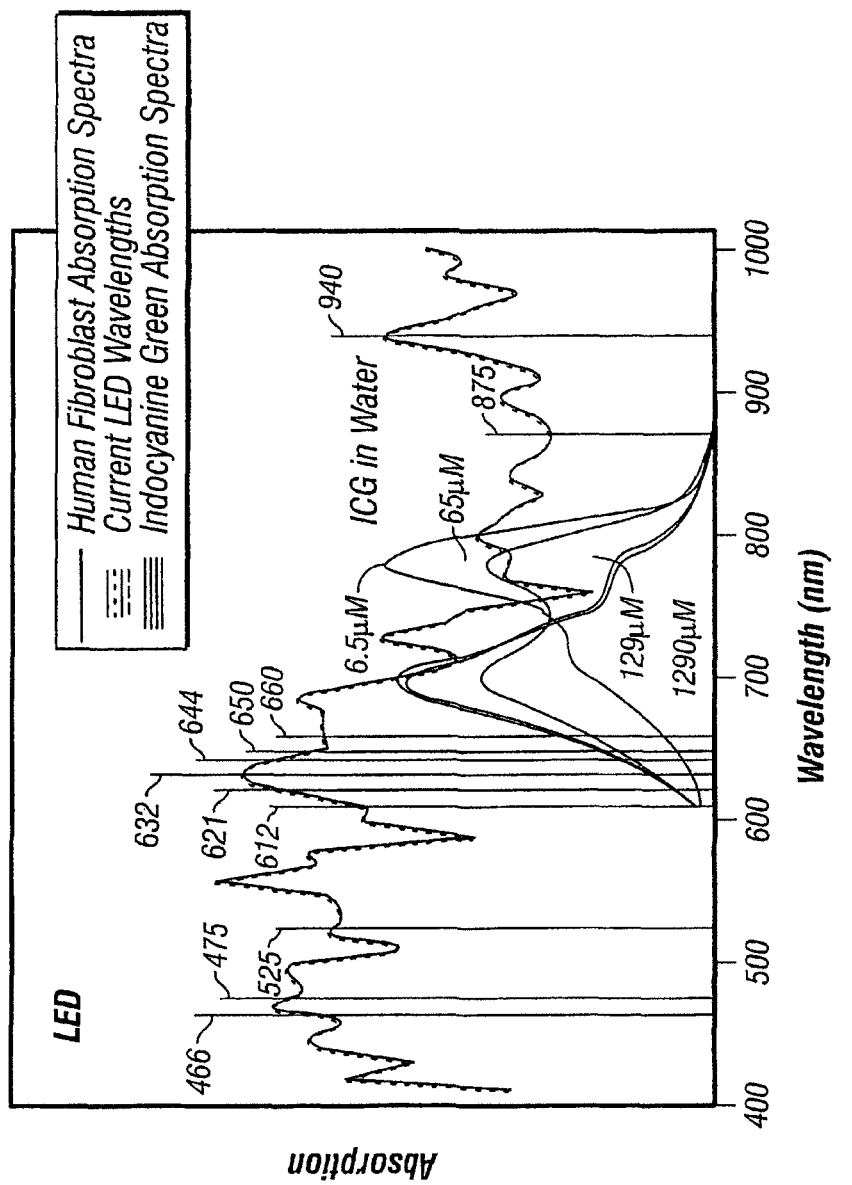
FIG. 12 shows the absorption spectrum for human fibroblast overlayed with the wavelengths of various, commercially produced LEDs, and also the absorption spectrum of indocyanin green.
Figure 13:
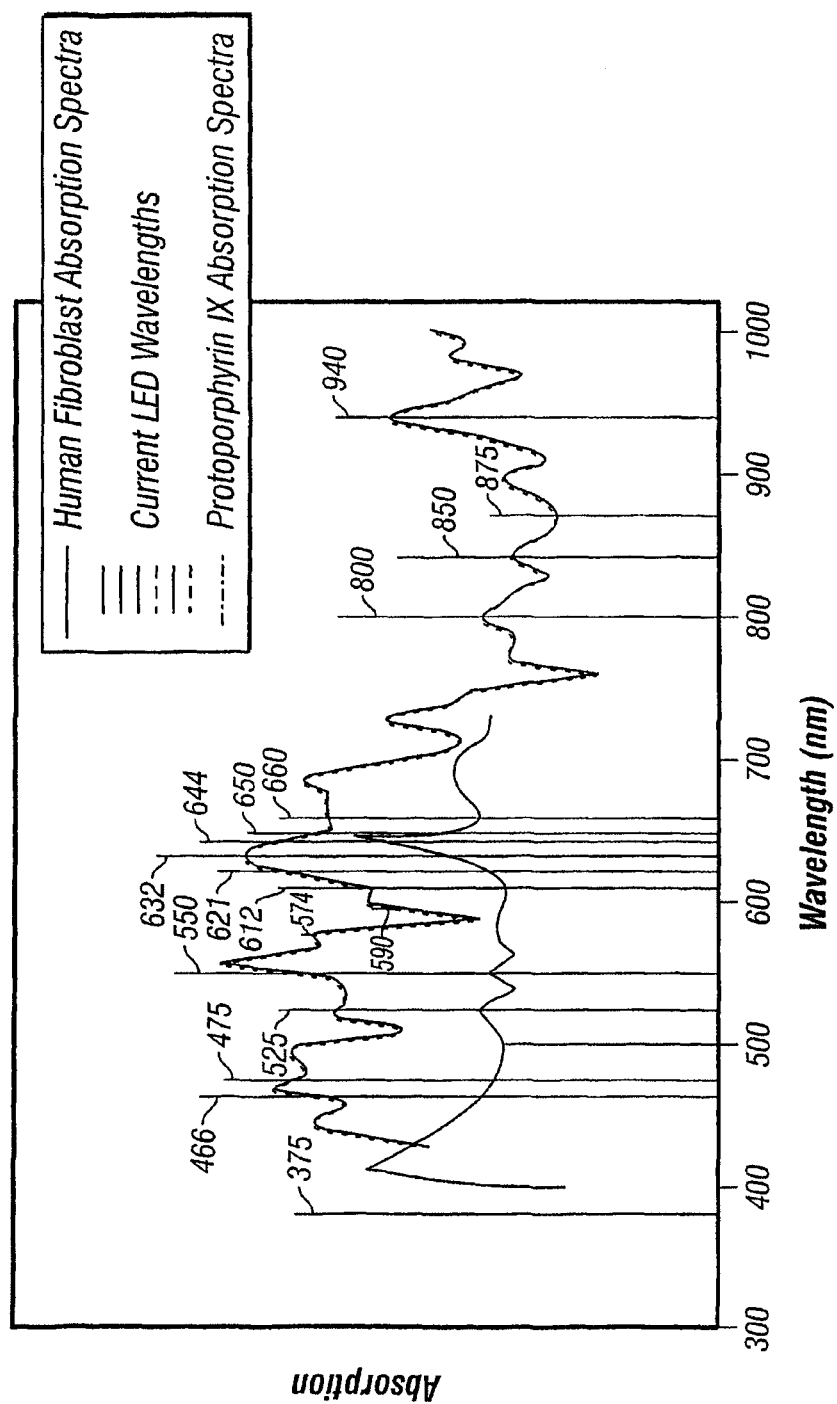
FIG. 13 shows the absorption spectrum for human fibroblast overlayed with the wavelengths of various, commercially produced LEDs, and also the absorption spectrum of protoporphryin IX.

One preferred embodiment uses the transdermal application of chlorophyll to the sebaceous oil gland and surrounding tissue. The chlorophyll is then exposed to a source of electromagnetic radiation such as from a laser, an LED, a flash-lamp, or other source filtered to provide a dominant wavelength of from about 400 to about 450 nm. Other preferred wavelengths include from about 360 nm to about 440 nm and, with greater preference, from about 380 nm to about 420 nm. Pulse durations may be selected with sufficient power density to allow the target tissue to be appropriately inhibited to reduce acne bacteria content and to reduce or destroy gland activity through photomodulation and photothermal means. While blue light is used for illustrative purposes, it has been found that red light is also effective in accordance with the present invention. Generally, one skilled in the art will recognize to choose a light wavelength for treatment in the range of about 300 nm to about 1400 nm based on the absorption spectrum of the chromophore or other light-activated topical composition used. FIG. 7 shows the absorption spectrum for 0.03% Na Cu Chlorophyllin in deionized water. The primary absorption peak is shown to be at around 400 nm. This would indicate that for this chromophore, the most suitable wavelength for photomodulator and/or photothermal treatment would be at around 400 nm. Another absorption peak occurs at around 620 nm, thus in an instance where a light source with a dominant wavelength of around 400 nm was not available, a light source with a dominant wavelength of around 620 nm could be used. This figure further illustrates the absorption spectra of a carotenoid with a broad absorption band from 400 nm to 520 nm. This allows use of more wavelengths including those of green light (500 nm to 520 nm). A comparison of the absorption spectra of various naturally occurring chromophores is shown in FIG. 8.

One acne treatment process uses a solution of graphite in a carrier solution and a Q-switched 1064 nm ND:YAG laser. The solution may be applied to the skin which is then treated with the laser using known parameters. It may be preferable to use a high repetition rate and move the laser handpiece slowly enough that pulses are "stacked" in one spot for several pulses before the handpiece is moved to an adjacent spot. It has been found that there is a stair-step like effect of incremental temperature rise in the sebaceous glands with the second and third pulses versus a single pulse. A faster repetition rate also tends to help build the heat up faster, and to higher levels. This tends to produce the maximum heat (which is desirable, as long as the heat stays confined to the sebaceous glands and the immediately adjacent supporting tissues). Since this effect occurs substantially simultaneously with other destructive effects of the process, the damage to sebaceous glands tends to be enhanced. Unlike carbon exploded particles on light impact, the dyes and similar agents may actually remain absorbing for a brief time until they reach a critical temperature at which time they are destroyed or become non absorbers, thus acting as a sort of heat sink for a brief time, allowing more heat to accumulate than with carbon solutions and short pulsed Q-Switched lasers. Safety remains at about the same level, since dye related damage tends to be confined to target tissues. There is no appreciable change in patient treatment time.

Another preferred embodiment uses a longer pulsed laser in the 750 nm-1000 nm range and appropriate parameters to achieve the desired tissue damage goal.

Another embodiment uses a tissue dye which attaches to, or is incorporated into, a target cell and surrounding tissues. The target tissue may be illuminated with a multi-wavelength non-laser light source using appropriate parameters to achieve the desired tissue damage goal.

Another embodiment uses a light source which is well-absorbed by the melanin naturally present in skin and undyed darker hairs. Natural or synthetic melanin or derivatives thereof will be well-absorbed by the same wavelength of light (or alternatively two or more wavelengths, one for melanin and one or more for the dye). This melanin agent is delivered into the sebaceous gland, duct, or supporting tissue, resulting in an enhanced or greater injury to the target tissue (or permitting lower treatment energy parameters, resulting in safer treatment than if the sebaceous gland, duct, or supporting tissue were treated without the melanin dye). This tends to benefit people having darker skin or tanned skin, by allowing lower treatment energy. For example, a diode laser or LED or non-laser light source could produce a continuous or pseudo-continuous beam of light energy using pulse durations as long as seconds at a wavelength which is absorbed by the light-activated chromophore, native porphyrin containing acne bacteria porphyrin compound, or native sebaceous gland, duct, or supporting tissue pigment and also by the melanin or dye used. A pulse duration on the order of between about one and thirty seconds appears to be preferable. This also tends to be a much longer time than is used in most systems in use today.

Another embodiment uses an agent which facilitates cavitation shock waves or a thermal effect or both. This preferentially damages (or stimulates) the target tissues while minimizing damage (or other adverse effects) on surrounding non-target tissues. This may be used with very short pulsed lasers or light sources or with ultrasound alone.

In one embodiment a process in accordance with the present invention may be used to provide short or long-term control, improvement, reduction or elimination of acne or other related skin diseases. An active agent may be physically or chemically or immunologically incorporated into cells of the sebaceous (oil) glands, ducts, or supporting tissue, or into the naturally occurring acne bacteria, porphyrin compounds, naturally occurring light activated chromophores, yeast or similar organisms which feed on the oil in the oil glands (or sweat glands) or exists in the oil or oil glands as otherwise relatively benign inhabitants. Some acne bacteria may not inhabit all sebaceous structures and other strains may not produce native porphyrins to target with light. Other acne bacteria may be located deeper than 400 nm to 420 nm light can adequately penetrate, thus treatment with light alone may be only partially effective in clinical treatment. Improvement in skin disorders may be a direct or indirect result of the application of the agents in this process, as may reduce oiliness of the skin, reduced size or diminished appearance of pores, etc. The present invention is also useful for treating enlarged pores, oily skin, and other disorders where there is no active acne-related disorder.

Other similar disorders such as folliculitis which involve the pilosebaceous (hair/oil gland) unit may also be treated using the present invention. The present invention may also be used to reduce perspiration, sweating, or hyperhidrosis from eccrine (sweat) glands or apocrine glands. A preferred embodiment of the present invention may be used to treat other skin disorders such as, for example, viral warts, psoriasis, precancerous solar keratosis or skin lesions, hyperhidrosis/excessive sweating, aging, wrinkled or sun damaged skin, and skin ulcers (diabetic, pressure, venous stasis).

Scarring is commonly seen as a consequence of disorders, diseases, or dysfunctions of the sebaceos apparatus. Scarring may consist of one or more of the following: raised hypertrophic scars or fibrosis, depressed atrophic scars, hyperpigmentation, hyperpigmentary redness or telangectasia. Photomodulatory, photochemical, or photothermal treatments alone, or in combination with exogenous or endogenous chromophores, or combinations thereof, can be used simultaneously, sequentially, etc., as described herein for the treatment of sebaceous gland disorders, diseases, or dysfunctions. Further, as herein described, the term photomodulation refers to the treatment of living tissue with light along, heat emitted by a light source, or light-activated chemical compositions, or any combination thereof. Falling within the scope of photomodulatory treatments are photothermal treatment, photoactivation, photoinhibition, and photochemical treatment of living tissue and, in particular, sebaceous structures within human skin. Further, electromagnetic emitters of the present invention can fall into three categories: those which emit light in the visible spectrum and are useful for photoactivation and photoinhibition photomodulatory process; those that emit light in the ultraviolet spectrum and are also useful for photoactivation and photoinhibition photomodulatory process; and those that emit light in the infrared region and permit photomodulation treatment to be carried out through photothermal means, i.e., heat activation of the exogenous chromorphore, living cells or tissue, or both.

A preferred embodiment of the present invention may use various microencapsulation processes to deliver active agents. If the diameter of the micro encapsulations is about five microns, then there may be relatively site specific preferential delivery into the sebaceous oil glands or skin surface stratum corneum cells. If the diameter of the microencapsulations is in the range of about one micron, then the active agents may be delivered with a more random distribution between the hair ducts and the oil glands. If the diameter of the microencapsulations is larger, on the order of about 20 microns or greater, then delivery will tend to be restricted primarily to the skin surface. The micro encapsulations may be synthetic or natural. If ultrasound is used to enhance penetration, then the diameters and ultrasound treatment parameters may need to be adjusted according to the applicable principles which allow the estimation of the optimal ultrasound parameters for driving small particles into the skin, skin appendages or skin orifices.

Microencapsulation may be used to improve delivery of known agents such as chlorophyll, carotenoids, methylene blue, indocyanine green and particles of carbon or graphite. A known technique for using a laser to produce a wavelength that may be absorbed by indocyanine green for a hair removal treatment process is described, for example, in U.S. Pat. No. 5,669,916, which is incorporated by reference. It has been found that by using smaller particles and putting the smaller particles into more uniform diameter microencapsulations, more site specific or uniform targeting may be achieved. A preferred formulation may include indocyanine green or other dyes or agents to form a lipid complex which is fat-loving (lipophilic). The delivery and clinical effects of agents and dyes such as indocyanine green dye may be refined and enhanced by selecting a carrier or encapsulation having a diameter that increases the probability of preferential delivery to a desired space, and/or that enables interaction with ultrasound to thereby increase the probability of preferential delivery, and/or that selectively attaches to the sebaceous gland, duct, supporting tissues, oil itself or bacteria, yeasts, or other organisms residing within these tissues.

Indocyanine green dye is presently in medical use, appears to be relatively benign, may be activated by red visible lasers, or other source of monochromatic or multichromatic light, (in the 800 nm range) may penetrate deeply enough to reach the oil glands, is used for leg vein and hair removal, and is relatively safe, cheap, and reliable. A known technique for using a laser to produce a wavelength that may be absorbed by indocyanine green for use in a leg vein treatment process is described, for example, in U.S. Pat. No. 5,658,323, which is incorporated by reference. Methylene blue has also been used according to the present invention with good success.

The microsponges containing the active agent may selectively attach, or at least have a chemical affinity for, some part of the oil gland. The ICN dye may be conjugated with lipids, which would then have an affinity for the oil glands. Alternatively, the attachment may occur after the active agent is released from the microsponge, either passively or by attractive or chemical forces. In the case of some microencapsulation carrier vehicles, release may occur after disruption of the vehicle integrity itself, possibly by ultrasound or laser or light or other energy source or perhaps a chemical reaction.

In a preferred embodiment the ICN dye may be mixed with lipids, or put into microsponges (a.k.a. microspheres), and then applied to the skin surface, allowed to sit for a time. Excess dye may be removed, and then the area may be treated with laser light at about 800 nm, between about 0.1 and 100 millisec pulses and around 1.0-10.0 Joules/cm$^2$.

U.S. Pat. No. 5,817,089 specifies "particles having a major diameter of about 1 micron". It has been discovered, however, that these diameters may not be optimal. A 1993 Pharmaceutical Research journal article by Rolland et al describes an acne treatment wherein a topical acne drug is delivered with less irritation by putting the drug into synthetic polymer microsphere sponges. This article reported that an optimal diameter for site-specific delivery into sebaceous oil glands in the skin was about 5 microns, and that 1 micron particles randomly delivered to the hair follicle and stratum corneum.

Most agents may not inherently be the optimal size. However, virtually any agent may be preferentially delivered to the sebaceous glands by either synthetic microspheres, or liposomes, or albumen microspheres, or other similar "delivery devices".

In a preferred embodiment for treatment of acne, graphite particles having an average diameter of about one micron may be placed in delivery devices, such as microsponges, having an average diameter of about five microns. The microsponges may then be suspended in a lotion. Ultrasound may be used to drive the particles into the skin. The optimal ultrasound parameters may be based on the outside particle diameter (especially if particles are uniform). Selective delivery of the particles to hair and perhaps to sweat glands may be improved.

Use of such applications could enable selective delivery of anti-acne agents, or hair dye for laser hair removal, or agents which stimulate hair growth, or other hair treatments, where the encapsulation diameter was used, with or without ultrasound, to preferentially deliver, and ultrasound at different parameters or laser was used to release (not necessarily to activate or interact).

These techniques may be applied to many other agents in addition to ICN dye and graphite lotions. The term "encapsulated delivery device" is used herein as a generic term which encompasses all such possible items.

Pressure may be used to impel particles (i.e., graphite, carbon, or other active agent or skin contaminant particulates) into the skin, either in the spaces between the stratum corneum, into the hair ducts and hair follicles, the sebaceous oil glands, or other structures. Air pressure or other gases or liquids may be used to enhance delivery or increase the quantity of delivered agent. A known technique for using an air pressure device for removing skin surface is described, for example, in U.S. Pat. No. 5,037,432, which is incorporated by reference.

Ultrasound may be used to physically deliver hair dye and to enhance penetration into the hair shaft itself (see, for example, U.S. Pat. No. 5,817,089, incorporated herein by reference). The use of ultrasound to physically drive graphite particles down for the treatment of unwanted hair or acne appears to have been suggested in the prior art. However, the applicant is aware of no prior art disclosure or suggestion of: (1) the use of ultrasound to enhance the penetration of an agent into the hair shaft itself, or into surrounding cells; (2) the use of ultrasound to drive graphite particles into spaces between the stratum corneum to enhance the effects of a skin peel process (which physically removes a portion of the outer layers of the skin surface); or (3) physically removing the hair by methods such as waxing or pulling and then injecting the treatment composition, i.e., the chromophore or other topical composition, into the sebaceous gland or duct. Such methods are contemplated in one embodiment of the invention.

A known skin peel process may be improved by using ultrasound to open intercellular spaces in the outer stratum corneum layer of the skin via cavitation. Then an active agent may be driven in further with the same or similar ultrasound. Fibroblast stimulation may be optimized with both topical agents that are applied afterwards (while the skin is still relatively permeable) and also with additional low level light stimulation.

The processes described above may be used to deliver two different agents, either serially or simultaneously. The two agents may then be activated by the light source together to work synergistically, or to combine and then have an effect, or to deliver two different agents that may be activated simultaneously or very closely in time. Two different light sources or wavelengths may be used serially or simultaneous to have different effects such as treating active acne lesions and also acne scarring; treating acne rosacea lesions and alos rosacea blood vessels or telangectasia; or using photothermal means for active acne and nonthermal photomodulation for treating acne scarring or skin wrinkles.

Two entirely different laser, LED, or light beams may be delivered substantially simultaneously through the same optics at different parameters. For example, one beam may be delivered primarily to release or to activate, and a second beam primarily to treat. Additive effects may be achieved by using two beams at the same time, such as the use of blue light with a wavelength of approximately 400 nm and red light with a wavelength of approximately 600 nm. For example, a known process for skin peel and hair reduction may be optimal at 1064 nm for safety and for treating all skin colors, but other wavelengths may be better to achieve a low level laser stimulation of fibroblasts. Acne reduction is achieved by this process, as well, using lasers or LEDS as the low-level light source at a wavelength chosen according to the absorption spectrum of the topical composition used. Particularly preferred for topical compositions are those comprising naturally occurring chlorophyll-containing compounds, carotenoid-containing compounds, derivatives thereof, and mixtures thereof, as well as derivatives, analogs, and genetically engineered forms of such agents.

A hand-held device containing the low-level light source may be used to photomodulate or photothermally activate, or both, the living tissue or active ingredient in the topical composition, or both, for skin peel, hair reduction, or acne reduction, and either simultaneous or synchronized sequentially in time to deliver another wavelength that may be optimal to in view of the absorption characteristics of the patient's fibroblast spectrum or the spectrum of the topical composition. In the one case it may be the best wavelength to stimulate fibroblasts. In another case it may allow selection of a melanin or dye (or other agent) having very strong affinity for the sebaceous gland and very strong absorption at the wavelength used for treatment.

There are a wide variety of different operating parameters that may comprise conditions effective to produce beneficial cellular effects such as triggering cellular regeneration or photoactivation or photoinhibition which, for example, could reduce the activity of, or even destroy, oil glands in the skin, thereby indirectly reducing acne bacteria. Also, it is preferable to target a natural chromophore for photoactivation or photoinhibition, each falling under the general term photomodulation is possible for directly treating the naturally occurring porphyrin compounds in acne bacteria, in addition to targeting exogenous chromophores like carotenoids, chlorophyll and its derivatives including copper chlorophyllin and other dyes such as indocyanine green dye, methylene blue dye, and similar compositions known to those skilled in the art. Further photothermal modulation of the oil glands and surrounding tissue can be accomplished via the same means as described above, although the operating parameters may vary. The difference being that photothermal treatment uses heat to induce minor to moderate amounts of thermal injury to the gland or surround tissue to reduce the activity of the target tissue or destroy it altogether.

Exogenous chromophores are substances which absorb light or electromagnetic radiation in at least one narrow band of wavelengths and assist with the treatment method and system of the present invention by applying them to an area of the skin to be treated. Selection of the exogenous chromophore is determined by the absoroption spectra of the chromophores and is dependent on the wavelength of the narrowband multichromatic emitter used for treatment. In accordance with a preferred embodiment of the invention, the chromophore will aid in treatment by enabling at least the dominant or central wavelength of the narrowband, multichromatic radiation to penetrate at least the stratum corneum layer of the skin and permitting the photomodulation or photothermal injury or destruction of living tissue, sebaceous oil gland, duct, or supporting tissue in and below the stratum corneum. In some instances, the photomodulated tissue can be below all of the epithelial layers of the skin.

Some examples of possible operating parameters may include the wavelengths of the electromagnetic radiation to which the living tissue containing cells to be regenerated, stimulated, inhibited, or destroyed, the duration of pulses (pulse duraction) of the electromagnetic radiation, the number of pulses, the duration between pulses, also referred to as repetition rate or interpulse interval. Intervals between treatments can be as long as hours, days, weeks, months, etc.; and the total number of treatments is determined by the response of the individual patient. Further, treatment regimens using a combination of more than one wavelengths either simultaneous or in sequence may be used. As well, the energy intensity of the radiation as measured at the living tissue (typically measured in Joules per centimeter squared, watts per centimeter squared, etc.), the pH of the cell, tissue or skin, the skin temperature, and time from application to treatment with a light source, if used with exogenous chromophore (which can be topical, injected, driven in with ultrasound, or systemic) is determined by the nature of the treatment and is further illustrated in the Examples.

Figure 3A:
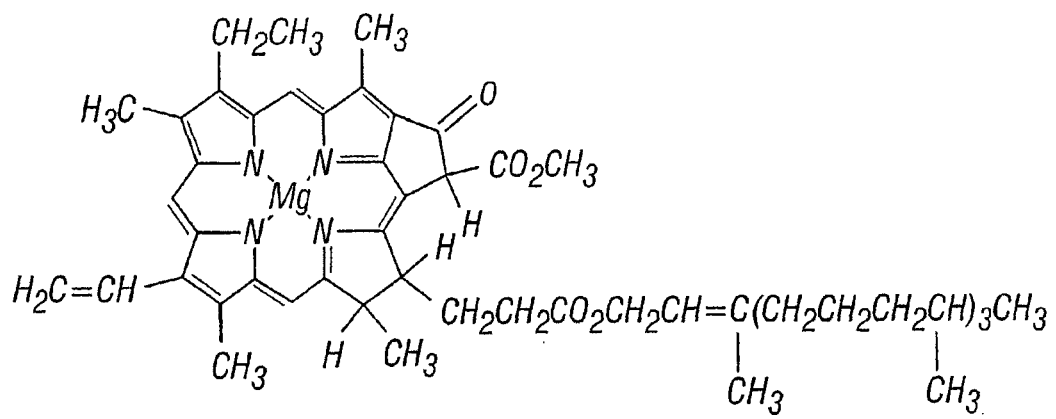
FIG. 3a is a representation of the general chemical structure of a chlorophyll molecule.
Figure 3B:
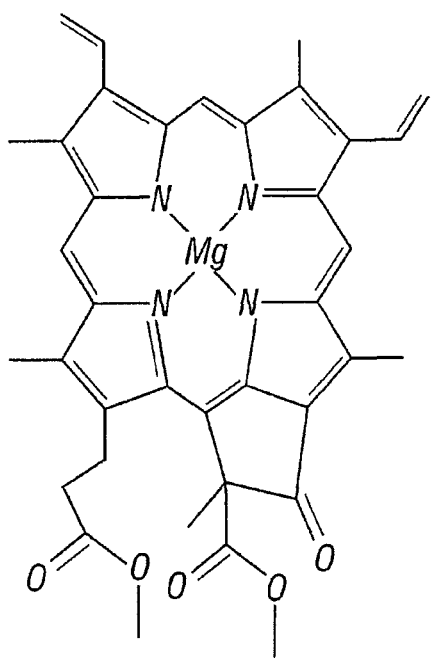
FIG. 3b shows the structure of chlorophyll b.

Wavelength—Each target cell or subcellular component, or molecular bond therein, tends to have at least one unique and characteristic "action spectrum" at which it exhibits certain electromagnetic or light absorption peaks or maxima FIG. 3, for example, shows the absorption spectrum of one line of human fibroblast cells in monolayer tissue culture. Different cell lines (of the same cell—for example fibroblasts from 3 different patients) exhibit some differences in their absorption spectra and thus using narrow band multichromatic light (rather than monochromatic light) is also useful in producing the optimal clinical effect. When these cells or subcellular components are irradiated with wavelengths corresponding to the absorption peaks or maxima, energy is transferred from the light photon and absorbed by the target. The particular features of the delivered energy determine the cellular effects. The complexity of these combinations of parameters has produced much confusion in the prior art. Basically, the wavelength should roughly correlate with an absorption maxima for the target cell or subcellular component or tissue, or exogenous chromophore. In some cases it may be desirable to target more than one maxima—either simultaneously or sequentially on the same or different treatment dates. The presence of multiple maxima action spectra are common for a given cell or subcellular component or exogenous chromophore and different wavelength maxima irradiation may produce different results.

If the wavelength band is overly broad, then the desired photomodulation effects may be altered from those intended. Consequently, use of broad band noncoherent intense light sources may be less desirable than those specified for use with the present invention, in contrast to the use of multiple narrowband emitters. The laser diodes are also multichromatic with narrow wavelength bands around a dominant band, i.e., they are narrowband multichromatic devices—devices which emit electromagnetic in a narrow band of radiation either symetrically or asymetrically around a dominant wavelength. For purposes of the present invention, any device that emits electromagnetic radiation in a bandwidth of +/−about 100 nanometers around a dominant wavelength can be considered to be a narrowband, multichromatic emitter. LEDS, while not monochromatic, emit in such a narrow band as to be considered narrowband multichromatic emitters. The narrow band allows photons of slightly different wavelengths to be emitted. This can potentially be beneficial for creating certain desirable multi photon interactions. In contrast, most commercial lasers emit light at a single wavelength of light and are considered monochromatic. The use of lasers, according to the prior art, has relied upon the coherent, i.e., monochromatic, nature of their electromagnetic emissions.

Wavelength may also determine tissue penetration depth. It is important for the desired wavelength to reach the target cell, tissue or organ. Tissue penetration depth for intact skin may be different than the tissue penetration depth for ulcerated or burned skin and may also be different for skin that has been abraded or enzymatically peeled or that has had at least a portion of the stratum corneum removed by any method. It is also important to penetrate any interfering chromophore that also absorbs at this same wavelength (e.g. dark ethnic skin, plastic Petrie dishes for tissue or cell culture, etc.). It is important to penetrate any tissues or organs in its pathway.

For example, light having a dominant wavelength emission in the range of about 400 nm to about 420 nm has such a short wavelength that not all sebaceous glands or acne cysts can be effectively treated due to the limited depth of penetration of the radiation, whereas light having a wavelength of about 600 nm to about 660 nm can more easily penetrate to a greater depth, if treatment of the lower dermal layers or even deeper is desirable. Accordingly, the selection of the dominant wavelength of the radiation emitter is also dependent on the depth of treatment desired. The selection of the proper wavelength is one of the significant parameters for effective use of the present invention, but others are important as well:

Energy Density—The energy density corresponds to the amount of energy delivered during irradiation and is also referred to as energy intensity and light intensity. The optimal 'dose' is affected by pulse duration and wavelength—thus, these are interrelated and pulse duration is very important—in general high energy produces inhibition and lower energy produces stimulation.

Pulse duration—The exposure time for the irradiation is very critical and varies with the desired effect and the target cell, subcellular component, exogenous chromophore tissue or organ. (e.g. 0.5 microseconds to 1 0 min may be effective for human fibroblasts, though greater or lesser may also be used successfully).

Continuous Wave (CW) vs. pulsed—e.g. the optimal pulse duration is affected by these parameters. In general, the energy requirements are different if pulsed mode is used compared to continuous (CW) modes. Generally, the pulsed mode is preferred for certain treatment regimen and the CW mode for others.

Frequency (if pulsed)—e.g. higher frequency tends to be inhibitory while lower frequency tends to be stimulatory, but exceptions may occur.

Duty cycle—This is the device light output repetition cycle whereby the irradiation is repeated at periodic intervals, also referred to herein as the interpulse delay (time between pulses when the treatment session comprises a series of pulses).

Suitable active agents for use in topical compositions applied to the skin in accordance with the present invention include one or more of Vitamin C, Vitamin E, Vitamin D, Vitamin A, Vitamin K, Vitamin F, Retin A (Tretinoin), Adapalene, Retinol, Hydroquinone, Kojic acid, a growth factor, *echinacea*, an antibiotic, an antifungal, an antiviral, a bleaching agent, an alpha hydroxy acid, a beta hydroxy acid, salicylic acid, antioxidant triad compound, a seaweed derivative, a salt water derivative, algae, an antioxidant, a phytoanthocyanin, a phytonutrient, plankton, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, Rogaine, a hair growth stimulating substance, a hair growth inhibiting substance, a dye, a natural or synthetic melanin, a metalloproteinase inhibitor, proline, hydroxyproline, an anesthetic substance, chlorophyll, bacteriochlorophyll, copper chlorophyllin, chloroplasts, carotenoids, phycobilin, rhodopsin, anthocyanin, and derivatives, subcomponents, immunological complexes and antibodies directed towards any component of the target skin structure or apparatus, and analogs of the above items both natural and synthetic, as well as combinations thereof.

While not a limiting factor, a common aspect of the most useful natural chromophores of the present invention is found in their chemical structure. Naturally occurring chromophores have a metal-ligand bonding site. FIG. 2 illustrates the chemical structure of chlorophyll a, characterized by $R=CH_3$. A magnesium atom is present at the metal-ligand bonding site in the Figure. Chlorophyll a exhibits absorption maxima at 409 nm, 429 nm, 498 nm, 531 nm, 577 nm, 613 nm, and 660 nm. Chlorophyll b is characterized by $R=CHO$ exhibits absorption maxima at 427 nm, 453 nm, 545 nm, 565 nm, 593 nm, and 642 nm. It can be readily seen that various types of chlorophyll, or combinations thereof, can be used as topically applied chromophores to assist the absorption of certain wavelengths of light delivered through the skin or soft tissue for various treatments. When used to enhance the absorption of a wavelength of light that coincides with an absorption maxima of target cells such as human fibroblasts, treatment can be even more effective or can be carried out with reduced light intensities or can produce multiple beneficial effects, such as treating acne bacteria and reducing or eliminating acne scarring.

The alkaline hyrolysis of chlorophyll opens the cyclopentanone ring and replaces the methyl and phytyl ester groups with sodium or potassium. These resulting salts are called chlorophyllins and are water soluble. The alkaline hydrolysis of the chlorophyll shown in FIG. 2 will result in a NaMg Chlorophyllin, but other salts can easily be formed by replacing the Mg atom in the chlorophyll with other metals or reactive transition metals, for example, such as copper, aluminum, iron, metal chelates, or antibody complexes. Such a substitution is made by treating the chlorophyll with an acid causing the Mg to be removed and replaced by $H_2$ which, in turn, is easily replaced by other metals.

Unlike artificially synthesized chromophores, naturally occurring chromophores bear the similar attribute of having the metal ligand bonding site which will dissociate the metal ion upon treatment with an acid. The acid content of human skin is sufficient to trigger this reaction and, in turn, cause the chlorophyll, having lost the metal ion, to become less soluble in water. The resulting chlorophyll, or other naturally occurring agent that dissociates a metal ion from a ligand bond under acidic conditions such as porphyrin for example, makes an excellent topical composition with superior optical properties for acting as a chromophore to enhance low-intensity light therapies. In another embodiment of the invention, therefore, the preferred chromophore is a compound having a metal ligand bond that dissociates the metal ion under acidic conditions. In one embodiment of the invention, topical skin care formulations may be used for altering the pH or acidity of the skin.

In addition to being an effective treatment method for reducing and eliminating the presence of common acne bacteria such as *acnes vulgaris* and for safely treating conditions such as pseudofolliculitis barbae, acne rosacea, and sebaceous hyperplasia, the present invention also has application to the reduction of cellulite. Using any of the light sources suitable for use as described herein, adipocyte cells can be photomodulated. Photomodulation increases the local microcirculation in the cellulite and alters the metabolic activity of the cells. Enhanced local microcirculation, metabolism or enzymation activity, or combinations thereof, may be produced by photomodulatory means. To enhance the treatment, any of the topical chromophores as previously described can be used or non-chromophoric compositions can be used in conjunction with any of the photomodulatory methods, including low-intensity light therapy. Further photothermal means may be used to destroy adipocyte cells alone or in combination with photomodulatory means, with or without the use of exogenous chromophores.

Many living organisms—both animals and plants—have as one of their major defense mechanisms against environmental damage to their cells and DNA repair system. This system is present in many if not all living organisms ranging from bacteria and yeasts to insects, amphibians, rodents and humans. This DNA mechanism is one which is involved in processes to minimize death of cells, mutations, errors in copying DNA or permanent DNA damage. These types of environmental and disease and drug related DNA damage are involved in aging and cancer.

One of these cancers, skin cancer, results from ultraviolet light damage to the DNA produced by environmental exposure to natural sunlight. Almost all living organisms are unavoidably exposed to sunlight and thus to these damaging UV rays. The damage which is produced is a change in the structure of the DNA called pyrimidine dimmers. This causes the DNA structure to be altered so that it cannot be read or copied any longer by the skin cells. This affects genes and tumor development and proper functioning of the immune system.

An enzyme called photolyase helps to restore the original structure and function of the damaged DNA. Interestingly photolyases are activated by light to then act to repair the DNA damaged by ultraviolet light. In the dark it binds to the cyclobutane pyrimidine dimmer created by the UV light and converts it into two adjacent pyrimidines (no dimer connecting these any longer) and thus the DNA damage is repaired. This direct reversal of DNA damage is called "photoreactivation". The photolyase upon exposure to blue light absorbs the light energy and uses this energy to 'split' the dimer and thus restore the normal DNA structure. Other mechanisms of DNA repair exist as well.

The photolyase repair mechanism is not well understood at present, but naturally occurring or synthetic or genetically engineered photolyase from essentially any living organism source can be utilized for other organisms including human and veterinary and plant applications. DNA damage produced by factors other than ultraviolet light may also be repaired including, but not limited to, such factors as other environmental damage or toxins, radiation, drugs, diseases, chemotherapy for cancer, cancer, microgravity and space travel related damage, and a myriad of other causes.

The use of such naturally derived or artificially created or genetically engineered photolyase enzymes or related enzymes or other proteins functioning for DNA or RNA repair have a wide variety of applications. For example, the ability to treat skin damaged by sunlight/ultraviolet light of disease and to repair, reverse, diminish or otherwise reduce the risk of skin cancer could be used either as a therapeutic treatment or as a preventive measure for people with severely sundamaged skin, with precancerous skin lesions, or with skin cancer.

This principle applies not only to skin cells and skin cancer but to a very broad range of skin and internal disorders, diseases, dysfunctions, genetic disorders, damage and tumors and cancers. In fact potentially any living cells might have beneficial effects from treatment with photolyase or similar proteins in combination with light therapy.

While in nature the light to activate the photolyase typically comes from natural sunlight, essentially any light source, laser and non laser, narrow band or broader bandwidth sources can activate the photolyase if the proper wavelengths and treatment parameters are selected. Thus natural sunlight filtered through a selective sunscreen could be used to activate both native and exogenously applied photolyases. Another treatment option would be to apply the photolyase and then treat with a controlled light source exposure to the proper wavelength band and parameters. A wide variety of light sources could be utilized and the range of these is described elsewhere in this application. For example a low energy microwatt narrow band but multi-spectral LED light source or array with mixed wavelengths could be utilized. Another embodiment is a filtered metal halide light source with a dominant wavelength of 415 nm+/−20 nm and an exposure of 1-30 minutes at 1-100 milliwatts output can be utilized. Such exposure would occur minutes to days after application of a topical product containing photolyase.

Another example would be the repair of cells in the skin which have environmental damage but instead of repairing the cells which lead to skin cancer the cells which lead to aging (photoaging) of the skin are targeted for this therapy. In one embodiment, kin fibroblasts which have been sun damaged are treated with a photolyase and subsequently the photolyase is photomodulated with blue light to set in motion the DNA repair mechanism of photolyase—that is photoreactivation. This allows the repair of the structure and thus the normal functioning of the fibroblast DNA thus allowing normal functioning and proliferation of these fibroblasts—which produce the proteins such as collagen and elastin and hyaluronic acid and matrix ground substance which cause skin to be firm and elastic and youthful in appearance—thus producing anti-aging or skin rejuvenation effects in the skin as well as improving the structure and healthy function of the skin.

Various cofactors which are involved in this photoreactivation process can also be added either topically or systemically to further enhance or improve the efficiency of this process. Other cofactors needed in the production of these proteins once the cells recover normal function also may be added topically or systemically to enhance the anti-aging or skin rejuevenation process. The delivery of both the photolyase and/or the cofactors described above can be enhanced by utilizing ultrasound to increase skin permeability or to increase transport across the skin barrier and into the skin and underlying tissues. Removal of a portion of the stratum corneum of the skin can also be used, alone or incombination with ultrasound, to enhance penetration and delivery of these topically applied agents. Additionally such methods of removing or altering the stratum corneum can assist in penetration of the light or the efficiency of same or allow use of lower powered light sources including home use devices such as battery powered LED sources.

A variety of sources exist for obtaining photolyases. These may include native naturally occurring photolyases, compounds derived from other living organisms (that is one may use for example bacterially derived, or yeast derived, or plankton rederived, or synthetic or genetically engineered, etc., photolyases and use them in human skin for beneficial effects thus not limited to same species derived photolyases. One known photolase is derived from *Anacystis nidulans* while others can be derived from bacteria—yeast in fact protect themselves with a photolyase which can be used in humans, other microorganisms, plants, insects, amphibian and animal sources exist.

The photolyase enzymes function by light induced electron transfer from a reduced FAD factor to the environmental exposure produced pyrimidine dimers. The use of free radical inhibitors or quenchers such as antioxidants can also be used to supplement the photolyase therapy. Other light activated chromophores may be utilized with light sources and properly selected parameters to further enhance, stimulate, photomodulate, photoactivate or photoinhibit the target or supporting cells or tissue to promote the most effective treatment.

There are many causes of free radical damage to cells. In one embodiment wound healing can be accelerated by utilizing a combination of antioxidants, cell growth factors, direct photomodulation (photoactivation) of cells, and photoreactivation through photolyases. Topical or systemic therapy with the proper cofactors and replacing any deficiencies of cofactors can further enhance wound healing. For example, a chonic leg ulcer wound could be treated with an antioxidant mixture of vitamin E, vitamin C and glutathione, as well as cofactors such as fatty acids and keto acids and low level light therapy using and LED array with parameters selected to photostimulate fibroblasts and epithelial cells could also receive treatment with a photolyase and blue light therapy thus greatly accelerating wound healing and healing wounds or burns that would otherwise not be treatable.

The potential uses of photolyases and light therapy include: the treatment or repair or reverse nerve damage or diseases including spinal cord injuries and diseases; cancer or cancer treatment related problems including radiation and chemotherapy; cervical dysplasia and esophageal dysplasia (Barrett's esophagus) and other epithelial derived cell or organ disorders such as lung, oral cavity, mucous membranes, etc.; eye related diseases including but not limited to macular degeneration, cataracts, etc.

There are very broad health and commercial applications of photolyase mediated photorepair or photoreactivation of DNA (or RNA) damage with flavin radical photoreduction/

DNA repair via photomodulation or native or exogenously applied natural or synthetic or genetically engineered photolyases. The addition of topical. Oral, or systemically administered photolyases and also their cofactors or cofactors of the cells whose DNA is being repaired further enhance these applications. The enhanced delivery of such substances topically via ultrasound assisted delivery, via alteration of the skin's stratum corneum, and/or via special formulations or via special delivery vehicles or encapsulations are yet an additional enhancement to this process.

There are also blue light photoreceptors such as cryptochrome which photomodulate the molecular clocks of cells and the biological or circadian rhythm clocks of animals and plants—that is the mechanism which regulates organism response to solar day/night rhythms in living organisms. These protein photoceceptors include vitamin B based crytochromes. Humans have two presently identified cryptochrome genes—which can be directly or indirectly photomodulated (that is photoactivated or photoinhibited).

The clinical applications include treatment of circadian rhythm disorders such as 'jet lag', shift work, etc, but also insomnia, sleep disorders, immune dysfunction disorders, space flight related, prolonged underwater habitation, and other disturbances of circadian rhythm in animals. Circadian issues also exist for many other living organisms including the plant kingdom.

Warts can be treated using exogenous or endogenous chromophores with either photothermal or non thermal photomodulation techniques—or a combination of both. Examples of preferred embodiments of endogenous chromophores include the targeting of the vascular blood supply of the wart with either method. Anther preferred embodiment is the use of a topically applied or injected or ultrasonically enhanced delivery of such a chromophore into the wart or its blood supply or supporting tissues with subsequent photomodulation or photothermal activation of the chromophore.

One such example would be that of a chlorophyll topical formulation similar to those described elsewhere in this application but of higher concentration and vehicle and particle size optimized for wart therapy and the anaotomic location of the warts (for example warts on the thicker skin of the hand might be formulated differently than that used for vaginal warts). An LED light source could be used for home use with 644 nm in a battery powered unit wherein the topical formula was applied daily and treatment of individual warts was performed with the proper parameters until the warts disappeared.

For the situation of vaginal warts, a cyclindrical device with an array of LED arranged and optically diffused such that the entire vaginal cavity could be properly illuminated in a medically performed procedure would represent another embodiment of this therapy. A wide range of substances can be utilized either as the primary chromophore or as adjunctive supporting therapy. These compounds are listed elsewhere in this application. In another embodiment an immune stimulator is utilized in conjunction with photomodulation with or without an exogenous chromophore. In yet another embodiment a higher powered light source either narrow or broad band can e utilized with the same chromophore therapy as outlined above, but with parameters selected so that the interaction with the chromophore is non photomodulation, but rather intense photothermal effect so as to damage or destroy the wart but with minimal damage to surrounding uninvolved and non supporting tissues.

In one embodiment a chlorophyll and carotenoid topical formulation is applied and natural sunlight with or without a selective sunscreen are used to interact with the topical formulation. Another embodiment utilizes an injected or ultrasonically enhanced topical delivery of a dye such as indocyanine green which has been used for vascular injections safely in other medical applications.

Papulosquamous, eczematous and psoriasiform and related skin disorders can be improved, controlled, reduced or even cleared by the same photomodulation or photothermal interaction with endogenous or exogenous chromophores. The process outlined for warts and the other disorders in this application may be used for such therapies. The use of ultrasound is particularly useful in the more scaly disorders in this group of diseases as are enzyme peels and other methods with gently remove scaling skin. Penetration of light into psoriasis presents for example a major problem with current therapies. Penetration of drugs and topical agents is likewise a major therapeutic challenge. If the dry skin on top of psoriasis is removed it is well known that this stimulates further growth of the plaque or lesion of psoriasis—yet removal is needed to allow the drugs to penetrate and for light to penetrate. Currently almost all psoriasis light therapy is ultraviolet light and thus the risk of skin cancer and also of photoaging is very significant with a lifetime of repeated ultraviolet light therapy. Also such therapy typically involves treating large areas or even the entire body (standing in a large light therapy unit is like being in a tanning bed which is standing upright). Thus not only does the skin with psoriasis lesions get treated, but also all the normal uninvolved skin typically gets exposed to the damaging ultraviolet light.

Furthermore typical psoriasis treatments involve the use of oral drugs called psoralens. These drugs cross link DNA and are light activated. Thus DNA damage in produced not only by the ultraviolet light itself (like being out in sunlight but primarily ultraviolet A light), but in addition the psoralen drug produced DNA damage. Safety in children in an obvious concern as is use in pregnant or childbearing women.

The use of a topical light activated exogenous chromophore such as most of the agents listed in this application present no risk of DNA damage and also are generally very safe products—many are natural such as chlorophyll and can be safely used in children and pregnancy and child bearing age women. In addition the treatment is only activated where the topical agent is applied—unlike the use of oral psoralen drugs that activate not only the entire skin but also the retina and other tissues. The light used for this therapy is not only low in power, but it is for the most part visible or infrared light and is not ultraviolet—producing no DNA damage.

Thus the use of photomodulation or photothermal activation of exogenous light activated chromophores such as described herein represents a significant advance in safety and efficacy.

The photolyase embodiments described above also have some application for diseases such as psoriasis. For some cases of psoriasis are very extensive covering large amounts of the surface area of the body and may be resistant to other known therapies. The application of a topical formulation to the areas not being treated—or to all the body areas exposed to the traditional psoriasis phototherapy could receive a post treatment with the photolyase and blue light therapy—think of this as a type of 'antidote' to the ultraviolet psoriasis phototherapy wherein the repair of DNA damage to normal tissue was facilitated immediately following the psoriasis therapy—thus reducing significantly the risk of skin cancer and photoaging in future years.

Another embodiment involves the use of such a photolyase preparation in the evening after returning from a long day of occupational sun exposure or after an accidental sunburn. A spray or lotion containing the photolyase could be applied and then photorepair/photareacitvation of the acutely damaged DNA in the skin could be performed—and this could be performed with a large beam diameter home therapy unit—of by a white light source which contained enough of the desired wavelength at the proper parameters to produce this reaction. Additionally an antioxidant skin formulation could be also applied to minimize erythema and other undesired effects of the sunburn. One such embodiment would be the preparation described earlier with a combination of vitamin C, vitamin E and glutathione and free fatty acids and one or more keto acids. A similar formulation could contain these agents but utilize only one or two of the three antioxidants listed.

In vitro fertilization processes can also be enhanced by photomodulation—with or without an exogenous chromophore. This can simply target the cells or subcellular components themselves, as described in the applicants copending U.S. patent application Ser. No. 09/894,899 entitled "Method and Apparatus for Photomodulation of Living Cells", which is hereby incorporated by reference in its entirety.

This can result in a greater success rate of fertilization and/or growth of embryos or other desirable effects on this process. In one embodiment an LED light source is used to treat sperm of animals or humans or genetically engineered embryos or subcomponents thereof to enhance fertilization.

In another embodiment photolyase or other photoreparative or light activated DNA repair proteins or substances combined with photomodulation can be utilized to 'correct' DNA damage in embryonic tissues thus generating a normal or more normal embryo. This can be performed in vitro or in utero (utilizing tiny fiber optic delivery of the proper light parameters—or the light can be delivered from outside the body into the womb without the risk of introducing a fiber optic device.

Another process in which photomodulation can be utilized for significant benefit is in the stimulation of proliferation, growth, differentiation, etc of stem cells from any living organism. Stem cells growth and differentiation into tissues or organs or structures or cell cultures for infusion, implantation, etc (and their subsequent growth after such transfer) can be facilitated or enhanced or controlled or inhibited. The origin of such stem cells can be from any living tissue or organism. In humans stem cells for these embodiments may come from any source in the human body, but typically originate from the bone marrow, blood, embryo, placenta, fetus, umbilical cord or cord blood, and can be either naturally or artificially created either in vivo, ex vivo or in vitro with or without genetic alteration or manipulation or engineering. Such tissue can come from any living source of any origin.

Stem cells can be photoactivated or photoinhibited by photomodulation. There is little or no temperature rise with this process although transient local nondestructive intracellular thermal changes may contribute via such effects as membrane changes or structured conformational changes.

The wavelength or bandwidth of wavelengths is one of the critical factors in selective photomodulation. Pulsed or continuous exposure, duration and frequency of pulses (and dark 'off' period) and energy are also factors as well as the presence, absence or deficiency of any or all cofactors, enzymes, catalysts, or other building blocks of the process being photomodulated.

Photomodulation can control or direct the path or pathways of differentiation of stem cells, their proliferation and growth, their motility and ultimately what they produce or secrete and the specific activation or inhibition of such production.

Photomodulation can up-regulate or down-regulate a gene or group of genes, activate or inactivate enzymes, modulate DNA activity, and other cell regulatory functions.

Our analogy for photomodulation of stem cells is that a specific set of parameters can activate or inhibit differentiation or proliferation or other activities of a stem cell. Much as a burglar alarm keypad has a unique 'code' to arm (activate) or disarm (inhibit or inactivate) sending an alarm signal which then sets in motion a series of events so it is with photomodulation of stem cells.

Different parameters with the same wavelength may have very diverse and even opposite effects. When different parameters of photomodulation are performed simultaneously different effects may be produced (like playing a simple key versus a chord on a piano). When different parameters are used serially or sequentially the effects are also different—in fact depending on the time interval we may cancel out the prior photomodulation message (like canceling burglar alarm).

The selection of wavelength photomodulation is critical as is the bandwidth selected as there may be a very narrow bandwidth for some applications—in essence these are biologically active spectral intervals. Generally the photomodulation will target flavins, cytochromes, iron-sulfur complexes, quinines, heme, enzymes, and other transition metal ligand bond structures though not limited to these.

These act much like chlorophyll and other pigments in photosynthesis as 'antennae' for photo acceptor molecules. These photo acceptor sites receive photons from electromagnetic sources such as these described in this application, but also including radio frequency, microwaves, electrical stimulation, magnetic fields, and also may be affected by the state of polarization of light. Combinations of electromagnetic radiation sources may also be used.

The photon energy being received by the photo acceptor molecules from even low intensity light therapy (LILT) is sufficient to affect the chemical bonds thus 'energizing' the photo acceptor molecules which in turn transfers and may also amplify this energy signal. An 'electron shuttle' transports this to ultimately produce ATP (or inhibit) the mitochondria thus energizing the cell (for proliferation or secretory activities for example). This can be broad or very specific in the cellular response produced. The health of the cells and their environment can greatly affect the response to the photo modulation. Examples include hypoxia, excess or lack or ration of proper cofactors or growth factors, drug exposure (eg. reduced ubiquinone from certain anticholesterol drugs) or antioxidant status, diseases, etc.

The as yet unknown mechanism, which establishes 'priorities' within living cells, can be photomodulated. This can include even the differentiation of early embryos or stem cell population. Exogenous light activated chromophores may also be used alone or in combination with exogenous chromophores. Genetically altered or engineered stem cells or stem cells which have an inborn genetic error or defect or uncommon but desirable or beneficial trait may require a different 'combination' of parameters than their analogous 'normal' stem cells or may produce different cellular response if use the same combination of parameters. Using various methods of photomodulation or other techniques known in the art more specific cellular effects may be produced by 'blocking' some 'channels' that are photomodulated.

For example, consider an old fashioned juke box, if one selects the proper buttons one will set in motion a series of events resulting in the playing of a very specific and unique record or song. If however one were given a broom to push the buttons one would have to block all but the desired button to be selective. Likewise pushing an immediately adjacent button will not produce the desired outcome.

The magnitude of effects on cells may also be very dependent on the wavelength (when other parameters are the same). One such example is the contrast between irradiating chemical bonds in DNA with 302 nm light versus 365 nm light—the 302 nm light produces approximately 5000 times greater DNA pyrimidine dimers than the 365 nm only a short distance up the spectrum. Changing the wavelength can also convert the ratio or type of these dimers. Thus seemingly subtle changes in photomodulation or photochemical reaction parameters can produce very large and very significant differences in cellular effects—even at the subcellular level or with DNA or gene expression.

A final analogy is that photo modulation parameters can be much like a "morse code" to communicate specific 'instructions' to stem cells. This has enormous potential in practical terms such as guiding or directing the type of cells, tissues or organs that stem cells develop or differentiate into as well as stimulating, enhancing or accelerating their growth (or keeping them undifferentiated).

Another application of photomodulation is in the treatment of cellulite. Cellulite is a common condition which represents a certain outward appearance of the skin in certain anatomic areas—most commonly on the upper legs and hips which is widely regarded as cosmetically undesirable. Cellulite is the result of a certain anatomic configuration of the skin and underlying soft tissues and fat which may involve abnormalities of circulation or microcirculation or metabolic abnormalities—predominantly in the fat and supporting tissues. Photomodulation or photothermal treatments of the adipocytes (fat cells) or their surrounding supporting structures and blood supply alone or in combination can reduce the appearance of cellulite and/or normalize the structure and function of the tissues involved with the cellulite.

Photomodulation of adipocytes can be performed using endogenous chromophores such as the adipocytes themselves, their mitochondria or other targets within the adipocyte electron transport system or respiratory chain or other subcellular components. Exogenous light or electromagnetically activated chromophores can also be photomodulated (photoactivated or photoinhibited) or photothermal interactions can also occur. Examples of such chromophores are listed elsewhere in this application and can be topically or systemically introduced into the target tissues or adipocytes or surrounding blood vessels. The use of externally or internally applied ultrasound can be utilized either to enhance delivery of the chromophore or to alter local circulation or to provide thermal effect or to provide destructive effect or any combination of these actions.

In one embodiment the chromophore is delivered into the fat layer under the skin on the thigh using external ultrasound to enhance skin permeability and also enhance transport. The alteration of the stratum corneum alone or in combination with the ultrasound can further enhance delivery of the chromophore. External massage therapy from various techniques can be used to enhance the treatment process. In another embodiment chromophore is injected into the fat layer prior o treatment with light. Some light therapy with or without ultrasound may be used to photomodulate or photothermally or ultrasonically increase or otherwise alter the circulation or microciruclation or local metabolic processes in the areas affected by cellulite or other tissues. The proper light parameters are selected for the target adipocytes, blood vessels, exogenous chromophores, etc. Since some of the target tissues in cellulite are deeper than for example wrinkles or acne, typically long enough wavelengths of light must be utilized so that the light penetrated deeply enough to reach the target tissue.

Various topical or systemic agents can also be used to enhance the cellulite reduction treatments. Some of these include various cofactors for the metabolic or adipocyte interactions described and have been previously described herein.

Additional topical agents for inhibiting hair growth include inhibitors of ornithine decarboxylase, inhibitors of vascular endothelial growth factor (VEGF), inhibitors of phospholipase A2, inhibitors of S-adenosylmethionine. Specific examples of these, but not limited to, include licorice, licochalone A, genestein, soy isoflavones, phtyoestrogens, vitamin D and derivatives, analogs, conjugates, natural or synthetic versions or genetically engineered or altered or immunologic conjugates with these agents.

Also the same topical agents, exogenous light activated chromophores and treatments described for cellulite above also are hereby incorporated into methods for reducing the growth of hair. Increasing the circulation or microcirculation of the hair bearing skin may also be accomplished by simply producing vasodilation by any method know to those skilled in this art. Some examples of topical agents which might be used to create such vasodilation include, but are not limited to: *capsicum, ginseng*, niacinamide, minoxidil, etc.

The present invention is further illustrated by way of the following examples.

Example 1

Acne Reduction—Continuous Treatment

A team of blinded expert graders viewing before and after photos of patients subjected to the non-ablative LILT ("Low Intensity Light Therapy") of the present invention score the global improvement of visible acne prominent in the facial area.

Six females are treated to reduce acne by, first, treating their skin with a topical composition containing about 2.5%, by weight copper chlorophyllin as the active ingredient. The treatment includes subjecting the target area of the patient's skin that has been treated with the topical composition to a filtered fluorescent light operated continuously and providing full-face coverage, i.e., the entire face of the patient is subjected to the light from the light source. Three treatments over 12 weeks to the entire face with at a light intensity of 11 milliwatts for 15 minutes per treatment session, resulting in a total energy exposure of 10.0 J/cm$^2$. Thermal injury is produced with blood vessels included among the target chromophores (but no skin wound care is needed). The average reduction in acne is shown in Table 1. The light source has a dominant emissive wavelength in the range of 410 nm to 420 nm and is centered at 415 nm.

TABLE 1

| Week | Value Averaged Value of Reduction |
|---|---|
| 0 weeks | 0% |
| 4 weeks | 28% |
| 8 weeks | 56% |
| 12 weeks | 64% |

Example 2

Acne Reduction—Pulsed Treatment

A team of blinded expert graders viewing before and after photos of patients subjected to the non-ablative LILT ("Low Intensity Light Therapy") of the present invention score the global improvement of visible acne on the facial area.

Six females are treated for acne by, first, contacting their skin once nightly for each night during the 2 weeks preceding the treatment session with a topical composition containing a mixture of 2.0% chlorophyll a, 2.0% chlorophyll b, and 5% carotenoids as the active ingredients. The laser diode treatment includes subjecting the target area of the patient's skin that has been treated with the topical composition to a laser diode light having a pulse width of 800 msec and a pulse frequency of 1 hz (1 pulse per second). Three pulses are administered. Six treatments over 12 weeks to the entire face with 400 nm laser diode with a 10 cm beam diameter at an intensity ranging 2500 milliwatts/cm2. The average reduction in acne is shown in Table 2.

TABLE 2

| Week | Value Averaged Value of Reduction |
|---|---|
| 0 weeks | 0% |
| 2 weeks | 36% |
| 7 weeks | 58% |
| 12 weeks | 82% |

Example 3

Acne and Acne Scarring Reduction Combined Continuous Wave/Pulsed Treatment

Three females showing active acne and acne scarring in the facial area are tested for improvement in scar prominence, skin texture, and scar visibility before and after receiving treatment in accordance with the non-ablative method of the present invention used in conjunction with a topical composition containing the active ingredient chlorophyll in a carrier suspension of microsponges having a diameter of 5 microns or less. Measurements are taken from by utilizing subjective evaluations conducted by trained medical personnel. The topical treatment includes applying the carotenoid composition containing about 5% carotenoids in a liposome carrier (alternatively, microsponges can be used having an average diameter of 5 microns) to the skin of the facial area and allowing it to penetrate the stratum corneum for approximately 15-20 minutes prior to beginning treatment. The first step in the treatment process is to expose the facial area to a continuos wave from a filtered metal halide lamp having a dominant emissive wavelength, i.e., an emission peak, at about 415 nm+/−5 nm and an energy output of 100 mW/cm² for approximately 10 minutes. The patient's facial area is then exposed to a pulsed LED treatment includes subjecting the target chromophore fibroblasts and subcellular components thereof to LED light having a pulse width of 250 msec and a pulse spacing of 250 msec for 90 pulses. Six treatments over 12 weeks to the entire face with the metal halide source as previously described and a 590 nm multichromatic LED, i.e., an LED having an emission peak at about 590 nm and putting out medically useful light in the range of about 585 nm to about 595 nm, at an intensity ranging from 1.05-2.05 µWatts. Further, the treatment maintains a skin temperature below the threshold of thermal injury. The average improvement in acne scar visibility is shown in Table 3. In accordance with the present invention, this dual-source treatment method employs the metal-halide light source to treat the active acne and the LED source to reduce or eliminate the visibility of acne scars.

TABLE 3

| Percent Improvement | Pre treatments | Post treatments (%) |
|---|---|---|
| Skin Elasticity | 0 | 85 |
| Scarring | 0 | 46 |
| Active Acne Lesions | 0 | 79 |

Example 4

Acne Scar Reduction—Pulsed Treatment

A team of blinded expert graders viewing before and after photos of patients subjected to the non-ablative LILT ("Low Intensity Light Therapy") of the present invention score the global improvement of visible acne scarring.

Six females were tested for reduction of acne scar visibility. The LED treatment includes subjecting the patient's skin to a LED light having a pulse width of 250 msec and a pulse spacing of 250 msec for a period of 90 pulses. Eight treatments over 16 weeks to the entire face with 590 nm multichromatic LED at an intensity ranging from 1.0-2.0 µWatts. Having a bandwidth of +/−5-15 nm, the LED therefore produces light in the wavelength range of from 575 nm to 605 nm. Further, the treatment maintains a skin temperature below the threshold of thermal injury. The average reduction in visible acne scarring is shown in Table 4.

TABLE 4

| Week | Value Averaged Value of Reduction |
|---|---|
| 0 weeks | 0% |
| 4 weeks | 42% |
| 8 weeks | 51% |
| 12 weeks | 48% |

Example 5

Acne Reduction—Continuous Light

A method for treating acne by a combination of photothermal and photomodulatory treatment is used to reduce the presence of acne bacteria, resulting in a substantial reduction in the existence of acne on the facial area. In this example, dual chromophores are targeted. A native, naturally occurring porphyrin in acne and an exogenous chromophor.

Pretreatment is performed using a topically applied chromophore. In this example, the topical chromophor is an aqueous solution of Na Cu Chlorophyllin and carotenoids is applied to the skin. The skin is first cleansed with a low residue cleansing solution, then a pH adjusting astringent lotion is applied by a 5-10 minute application of an enzyme mask for removing skin debris and a portion of the stratum corneum. The topical chromophore is applied and delivery of the chromophore is enhanced with a 3 megahertz ultrasound emitter using a duty cycle of 25% and 1.5 watts output using a massage-like motion to cover the entire face for 5 minutes and the shoulders for 5 minutes. Any excess lotion is then removed. The cleansing solution used for this example should include at least 40% of either an acetone, ethyl acetate, or ethyl/isopropyl alcohol solvent, from about 1% to about 4% salicylic acid as a penetrant enhancer, and about 5% glycerin, included as a moisturizer.

A filtered fluorescent light source having a dominant emission at 420 nm is set to emit continuously for 20 minutes at an intensity of 10 Joules/cm$^2$. The entire face and upper back of the patient is treated with minimal overlap during each of 6 treatment sessions, each spaced two week apart. Approximately an 85% reduction in acne is observed.

Example 6

Home-Use Device and Treatment

The treatment method of Example 5 is carried out. The patient continues the treatment at home using a home-use device comprising a hand-held LED device, a lotion containing an aqueous solution of about 2%, by weight, chlorophyll and about 2%, by weight, of a carotenoid, and a wavelength selective sunscreen.

The patient applies a chlorophyll-containing topical solution to the areas previously treated for acne scarring once per day, preferably but not necessarily in the morning. Further, the patient applies a sunscreen typical of those known in the art except that it is formulated to permit the passage of radiation having a wavelength in the range of about 400 nm to about 420 nm and 600 nm to about 660 nm to allow natural sunlight to further aid the treatment process. The carotenoids provide protection to the skin against damage from ultraviolet radiation received from sunlight. Finally, the patient uses the hand-held LED device 1-2 times per day. The LED device emits radiation having a dominant emission at about 644 nm+/−5 nm at an energy output of approximately 20 microwatts in a continuous wave. Each treatment session covers active acne lesions for acne lesions for approximately 2 minutes. A further reduction in the visibility of acne scarring is observed. Additional improvement in acne scar reduction can be achieved using a 590 nm multichromatic LED at an intensity ranging from 1.0-2.0 µWatts as described in prior examples.

Example 7

Mixed LED Panel Treatment Array

An LED array includes both blue LEDs having a dominant emission at 415 nm to treat active acne and yellow LEDs having a dominant emission at 590 nm to treat acne scarring. The skin is pretreated in the same manner as described in Example 5. The LED array is then positioned to cover the entire facial area of the patient with a 20 minute continuous wave of blue light (415 nm) and an exposure of yellow (590 nm) light pulsed on for 250 millseconds and off for 250 milliseconds. Approximately 100 pulses are delivered.

Example 8

Sebaceous Gland Size Reduction

Female skin exhibiting active acne rosacea and numerous sebaceoushyperplasia lesions is treated with a metal halide light source having a dominant emission centered at 415 nm+/−5 nm and an energy output of 100 mW/cm$^2$ for approximately 10 minutes after having been treated with a topically applied composition containing chlorophyll and carotenoids as the active ingredients. A mixture of 2.0% chlorophyll a and b, 6.0% carotenoids (carotenses and xanthophylls) and 1.5% phycobilin is used. All percentages are by weight. Three treatments are administered at two-week intervals. Visual inspection shows a reduction in sebaceous gland size of 40%-60%.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

I claim:

1. A device for treating skin disorders, comprising:
 a first radiation source configured to expose skin to narrowband multichromatic electromagnetic radiation having at least one dominant emissive wavelength between about 300 nm and about 1400 nm and a bandwidth of +/−at least 5 nm around the dominant emissive wavelength, and
 a second radiation source configured to expose the skin to narrowband multichromatic electromagnetic radiation having at least one dominant emissive wavelength between about 300 nm and about 1400 nm and a bandwidth of +/−at least 5 nm around the dominant emissive wavelength,
 wherein the device is configured to expose the skin to the narrowband multichromatic electromagnetic radiation of the first radiation source prior to being exposed to the narrowband multichromatic electromagnetic radiation of the second radiation source.

2. The device of claim 1, wherein the first radiation source is selected from the group consisting of a light emitting diode, a laser diode, a dye laser, metal halide lamps, a flashlamp, a mechanically filtered fluorescent light source, a mechanically filtered incandescent or filamentous light source, or combinations thereof.

3. The device of claim 1, wherein the second radiation source is selected from the group consisting of a light emitting diode, a laser diode, a dye laser, metal halide lamps, a flashlamp, a mechanically filtered fluorescent light source, a mechanically filtered incandescent or filamentous light source, or combinations thereof.

4. The device of claim 1 wherein either, or both, of the first or second radiation source emits infrared radiation.

5. The device of claim 1, wherein the device is configured to deliver a total energy fluence to the living tissue is less than about 10 J/cm$^2$.

6. The device of claim 1, wherein the bandwidth of the first and second radiation source is less than or equal to about +/−100 nm around the dominant emissive wavelength.

7. A device for treating skin disorders, comprising:
a first radiation source that includes at least one light emitting diode and configured to expose skin to narrowband multichromatic electromagnetic radiation having at least one dominant emissive wavelength between about 400 nm and about 700 nm and a bandwidth of +/−at least 5 nm around the dominant emissive wavelength,
a second radiation source that includes at least one light emitting diode and configured to expose the skin to narrowband multichromatic electromagnetic radiation having at least one dominant emissive wavelength between about 700 nm and about 1400 nm and a bandwidth of +/−at least 5 nm around the dominant emissive wavelength,
wherein the total energy fluence received by the skin is less than about 10 J/cm$^2$,
wherein the device is configured to expose the skin to the narrowband multichromatic electromagnetic radiation of the first radiation source prior to being exposed to the narrowband multichromatic electromagnetic radiation of the second radiation source.

\* \* \* \* \*